(12) United States Patent
Gupta et al.

(10) Patent No.: US 9,012,470 B2
(45) Date of Patent: Apr. 21, 2015

(54) THERAPEUTIC 5,6,5-TRICYCLIC ANALOGS

(75) Inventors: Varsha Gupta, Encinitas, CA (US); Joel Renick, San Diego, CA (US); Graeme Freestone, San Diego, CA (US); Alan P. Kaplan, San Diego, CA (US)

(73) Assignee: Dart NeuroScience (Cayman) Ltd. (KY)

( * ) Notice: Subject to any disclaimer, the term of this patent is extended or adjusted under 35 U.S.C. 154(b) by 316 days.

(21) Appl. No.: 13/270,982

(22) Filed: Oct. 11, 2011

(65) Prior Publication Data

US 2012/0095016 A1    Apr. 19, 2012

Related U.S. Application Data

(60) Provisional application No. 61/393,327, filed on Oct. 14, 2010.

(51) Int. Cl.
*A61K 31/437* (2006.01)
*C07D 471/14* (2006.01)
*C07D 487/14* (2006.01)
*A61K 31/496* (2006.01)

(52) U.S. Cl.
CPC ............ *A61K 31/437* (2013.01); *C07D 487/14* (2013.01); *A61K 31/496* (2013.01); *C07D 471/14* (2013.01)

(58) Field of Classification Search
USPC .............................................. 514/293; 546/82
See application file for complete search history.

(56) References Cited

U.S. PATENT DOCUMENTS

| | | | | |
|---|---|---|---|---|
| 4,479,955 | A * | 10/1984 | Yokoyama | 514/256 |
| 4,647,566 | A * | 3/1987 | Yokoyama | 514/293 |
| 6,734,190 | B2 | 5/2004 | Green et al. | |
| 2004/0044024 | A1 | 3/2004 | Green et al. | |

FOREIGN PATENT DOCUMENTS

WO    WO 2008/154447    12/2008

OTHER PUBLICATIONS

Atack et al., "The proconvulsant effects of the GABA$_A$ α5 subtype-selective compound RY-080 may not be α5-mediated," *Eur. J. Pharmacol.*, 548:77-82 (2006).
Barnard et al., "International Union of Pharmacology. XV. Subtypes of γ-Aminobutyric Acid$_A$ Receptors: Classification on the Basis of Subunit Structure and Receptor Function," *Pharmacol. Rev.*, 50(2):291-313 (1998).
Low et al., "Molecular and Neuronal Substrate for the Selective Attenuation of Anxiety," *Science*, 290:131-134 (2000).
McKernan et al., "Sedative but not anxiolytic properties of benzodiazepines are mediated by the GABA$_A$ receptor α$_1$ subtype," *Nat. Neurosci.*, 3(6):587-592 (2000).
Muller, "New trends in benzodiazepine research," *Drugs of Today*, 24(9):649-663 (1988).
Rudolph et al., "Benzodiazepine actions mediated by specific γ-aminobutyric acid$_A$ receptor subtypes," *Nature*, 401:796-800 (1999).
Takada et al., "Thienylpyrazoloquinolines: Potent Agonists and Inverse Agonists to Benzodiazepine Receptors," *J. Med. Chem.*, 31(9):1738-1745 (1988).
Yokoyama et al., "2-Arylpyrazolo[4,3-c]quinolin-3-ones: Novel agonist, Partial Agonist and Antagonist of Benzodiazepines," *J. Med. Chem.*, 25(4):337-339 (1982).
International Search Report and Written Opinion mailed May 2, 2012 of corresponding PCT Application No. PCT/US2011/055839 filed Oct. 11, 2011.
Melani F. et al., "Dipyrazolo[5,4-b:3',4'-d] Pyridines. Synthesis, Inhibition of Benzodiazepine Receptor Binding and Structure-Activity Relationships," *Il Farmaco*, vol. 44, No. 6, 1989, pp. 585-594.
Mitchinson, A. et al., "2,5-Dihydropyrazolo[4,3-c]pyridin-3-ones: functionally selective benzodiazepine binding site ligands on the GABA$_A$ receptor," *Bioorg. Med. Chem. Lett.*, vol. 14, No. 13, 2004, pp. 3441-3444.
Extended Search Report mailed Mar. 11, 2014 of corresponding European Application No. 11833275.8 filed May 14, 2013.

* cited by examiner

*Primary Examiner* — Barbara P Badio
*Assistant Examiner* — Sara E Townsley
(74) *Attorney, Agent, or Firm* — Knobbe Martens Olson & Bear LLP

(57) ABSTRACT

The invention provides a novel chemical series of formula I, as well as methods of use thereof for binding to the benzodiazepine site of the GABA$_A$ receptor and negatively modulating the α5 subtype of GABA$_A$, and use of the compound of formula I in the manufacture of a medicament for the treatment of GABA$_A$ receptor associated disorders. The invention further provides a method of modulation of one or more GABA$_A$ subtypes in an animal comprising administering to the animal an effective amount of a compound of formula (I).

12 Claims, No Drawings

THERAPEUTIC 5,6,5-TRICYCLIC ANALOGS

RELATED APPLICATION

This application claims the benefit of U.S. Provisional Application No. 61/393,327, filed Oct. 14, 2010, the disclosure of which is incorporated herein by reference in its entirety.

BACKGROUND OF THE INVENTION

1. Field of the Invention

The present invention is related to the use of novel derivatives of dipyrazolopyridine as modulators of $GABA_A$ α5 for the intended use of therapy for enhancing cognition.

2. Description of the Related Art

The inhibitory neurotransmitter γ-aminobutyric acid (GABA), serves as a ligand for two distinct classes of receptors, $GABA_A$ and $GABA_B$. The $GABA_A$ class is a ligand-gated ion channel while $GABA_B$ is a canonical seven transmembrane G-protein coupled receptor. The $GABA_A$ receptor is comprised of a number of subunits, including α, β, γ, and δ. Cloning of the individual subunits of the $GABA_A$ receptor has confirmed the existence, so far, of six α subunits, three β subunits, three γ subunits, and one δ subunit. The overall structure of the receptor is a pentamer with a minimum subunit requirement of at least one α subunit, one β subunit, and one γ subunit.

Due to afore mentioned diversity of subunits, there are more than 10,000 possible combinations of the subunits that comprise the $GABA_A$ receptor, though not all appear in nature. Specific combinations that have been identified to have biological relevance (and their relative abundance in rat brains, include α1β2γ2 (43%), α2β2/3γ2 (18%), α3βγ2/3 (17%), α2βγ1 (8%), α5β3γ2/3 (4%), α6βγ2 (2%), α6βδ (2%), and α4βδ (3%) (Barnard, E. A., et al. (1998) *Pharmacol. Rev.* 50: 291-313 incorporated herein in its entirety).

There are a number of distinct, small molecule binding sites on the $GABA_A$ receptor that modulate the activity of the receptor including sites for benzodiazepines, steroids, barbiturates, ethanol, and convulsants (e.g. picrotoxin). The GABA binding site is located at the α/β interface. A tremendous amount of pharmaceutical research has been invested in identifying compounds that bind to the benzodiazepine binding site (BZ-site), which is located at the α/γ interface. Binding of GABA is greatly modulated by binding of drugs to the BZ-site, which can cause a number of different pharmacological responses. Drugs such as diazepam and zolpidem, agonists of $GABA_A$ function, have shown historic success as anxiolytic agents (Muller, W. E. (1988) *Drugs of Today* 24: 649-663 incorporated herein in its entirety). More recent work has suggested that the sedative and hypnotic effects of these drugs are primarily due to interaction with the α1-containing receptors, therefore much effort has been focused on finding drugs that have preferential activity towards α2β2γ2 and α3βγ2 over α1βγ2 in order to maintain the anxiolytic activity but reduce the sedative side effects (Rudolph, U. F., et al. (1999) *Nature* 401: 796-800 incorporated herein in its entirety; Löw, K. F., et al. (2000) *Science* 290: 131-134 incorporated herein in its entirety; McKernan, R. M., et al. (2000) *Nat. Neurosci.* 3: 587-592 incorporated herein in its entirety).

The α5-subunit is predominantly found in the hippocampus, a part of the brain that plays a part in memory and spatial navigation. As a result, much research has been focused on identifying links between α5-containing GABA receptor function and cognition. Results from a number of laboratories have indicated that selective inverse agonism of the α5βγ2/3 $GABA_A$ receptor can show marked improvement of memory function in a number of animal models. There have been a growing number of examples of inverse agonists in both the patent and scientific literature (Yokoyama, N., et al. (1982) *J. Med. Chem.* 25: 337-339 incorporated herein in its entirety; Takada, S., et al. (1988) *J. Med. Chem.* 31: 1738-1745 incorporated herein in its entirety; Atack, J. R., et al. (2006) *European Journal of Pharmacology* 548: 77-82 incorporated herein in its entirety). A preferable profile for a cognitive enhancer is one that shows negative modulation at α5, but with less modulation of α1, α2, or α3 to minimize side effects such as convulsion or sedation. As yet, no α5 selective $GABA_A$ negative modulator has been brought to market, and only a limited number have been investigated in human clinical trials.

SUMMARY OF THE INVENTION

Herein described is the composition and use of a new chemical series that is shown to bind to the benzodiazepine site of the $GABA_A$ receptor and negatively modulates the α5 subtype of $GABA_A$. The general structure of formula I is shown below:

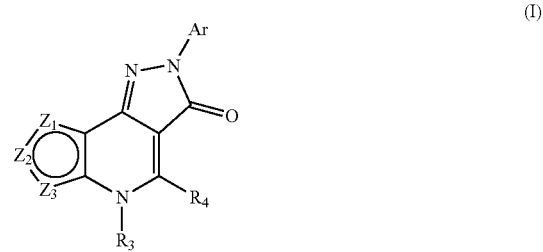

(I)

The compounds of Formula I encompass all possible tautomers of the chemical structures and mixtures thereof.

Embodiments, Aspects and Variations of the Invention

It is recognized in the following structures, when a formula is depicted as a mixture of two or more tautomeric structures, that the definitions of "$R_3$" can be different in each form.

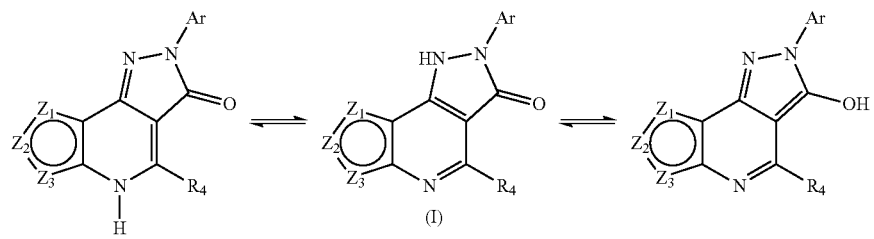

For example, in a compound of formula (I), in the structure on the left the definition of "$R_3$" can be hydrogen and in the other two structures "$R_3$" can be absent. Compounds represented by the tautomeric structures can exist in all possible tautomeric forms and mixtures thereof. Additionally, compounds need not exist in all three forms. A compound that can be represented by either drawn structure, whether in equilibrium or not in equilibrium, falls within the present disclosure.

It is recognized, that two tautomeric forms are drawn for some formulas. For simplicity, in some places (including the claims), only the tautomeric form on the right is drawn for an indicated formula, this is not to exclude the other tautomeric form. In places where only one tautomeric form is drawn for a formula the other tautomeric form is also contemplated.

One embodiment of the invention provides a compound of formula (I):

(I)

wherein:

$Z_1$, $Z_2$ and $Z_3$ are each independently N (nitrogen), $NR_7$ or $CR_8$, wherein at least one of $Z_1$, $Z_2$ or $Z_3$ is $NR_7$;

$R_7$ is —C(=Y)$NR_1R_2$;

$R_8$ is hydrogen, halo, ($C_1$-$C_6$)alkyl optionally substituted with up to 5 fluoro, or ($C_1$-$C_6$)alkoxy optionally substituted with up to 5 fluoro;

Y is O (oxygen) or S (sulfur);

$R_1$ and $R_2$ are each independently selected from the group consisting of hydrogen, ($C_1$-$C_6$)alkyl, ($C_2$-$C_6$)alkenyl, ($C_2$-$C_6$)alkynyl, hydroxy($C_1$-$C_6$)alkyl, ($C_1$-$C_6$)alkyl$OR_a$, ($C_1$-$C_6$)alkyl optionally substituted with up to 5 fluoro, ($C_1$-$C_6$)alkyl optionally substituted with up to 5 chloro, ($C_1$-$C_6$)alkoxy optionally substituted with up to 5 fluoro, ($C_1$-$C_6$)alkylN-$R_aR_b$, and aryl, or $R_1$ and $R_2$ are taken together with the nitrogen to which they are attached to form a heterocycle group optionally substituted with one or more $R_c$; wherein the heterocycle group optionally include one or more groups selected from O (oxygen), S(O)$_x$, and $NR_d$;

x is 0, 1 or 2;

Ar is aryl, or heteroaryl, each optionally substituted with one or more M;

$R_3$ is hydrogen, or oxide;

$R_4$ is selected from the group consisting of hydrogen, hydroxy, halo, hydroxy($C_1$-$C_6$)alkyl, ($C_1$-$C_6$)alkyl optionally substituted with up to 5 fluoro, and ($C_1$-$C_6$)alkoxy optionally substituted with up to 5 fluoro;

each $R_a$ and $R_b$ is independently hydrogen, ($C_1$-$C_6$)alkyl, aryl, heteroaryl, heterocycle, ($C_1$-$C_6$)alkylaryl, —S(O)$_x$($C_1$-$C_6$)alkyl, —S(O)$_x$aryl, —C(O)($C_1$-$C_6$)alkyl;

each $R_c$ is independently hydrogen, aryl, heteroaryl, heterocycle or ($C_1$-$C_6$)alkyl optionally substituted with up to 5 fluoro;

each $R_d$ is independently hydrogen, halo, oxo, hydroxy, —C(O)$NR_eR_f$, cyano, nitro, hydroxy($C_1$-$C_6$)alkyl, aryl, aryl ($C_1$-$C_6$)alkyl, ($C_1$-$C_6$)alkyl optionally substituted with up to 5 fluoro, ($C_1$-$C_6$)alkoxy optionally substituted with up to 5 fluoro, or ($C_1$-$C_6$)alkyl substituted with one or more $R_{dd}$;

$R_{dd}$ is hydroxyl, alkoxy, alkylamino or halo;

each M is independently hydrogen, halo, $CF_3$, $CF_2H$, hydroxy, methoxy, trifluoromethoxy, cyano, nitro, ($C_1$-$C_6$)alkyl, hydroxy($C_1$-$C_6$)alkyl, ($C_1$-$C_6$)alkoxy, —$NR_aR_b$, aryl, heteroaryl or heterocycle; and each $R_e$ and $R_f$ is independently ($C_1$-$C_6$)alkyl.

In some embodiments, Ar can be:

wherein W is CM or N (nitrogen); and each M is independently hydrogen, halo, $CF_3$, $CF_2H$, hydroxy, methoxy, cyano, nitro, ($C_1$-$C_6$)alkyl, hydroxy($C_1$-$C_6$)alkyl, ($C_1$-$C_6$)alkoxy, —$NR_aR_b$, aryl, heteroaryl or heterocycle.

In one embodiment, the compound of formula (I) has the formula Ia:

(Ia)

or tautomer thereof, or their pharmaceutically acceptable salts, wherein W is CM or N (nitrogen), and each M is independently hydrogen, halo, $CF_3$, $CF_2H$, hydroxy, methoxy, cyano, nitro, ($C_1$-$C_6$)alkyl, hydroxy($C_1$-$C_6$)alkyl, ($C_1$-$C_6$)alkoxy, —$NR_aR_b$, aryl, heteroaryl or heterocycle. In one embodiment, Y can be S (sulfur). In another embodiment, Y can be O (oxygen).

In another embodiment, the compound of formula (I) has the formula Ib:

(Ib)

tautomer thereof, or their pharmaceutically acceptable salts, wherein W is CM or N (nitrogen), and each M is independently hydrogen, halo, $CF_3$, $CF_2H$, hydroxy, methoxy, cyano, nitro, ($C_1$-$C_6$)alkyl, hydroxy($C_1$-$C_6$)alkyl, ($C_1$-$C_6$)alkoxy, —$NR_aR_b$, aryl, heteroaryl or heterocycle. In one embodiment, Y can be S (sulfur). In another embodiment, Y can be O (oxygen).

In another embodiment, the compound of formula (I) has the formula (Ic)

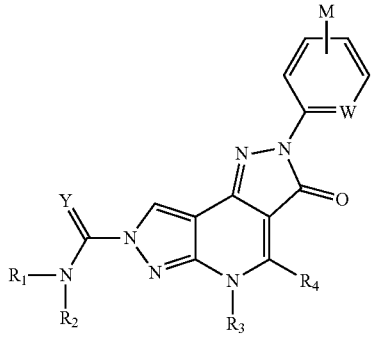

(Ic)

or tautomer thereof, or their pharmaceutically acceptable salts, wherein W is CM or N (nitrogen), and each M is independently hydrogen, halo, $CF_3$, $CF_2H$, hydroxy, methoxy, cyano, nitro, ($C_1$-$C_6$)alkyl, hydroxy($C_1$-$C_6$)alkyl, ($C_1$-$C_6$)alkoxy, —$NR_aR_b$, aryl, heteroaryl or heterocycle. In one embodiment, Y can be S (sulfur). In another embodiment, Y can be O (oxygen).

In another embodiment, the compound of formula (I) has the formula (Id)

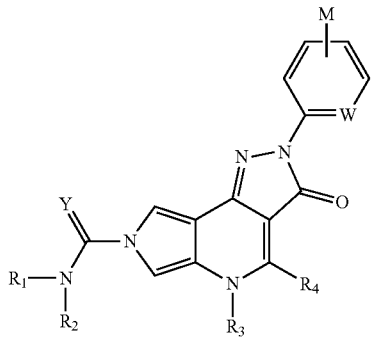

(Id)

or tautomer thereof, or their pharmaceutically acceptable salts, wherein W is CM or N (nitrogen), and each M is independently hydrogen, halo, $CF_3$, $CF_2H$, hydroxy, methoxy, cyano, nitro, ($C_1$-$C_6$)alkyl, hydroxy($C_1$-$C_6$)alkyl, ($C_1$-$C_6$)alkoxy, —$NR_aR_b$, aryl, heteroaryl or heterocycle. In one embodiment, Y can be S (sulfur). In another embodiment, Y can be O (oxygen).

In another embodiment, the compound of formula (I) has the formula (Ie)

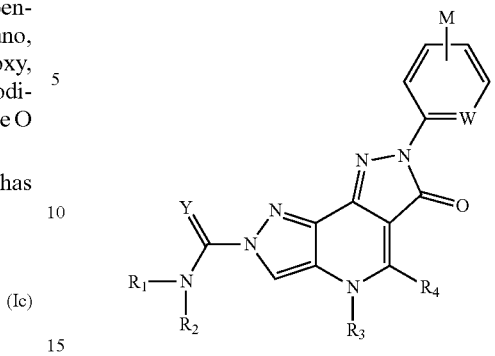

(Ie)

or tautomer thereof, or their pharmaceutically acceptable salts, wherein W is CM or N (nitrogen), and each M is independently hydrogen, halo, $CF_3$, $CF_2H$, hydroxy, methoxy, cyano, nitro, ($C_1$-$C_6$)alkyl, hydroxy($C_1$-$C_6$)alkyl, ($C_1$-$C_6$)alkoxy, —$NR_aR_b$, aryl, heteroaryl or heterocycle. In one embodiment, Y can be S (sulfur). In another embodiment, Y can be O (oxygen).

In another embodiment, the compound of formula (I) has the formula (If)

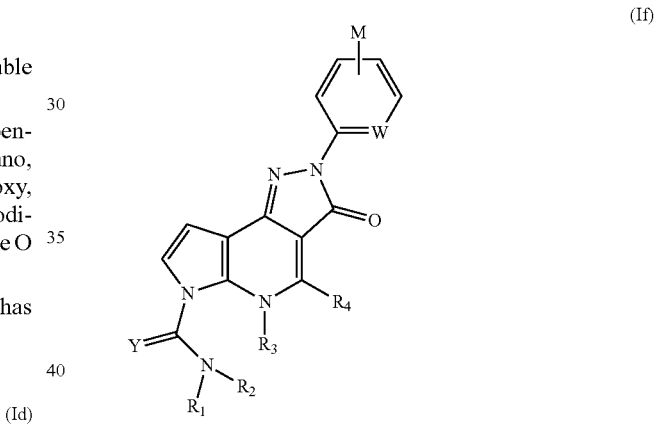

(If)

or tautomer thereof, or their pharmaceutically acceptable salts, wherein W is CM or N (nitrogen), and each M is independently hydrogen, halo, $CF_3$, $CF_2H$, hydroxy, methoxy, cyano, nitro, ($C_1$-$C_6$)alkyl, hydroxy($C_1$-$C_6$)alkyl, ($C_1$-$C_6$)alkoxy, —$NR_aR_b$, aryl, heteroaryl or heterocycle. In one embodiment, Y can be S (sulfur). In another embodiment, Y can be O (oxygen).

In another embodiment, the compound of formula (I) has the formula (IIa)

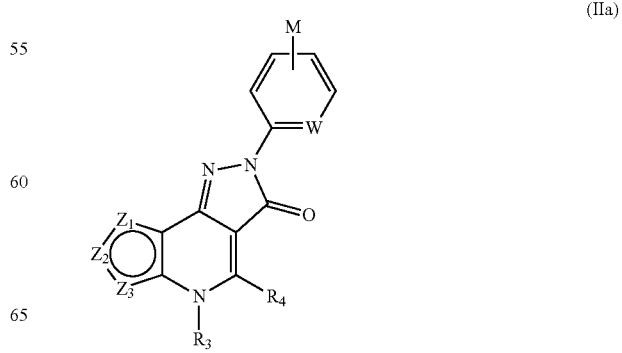

(IIa)

or tautomer thereof, or their pharmaceutically acceptable salts, wherein W is CM or N (nitrogen); each M is independently hydrogen, halo, $CF_3$, $CF_2H$, hydroxy, methoxy, cyano, nitro, $(C_1-C_6)$alkyl, hydroxy$(C_1-C_6)$alkyl, $(C_1-C_6)$alkoxy, —$NR_aR_b$, aryl, heteroaryl or heterocycle; $R_7$ is

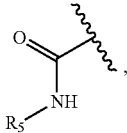

and $R_5$ is alkyl, chloroalkyl, alkylaminoalkyl, alkoxyalkyl or trifluoromethylalkyl.

In another embodiment, the compound of formula (I) has the formula (IIb)

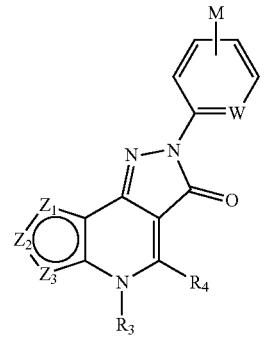

(IIb)

or tautomer thereof, or their pharmaceutically acceptable salts, wherein W is CM or N, (nitrogen); each M is independently hydrogen, halo, $CF_3$, $CF_2H$, hydroxy, methoxy, cyano, nitro, $(C_1-C_6)$alkyl, hydroxy$(C_1-C_6)$alkyl, $(C_1-C_6)$alkoxy, —$NR_aR_b$, aryl, heteroaryl or heterocycle, $R_7$ is

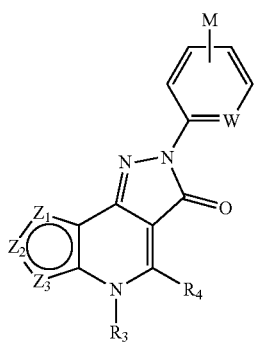

and n is 0, 1 or 2.

In another embodiment, the compound of formula (I) has the formula (IIc)

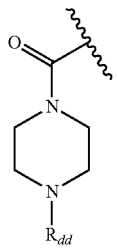

(IIc)

or tautomer thereof, or their pharmaceutically acceptable salts, wherein W is CM or N; (nitrogen), each M is independently hydrogen, halo, $CF_3$, $CF_2H$, hydroxy, methoxy, cyano, nitro, $(C_1-C_6)$alkyl, hydroxy$(C_1-C_6)$alkyl, $(C_1-C_6)$alkoxy, —$NR_aR_b$, aryl, heteroaryl or heterocycle; $R_7$ is

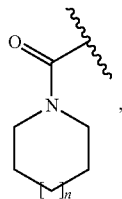

and $R_{dd}$ is $(C_1-C_6)$alkyl optionally substituted with hydroxyl, alkoxy, alkylamino or halo.

In another embodiment, the compound of formula (I) has the formula (IIa)

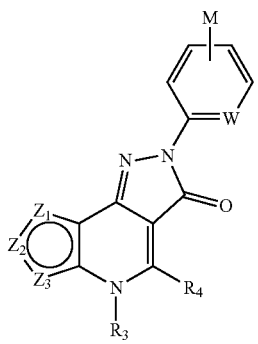

(IIIa)

or tautomer thereof, or their pharmaceutically acceptable salts, wherein W is CM or N (nitrogen); each M is independently hydrogen, halo, $CF_3$, $CF_2H$, hydroxy, methoxy, cyano, nitro, $(C_1-C_6)$alkyl, hydroxy$(C_1-C_6)$alkyl, $(C_1-C_6)$alkoxy, —$NR_aR_b$, aryl, heteroaryl or heterocycle, $R_7$ is

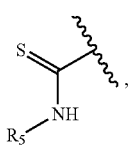

and $R_5$ is alkyl, chloroalkyl, alkylaminoalkyl, alkoxyalkyl or trifluoromethylalkyl.

In another embodiment, the compound of formula (I) has the formula (IVa)

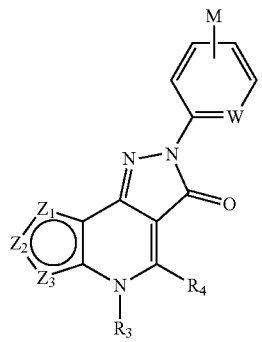

(IVa)

or tautomer thereof, or their pharmaceutically acceptable salts, wherein W is CM or N (nitrogen); each M is independently hydrogen, halo, $CF_3$, $CF_2H$, hydroxy, methoxy, cyano, nitro, $(C_1-C_6)$alkyl, hydroxy$(C_1-C_6)$alkyl, $(C_1-C_6)$alkoxy, $-NR_aR_b$, aryl, heteroaryl or heterocycle; $R_7$ is

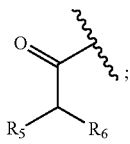

and $R_5$ or $R_6$ are independently alkyl, chloroalkyl, alkylaminoalkyl, alkoxyalkyl or trifluoromethylalkyl.

In another embodiment the compound is selected from the group consisting of:

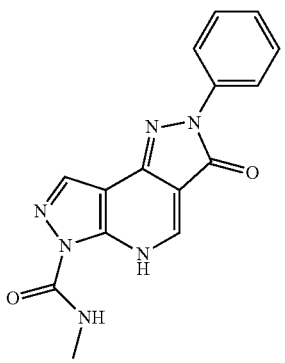

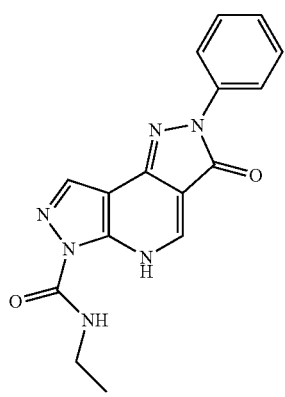 [SMILES: CCNC(=O)n1ncc2c3nn(-c4ccccc4)c(=O)c-3c[nH]c21]

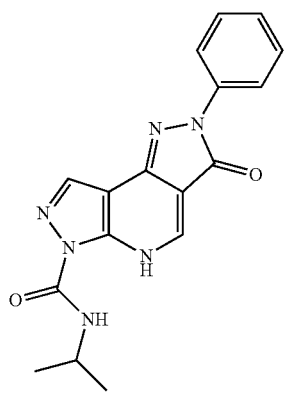

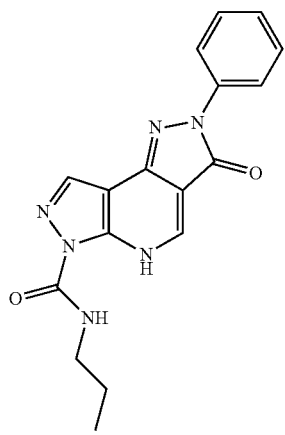 [SMILES: CCCNC(=O)n1ncc2c3nn(-c4ccccc4)c(=O)c-3c[nH]c21]

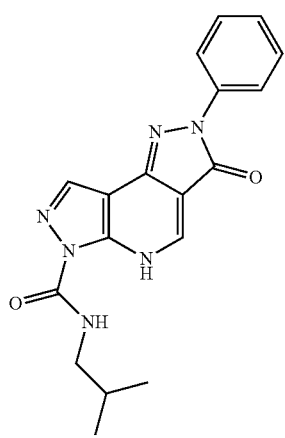 [SMILES: CC(C)CNC(=O)n1ncc2c3nn(-c4ccccc4)c(=O)c-3c[nH]c21]

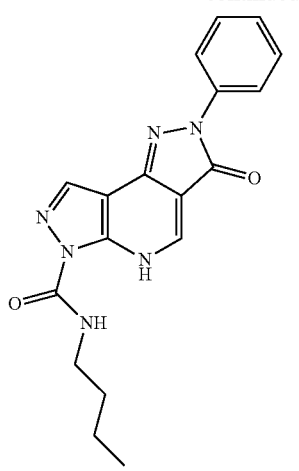 [SMILES: CCCCNC(=O)n1ncc2c3nn(-c4ccccc4)c(=O)c-3c[nH]c21]
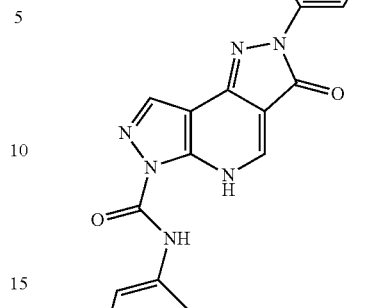
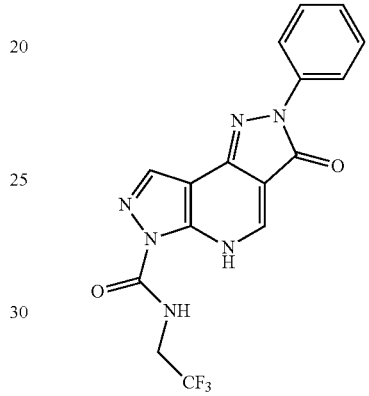
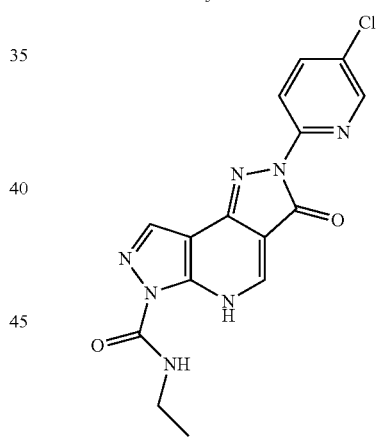
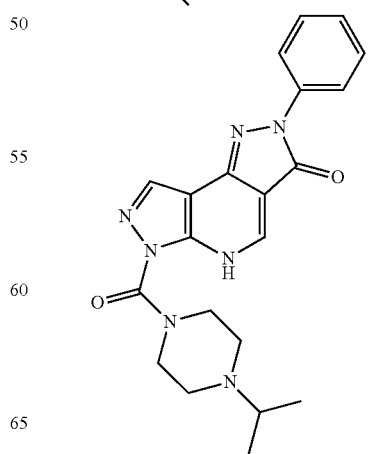

-continued
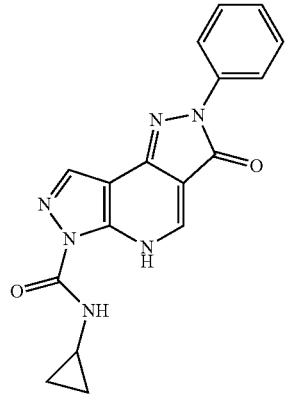
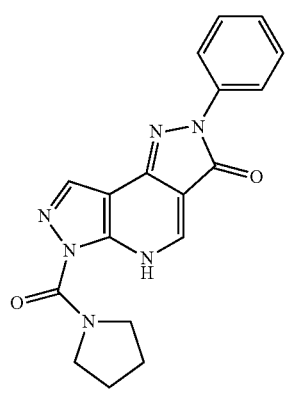
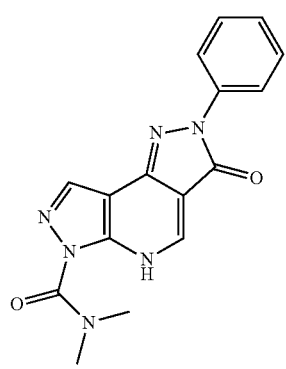
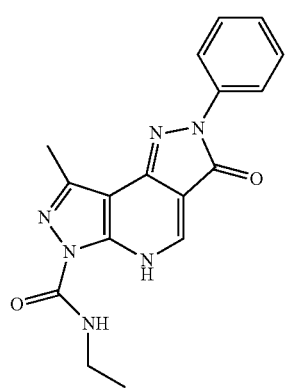
-continued
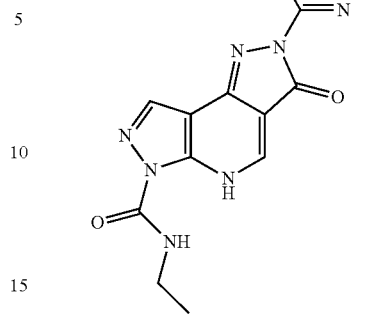
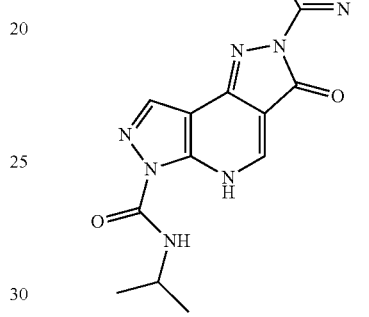
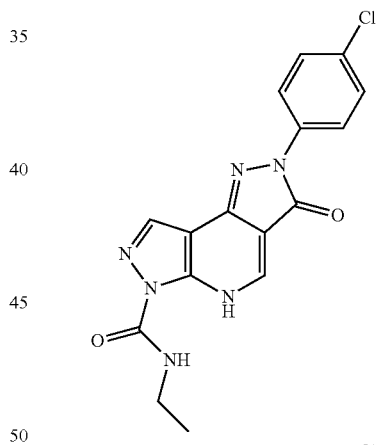
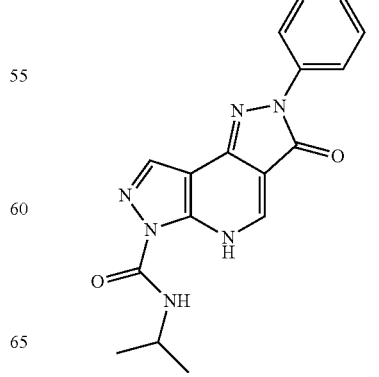

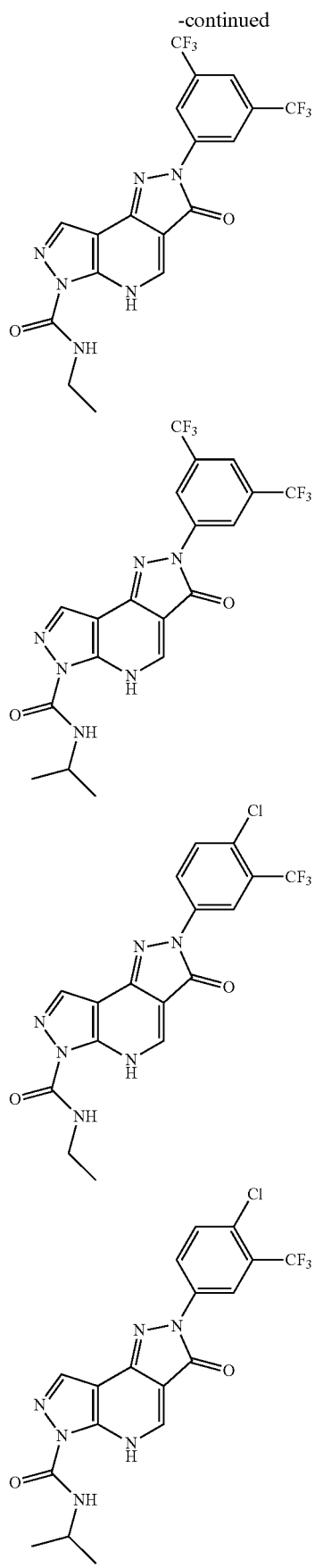
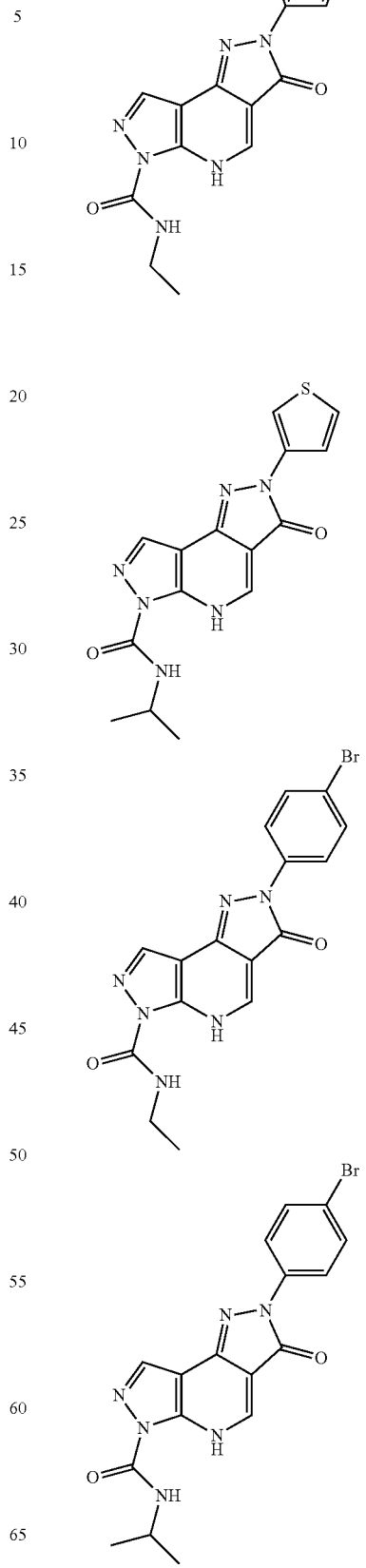

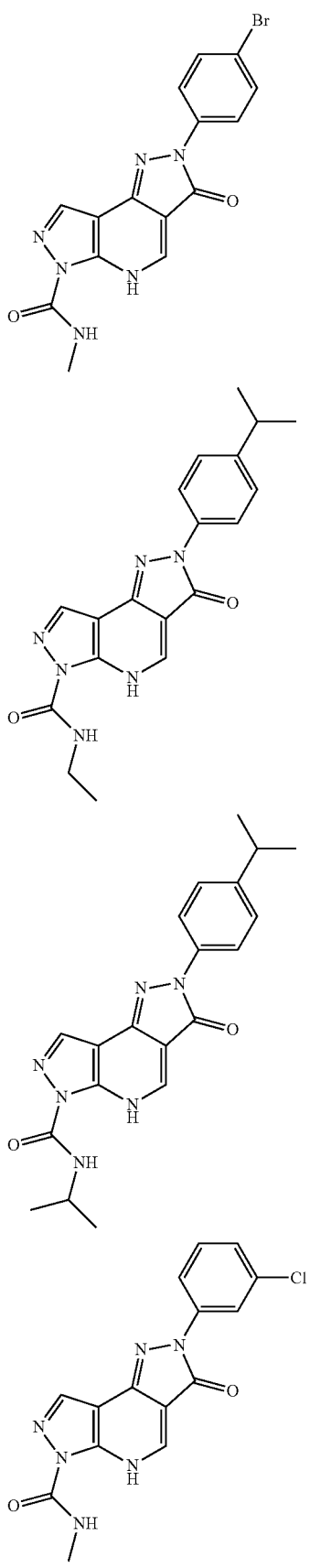
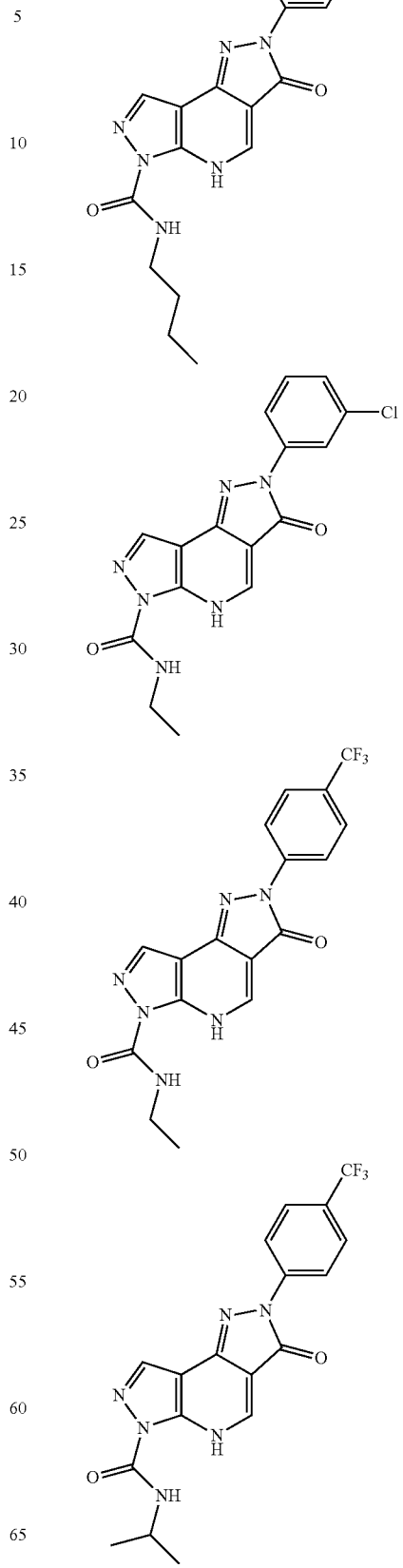

-continued
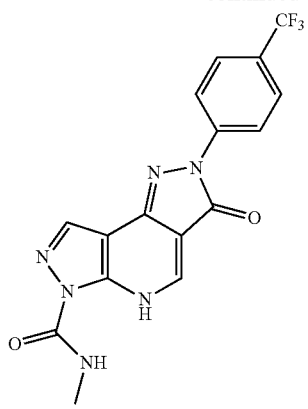
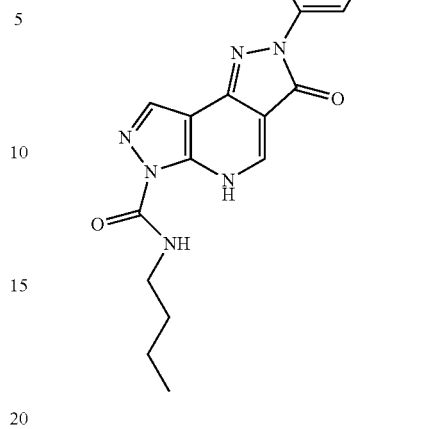
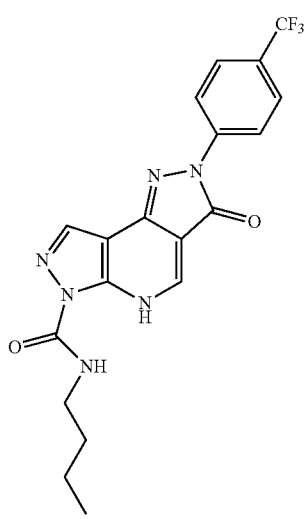
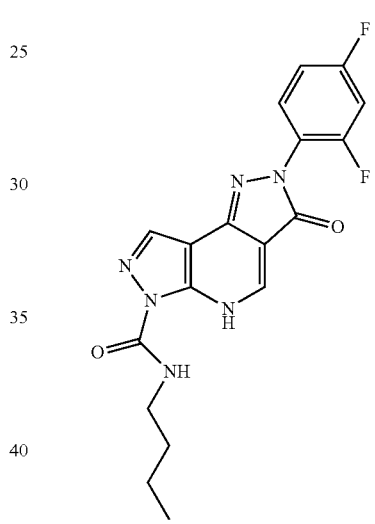
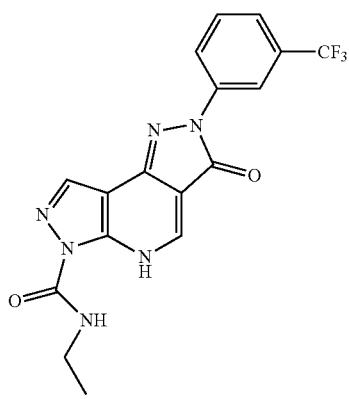
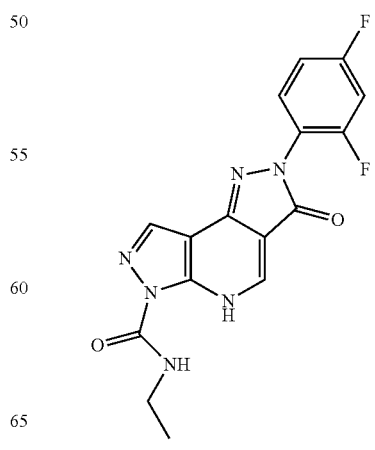

21
-continued
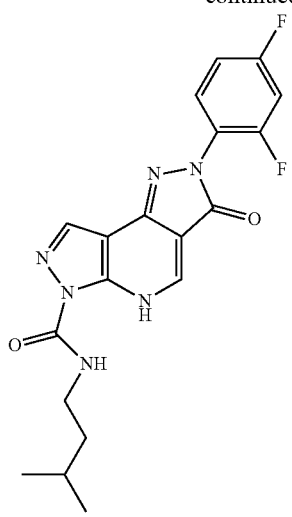
22
-continued
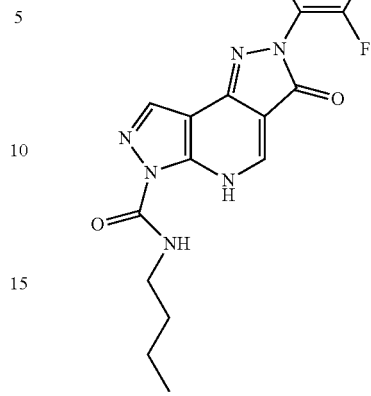
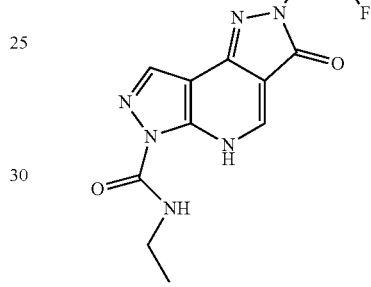
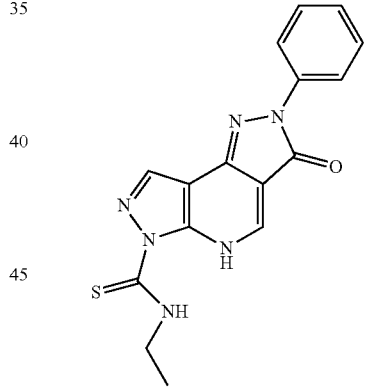
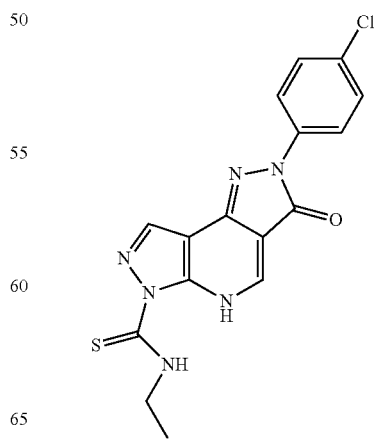

-continued
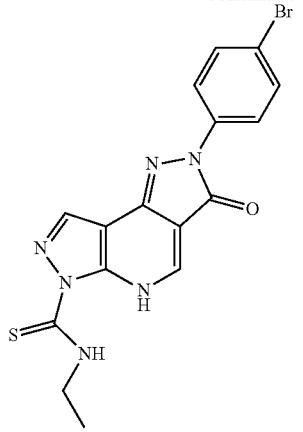
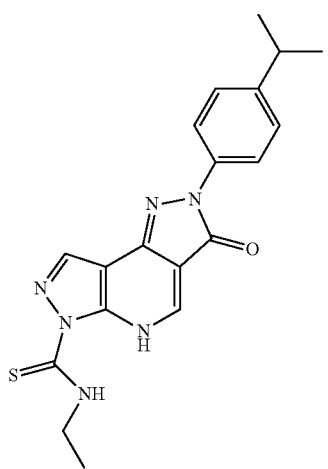
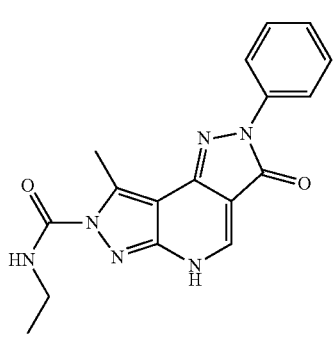
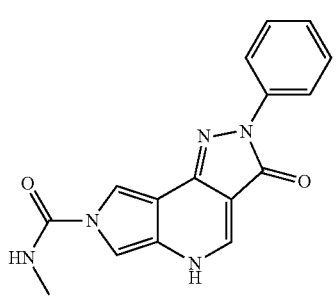
-continued
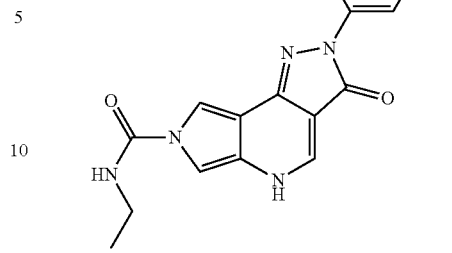
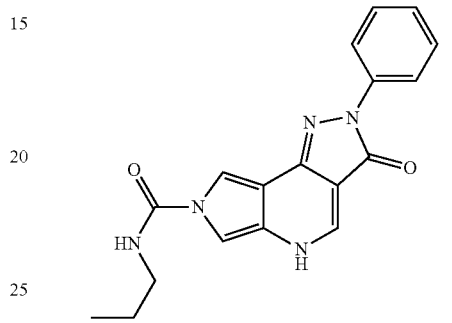
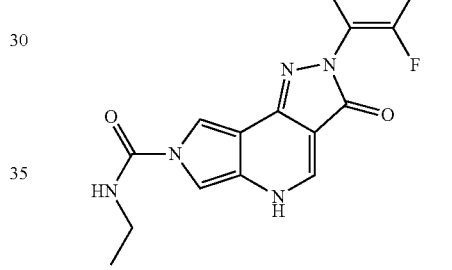
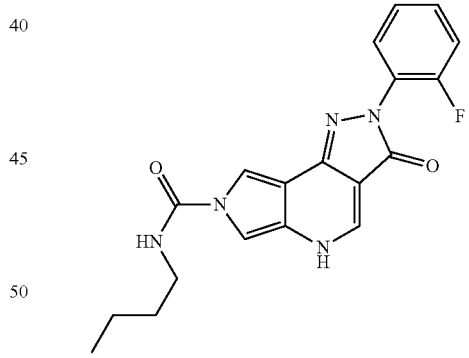
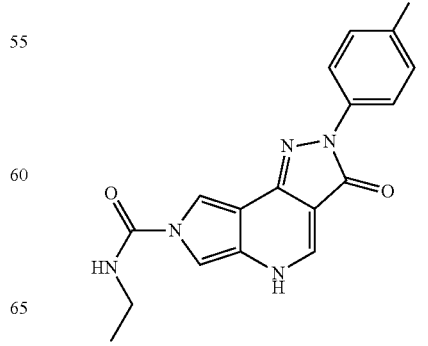

-continued
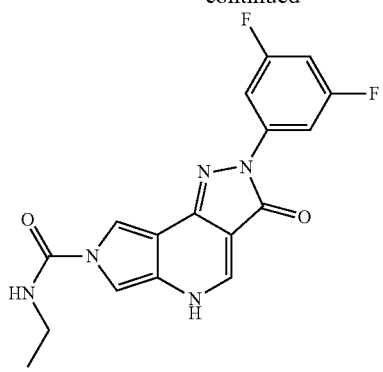
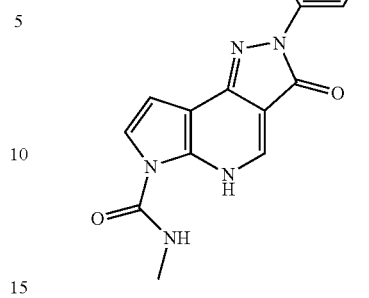
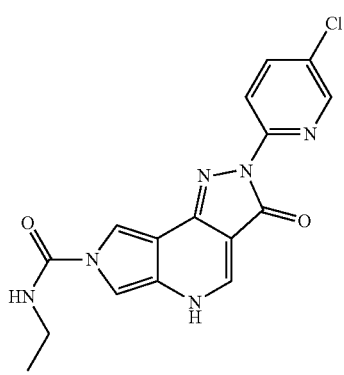
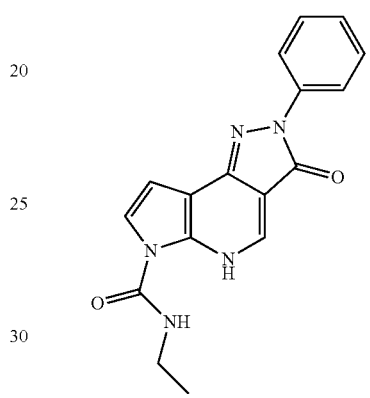
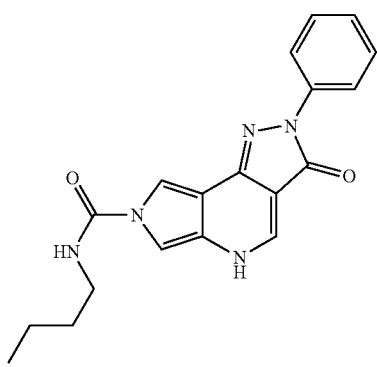
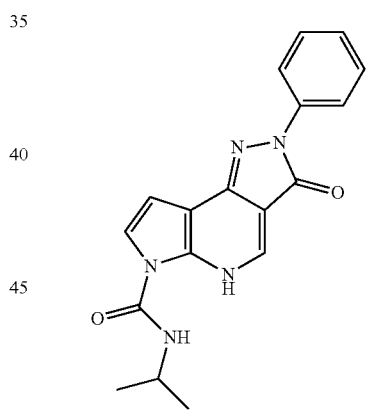
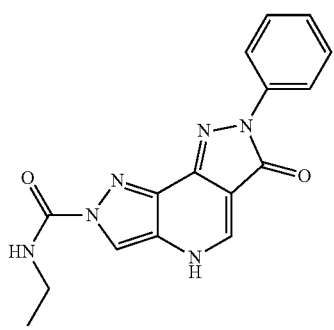
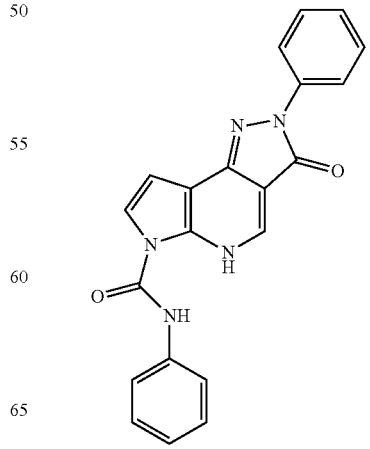

27
-continued

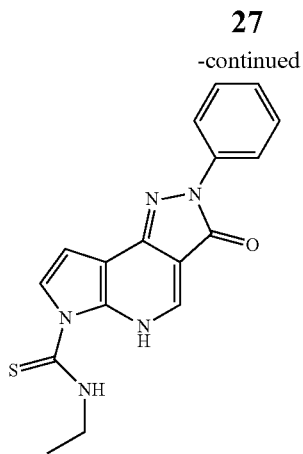

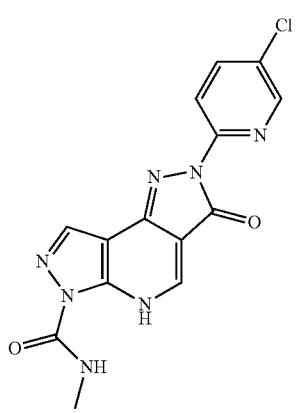

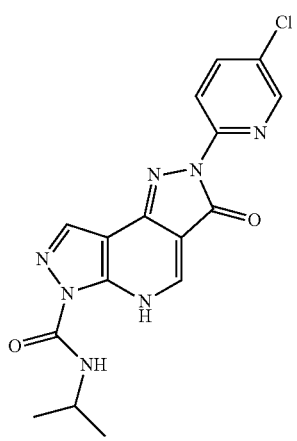

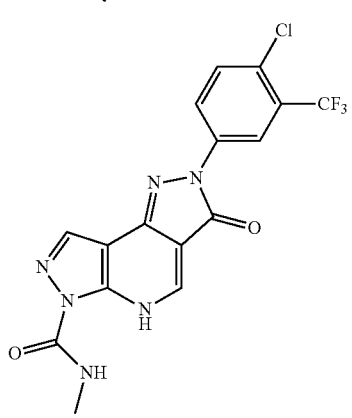

28
-continued

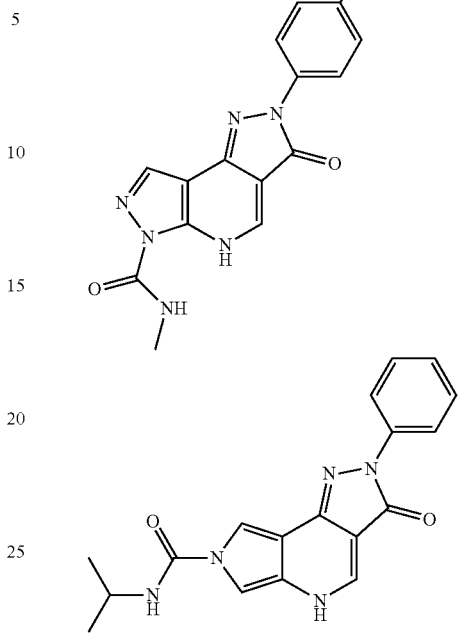

or tautomer thereof, or their pharmaceutically acceptable salts.

The present embodiments provide for a method of modulating one or more GABA$_A$ subtypes in an animal comprising administering to the animal an effective amount of a compound of formula (I):

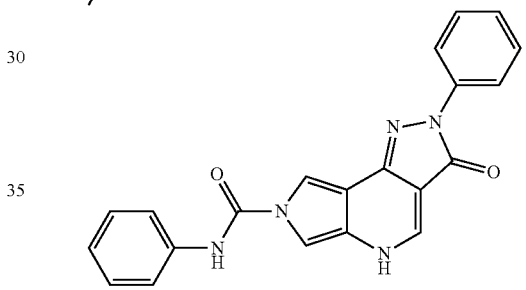
(I)

or tautomer thereof, or their pharmaceutically acceptable salts, wherein:

$Z_1$, $Z_2$ and $Z_3$ are each independently N (nitrogen), NR$_7$ or CR$_8$, wherein at least one of $Z_1$, $Z_2$ or $Z_3$ is NR$_7$;

R$_7$ is —C(=Y)NR$_1$R$_2$;

$R_8$ is hydrogen, halo, $(C_1-C_6)$alkyl optionally substituted with up to 5 fluoro, or $(C_1-C_6)$alkoxy optionally substituted with up to 5 fluoro;

Y is O (oxygen) or S (sulfur);

$R_1$ and $R_2$ are each independently selected from the group consisting of hydrogen, $(C_1-C_6)$alkyl, $(C_2-C_6)$alkenyl, $(C_2-C_6)$alkynyl, hydroxy$(C_1-C_6)$alkyl, $(C_1-C_6)$alkyl$OR_a$, $(C_1-C_6)$alkyl optionally substituted with up to 5 fluoro, $(C_1-C_6)$alkyl optionally substituted with up to 5 chloro, $(C_1-C_6)$alkoxy optionally substituted with up to 5 fluoro, $(C_1-C_6)$alkylN$R_aR_b$; and aryl, or $R_1$ and $R_2$ are taken together with the nitrogen to which they are attached to form a heterocycle group optionally substituted with one or more $R_c$; wherein the heterocycle group optionally include one or more groups selected from O (oxygen), $S(O)_x$, and $NR_d$;

x is 0, 1 or 2;

Ar is aryl, or heteroaryl, each optionally substituted with one or more M;

$R_3$ is hydrogen, or oxide;

$R_4$ is selected from the group consisting of hydrogen, hydroxy, halo, hydroxy$(C_1-C_6)$alkyl, $(C_1-C_6)$alkyl optionally substituted with up to 5 fluoro, and $(C_1-C_6)$alkoxy optionally substituted with up to 5 fluoro;

each $R_a$ and $R_b$ is independently hydrogen, $(C_1-C_6)$alkyl, aryl, heteroaryl, heterocycle, $(C_1-C_6)$alkylaryl, —$S(O)_x(C_1-C_6)$alkyl, —$S(O)_x$aryl, —$C(O)(C_1-C_6)$alkyl;

each $R_c$ is independently hydrogen, aryl, heteroaryl, heterocycle or $(C_1-C_6)$alkyl optionally substituted with up to 5 fluoro;

each $R_d$ is independently hydrogen, halo, oxo, hydroxy, —$C(O)NR_eR_f$, cyano, nitro, hydroxy$(C_1-C_6)$alkyl, aryl, aryl$(C_1-C_6)$alkyl, $(C_1-C_6)$alkyl optionally substituted with up to 5 fluoro, $(C_1-C_6)$alkoxy optionally substituted with up to 5 fluoro, $(C_1-C_6)$alkyl substituted with one or more $R_{dd}$;

$R_{dd}$ is hydroxyl, alkoxy, alkylamino or halo;

each M is independently hydrogen, halo, $CF_3$, $CF_2H$, hydroxy, methoxy, trifluoromethoxy, cyano, nitro, $(C_1-C_6)$alkyl, hydroxy$(C_1-C_6)$alkyl, $(C_1-C_6)$alkoxy, —$NR_aR_b$, aryl, heteroaryl or heterocycle; and each $R_e$ and $R_f$ is independently $(C_1-C_6)$alkyl.

In some embodiments, Ar can be:

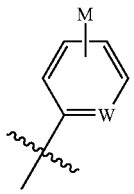

wherein W is CM or N (nitrogen); and each M is independently hydrogen, halo, $CF_3$, $CF_2H$, hydroxy, methoxy, cyano, nitro, $(C_1-C_6)$alkyl, hydroxy$(C_1-C_6)$alkyl, $(C_1-C_6)$alkoxy, —$NR_aR_b$, aryl, heteroaryl or heterocycle.

In one embodiment of the method, the modulation can be negative. In another embodiment, the modulation can be positive.

In one embodiment of the method, the $GABA_A$ subtypes is $GABA_A$ α5. In one embodiment of the method, the modulation can be negative. In another embodiment, the modulation can be positive.

Some embodiments disclosed herein relate to a method of treatment of a cognitive dysfunction in an animal comprising administering to the animal an effective amount of the compounds of the invention, or a pharmaceutically acceptable salt thereof, under conditions wherein the cognitive dysfunction is treated. In one embodiment, the animal is an aged animal. In another embodiment, the cognitive dysfunction is Alzheimer's disease, dementia or another neurodegenerative disease.

Some embodiments disclosed herein relate to a method of treatment of a psychiatric disorder in an animal comprising administering to the animal an effective amount of the compounds of the invention, or a pharmaceutically acceptable salt thereof, under conditions wherein the psychiatric disorder is treated.

Some embodiments disclosed herein relate to the use of the compounds of this invention, or a pharmaceutically acceptable salt thereof, for the manufacture of a medicament useful for modulation of one or more $GABA_A$ subtypes in an animal. In one embodiment of the method, the modulation can be negative. In another embodiment, the modulation can be positive. In one embodiment of the method, the $GABA_A$ subtypes is $GABA_A$ α5. In one embodiment of the method, the modulation can be negative. In another embodiment, the modulation can be positive.

Some embodiments disclosed herein relate to the use of the compounds of this invention, or a pharmaceutically acceptable salt thereof, for the manufacture of a medicament useful for treatment of a cognitive dysfunction in an animal. In one embodiment, the animal is a healthy animal. In another embodiment, the animal is an aged animal. In another embodiment, the cognitive dysfunction is Alzheimer's disease, dementia or another neurodegenerative disease.

Some embodiments disclosed herein relate to the use of the compounds of this invention, or a pharmaceutically acceptable salt thereof, for the manufacture of a medicament useful for treatment of psychiatric disorders in an animal. In one embodiment the psychiatric disorder is an anxiety disorder, sleep disorder, depression, or schizophrenia.

Some embodiments disclosed herein relate to the use of a compound of formula (I), or a pharmaceutically acceptable salt thereof, for the manufacture of a medicament useful for treatment of disorders ameliorated by modulation of $GABA_A$ α subunits other than α5 in an animal. In one embodiment, the modulation can be positive. In another embodiment, the modulation can be negative.

Some embodiments disclosed herein relate to a method of increasing cognitive function in an animal comprising administering to the animal an effective amount of a compound of formula (I), or a pharmaceutically acceptable salt thereof, under conditions wherein memory is increased. In one embodiment, the animal is healthy. In one embodiment, the memory is long term memory. In one embodiment, the memory is short term memory.

Some embodiments disclosed herein relate to the use of a compound of formula (I), or a cognitive function in an animal wherein the $GABA_A$ α5 subtype in the animal is negatively modulated. In pharmaceutically acceptable salt thereof, for the manufacture of a medicament for increasing one embodiment, the animal is healthy. In one embodiment, the memory is long term memory. In one embodiment, the memory is short term memory.

DETAILED DESCRIPTION OF THE INVENTION

Definitions

As used herein, common organic abbreviations are defined as follows:

Ac Acetyl aq. Aqueous

Bu n-Butyl
cat. Catalytic
CDI 1,1'-carbonyldiimidazole
° C. Temperature in degrees Centigrade
Dowtherm® eutectic mixture of diphenyl ether and biphenyl
DBN 1,5-Diazabicyclo[4.3.0]non-5-ene
DBU 1,8-Diazabicyclo[5.4.0]undec-7-ene
DIEA Diisopropylethylamine
DMA Dimethylacetamide
DMF N,N'-Dimethylformamide
DMSO Dimethylsulfoxide
Et Ethyl
g Gram(s)
h Hour (hours)
HPLC High performance liquid chromatography
iPr or isopr Isopropyl
LCMS Liquid chromatography-mass spectrometry
Me Methyl
MeOH Methanol
mL Milliliter(s)
Pd/C Palladium on activated carbon
ppt Precipitate
rt Room temperature
TEA Triethylamine
Tert, t tertiary
μL Microliter(s)

As used herein, the term "alkyl" refers to a fully saturated aliphatic hydrocarbon group. The alkyl moiety may be branched, straight chain, or cyclic. Examples of branched alkyl groups include, but are not limited to, isopropyl, sec-butyl, t-butyl and the like. Examples of straight chain alkyl groups include, but are not limited to, methyl, ethyl, propyl, butyl, pentyl, hexyl, heptyl, and the like. Examples of cyclic alkyl groups include, but are not limited to, cyclopropyl, cyclopentyl, cyclohexyl, cycloheptyl, and the like.

The term "alkoxy" used herein refers to straight or branched chain alkyl radical covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like.

The term "alkenyl" used herein refers to a monovalent straight or branched chain radical of from two to twenty carbon atoms containing a carbon double bond including, but not limited to, 1-propenyl, 2-propenyl, 2-methyl-1-propenyl, 1-butenyl, 2-butenyl, and the like.

The term "alkynyl" used herein refers to a monovalent straight or branched chain radical of from two to twenty carbon atoms containing a carbon triple bond including, but not limited to, 1-propynyl, 1-butynyl, 2-butynyl, and the like.

The term "aryl" used herein refers to homocyclic aromatic radical whether one ring or multiple fused rings. Moreover, the term "aryl" includes fused ring systems wherein at least two aryl rings, or at least one aryl and an ortho-fused bicyclic carbocyclic radical having about nine to ten ring atoms in which at least one ring is aromatic share at least one chemical bond. Examples of "aryl" rings include, but are not limited to, optionally substituted phenyl, biphenyl, naphthalenyl, phenanthrenyl, anthracenyl, tetralinyl, fluorenyl, indenyl, and indanyl.

The term, "heterocycle" or "heterocycle group" used herein refers to an optionally substituted monocyclic, bicyclic, or tricyclic ring system comprising at least one heteroatom in the ring system backbone. The heteroatoms are independently selected from oxygen, sulfur, and nitrogen. The term, "heterocycle" includes multiple fused ring systems. Moreover, the term "heterocycle" includes fused ring systems that may have any degree of saturation provided that at least one ring in the ring system is not aromatic. The monocyclic, bicyclic, or tricyclic ring system may be substituted or unsubstituted, and can be attached to other groups via any available valence, preferably any available carbon or nitrogen. Preferred monocyclic ring systems are of 4, 5, 6, 7, or 8 members. Six membered monocyclic rings contain from up to three heteroatoms wherein each heteroatom is individually selected from oxygen, sulfur, and nitrogen, and wherein when the ring is five membered, preferably it has one or two heteroatoms wherein each heteroatom is individually selected from oxygen, sulfur, and nitrogen. Preferred bicyclic cyclic ring systems are of 8 to 12 members and include spirocycles. An example of an optional substituent includes, but is not limited to, oxo (=O).

The term "heteroaryl" used herein refers to an aromatic heterocyclic group, whether one ring or multiple fused rings. In fused ring systems, the one or more heteroatoms may be present in only one of the rings. Examples of heteroaryl groups include, but are not limited to, benzothiazyl, benzoxazyl, quinazolinyl, quinolinyl, isoquinolinyl, quinoxalinyl, pyridyl, pyrrolyl, oxazolyl, indolyl, thienyl, and the like. The term "heterocycle" encompasses heteroaryl fused to a non-aromatic ring system.

The term "heteroatom" used herein refers to, for example, oxygen, sulfur and nitrogen.

The term "amino" used herein refers to a nitrogen radical substituted with hydrogen, alkyl, aryl, or combinations thereof. Examples of amino groups include, but are not limited to, —NHMethyl, —NH$_2$, —NMethyl$_2$, —NPhenylMethyl, —NHPhenyl, —NEthylMethyl, and the like.

The term "arylalkyl" used herein refers to one or more aryl groups appended to an alkyl radical. Examples of arylalkyl groups include, but are not limited to, benzyl, phenethyl, phenpropyl, phenbutyl, and the like.

The term "heteroarylalkyl" used herein refers to one or more heteroaryl groups appended to an alkyl radical. Examples of heteroarylalkyl include, but are not limited to, pyridylmethyl, furanylmethyl, thiopheneylethyl, and the like.

The term "aryloxy" used herein refers to an aryl radical covalently bonded to the parent molecule through an —O— linkage.

The term "alkylthio" used herein refers to straight or branched chain alkyl radical covalently bonded to the parent molecule through an —S— inkage.

The term "carbonyl" used herein refers to C=O (i.e. carbon double bonded to oxygen).

The term "oxo" used herein refers to =O (i.e. double bond to oxygen). For example, cyclohexane substituted with "oxo" is cyclohexanone.

The term "alkanoyl" used herein refers to a "carbonyl" substituted with an "alkyl" group, the "alkanoyl" group is covalently bonded to the parent molecule through the carbon of the "carbonyl" group. Examples of alkanoyl groups include, but are not limited to, methanoyl, ethanoyl, propanoyl, and the like. Methanoyl is commonly known as acetyl.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

As used herein, a substituted group is derived from the unsubstituted parent structure in which there has been an exchange of one or more hydrogen atoms for another atom or group.

Asymmetric carbon atoms may be present in the compounds described. All such isomers, including diastereomers and enantiomers, as well as the mixtures thereof are intended to be included in the scope of the recited compound. In certain cases, compounds can exist in tautomeric forms. All tautomeric forms are intended to be included in the scope. Likewise, when compounds contain an alkenyl or alkenylene group, there exists the possibility of cis- and trans-isomeric forms of the compounds. Both cis- and trans-isomers, as well as the mixtures of cis- and trans-isomers, are contemplated. Thus, reference herein to a compound includes all of the aforementioned isomeric forms unless the context clearly dictates otherwise.

Various forms are included in the embodiments, including polymorphs, solvates, hydrates, conformers, salts, and prodrug derivatives. A polymorph is a composition having the same chemical formula, but a different structure. A solvate is a composition formed by solvation (the combination of solvent molecules with molecules or ions of the solute). A hydrate is a compound formed by an incorporation of water. A conformer is a structure that is a conformational isomer. Conformational isomerism is the phenomenon of molecules with the same structural formula but different conformations (conformers) of atoms about a rotating bond. Salts of compounds can be prepared by methods known to those skilled in the art. For example, salts of compounds can be prepared by reacting the appropriate base or acid with a stoichiometric equivalent of the compound.

The term "animal" as used herein includes birds, reptiles, and mammals (e.g. domesticated mammals and humans).

The terms "individual," "host," "subject," and "patient" are used interchangeably herein, and refer to a mammal, including, but not limited to, murines, simians, humans, mammalian farm animals, mammalian sport animals, and mammalian pets.

Specific Embodiments

In one embodiment, the compound of formula (I) can be a compound of any of the formulae Ia-In.

Specific values listed below for radicals, substituents, and ranges, are for illustration only; they do not exclude other defined values or other values within defined ranges for the radicals and substituents.

In some embodiments, Ar can be phenyl, 4-methoxyphenyl, or 2-pyridyl, 4-chloro-2-pyridyl, 4-trifluoromethyl-phenyl, 3,5-bis(trifluoromethyl)-phenyl, 2,4-difluorophenyl, 2-fluorophenyl, 4-(1-methylethyl)phenyl or 4-chloro-2-fluorophenyl.

In some embodiments, Y can be O (oxygen) or S (sulfur).

The general methods to synthesize these compounds are detailed below.

Process of Preparation

Processes for preparing compounds of formula (I), is provided as further embodiments of the invention and are illustrated by the following procedures in which the meanings of the generic radicals are as given above unless otherwise qualified.

Compounds of the general formula (I) can be prepared using the general synthetic approach illustrated below in Scheme 1.

Scheme 1: General Reaction Scheme to N-alkyl-2-aryl-2,3-dihydrodipyrazolo[3,4-b:3',4'-d]pyridine-6(5H)-carboxamide

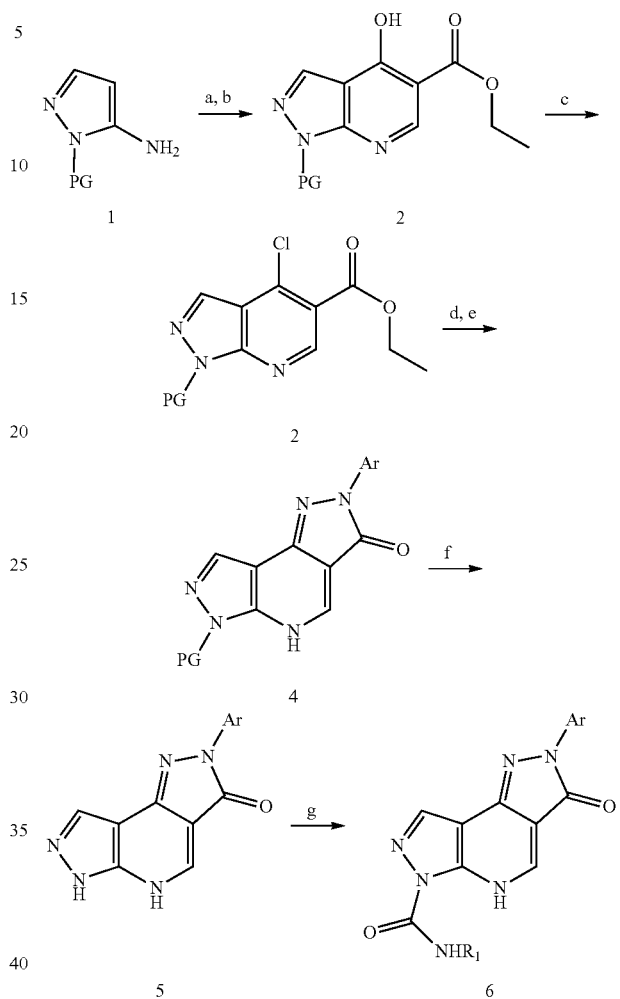

a) 1 equiv. diethyl-2-(ethoxymethylene)malonate, 125° C., 1 hrs,
b) Ph₂O, reflux, 30 min-3 hrs,
c) POCl₃, reflux, 1 hr,
d) 2 equiv. aryl or heteroaryl hydrazine, 2 equiv. triethylamine, ethanol, reflux, 2 hrs.
e) 5M aq. Sodium hydroxide, ethanol,
f) CF₃COOH, reflux, 40 minutes,
g) R₁-isocyanate or R₁-isothiocyanate (for thioureas), dimethylformamide, triethylamine, Ar and R₁ are defined as shown above with respect to formuls I, and PG is a protecting group and is known to those of skill in the art and can be found in references such as Greene and Wuts *Protective Groups in Organic Synthesis*; John Wiley and Sons: New York, 1999.

General Reaction Scheme 1 shows a representative synthetic method for the synthesis of N-alkyl-2-aryl-2,3-dihydrodipyrazolo[3,4-b:3',4'-d]pyridine-6(5H)-carboxamide. The 3-amino-pyrazole of formula 1 can be reacted with diethyl 2-(ethoxymethylene)malonate under heating to afford an enamine, in an addition-elimination type reaction, which upon thermal cyclization provides the hydroxy-pyrazolopyridine of formula 2. Solvents that can be used in step (b) include but are not limited to diphenyl ether, Dowtherm® and similar high boiling point stable solvents. Conversion of the hydroxyl-hydroxy-pyrazolopyridine of formula 2 to the chloro-pyrazolopyridine of formula 3 can be accomplished using a chlorinating agent in a halogenated solvent and optionally catalytic DMF. Chlorinating agents that can be used in step (c) include but are not limited to oxalyl chloride, P(O)Cl₃, PCl₅, thionyl chloride, phosgene, triphosgene, and similar chlorinating agents. Solvents that can be used in step (c) include but are not limited to chlorobenzene, methylene chloride, 1,2-dichloroethane, chloroform, and similar solvents. The chloro-pyrazolopyridine of formula 3 can be reacted with aryl or heteroaryl hydrazine followed by an alkaline cyclization to form the tricyclic dipyrazolopyridine of formula 4. Bases that can be used in step (d and e) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, sodium hydroxide and the like. Solvents that can be used in step (d and e) include but are not limited to o-xylene, xylenes, chlorobenzene, toluene, ethanol and the like. A reflux under acidic condition provides compound of formula 5. Acids that can be used in step (f) include but are not limited to trifluoroacetic acid, acetic acid, and the like. Step (f) can be performed with solvent or neat. Synthesis of final compound was achieved by reacting compound of formula 5 with alkyl isocyanates in the presence of base. Bases that can be used in step (g) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine and the like. Solvents that can be used in step (g) include but are not limited to chlorobenzene, methylene chloride, 1,2-dichloroethane, chloroform, dimethylformamide and similar solvents.

Additional ureas were prepared as shown in Scheme 2.

Scheme 2: General Reaction Scheme to N-alkyl-2-aryl-2,3-dihydrodipyrazolo[3,4-b:3′,4′-d]pyridine-6(5H)-carboxamide

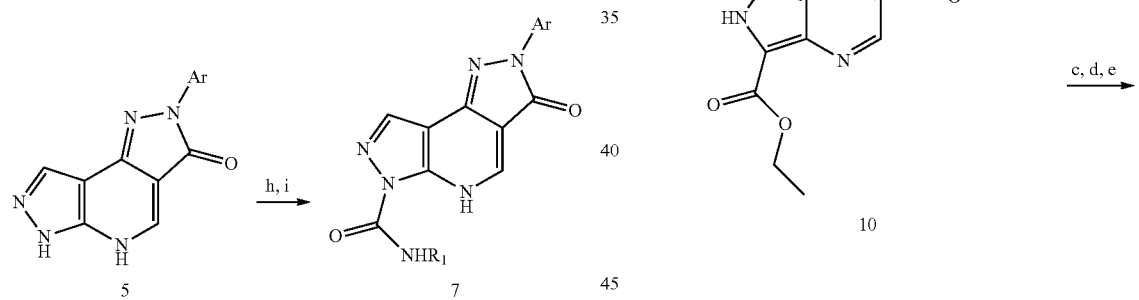

h) 1 equivalent triphosgene or isopropenylchloroformate, triethylamine, methylene chloride 0-37° C., 2 hrs,
i) R₁NH₂, methylene chloride, 0-37° C., 2-4 hrs, Ar and R₁ are defined as shown above with respect to formula I.

Synthesis of compound 7 was achieved in a two step single pot fashion by reacting compound of formula 5 with triphosgene in the presence of base followed by addition of alkyl amine. Bases that can be used in step (h and i) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine and the like. Solvents that can be used in step (h and i) include but are not limited to chlorobenzene, methylene chloride, 1,2-dichloroethane, chloroform, dimethylformamide and similar solvents.

General Reaction Scheme 3 shows a representative synthetic method for the synthesis of N-alkyl-2-aryl-3-oxo-2,3-dihydropyrazolo[3,4-d]pyrrolo[3,4-b]pyridine-7(5H)-carboxamide.

Scheme 3: General Reactions Scheme to N-alkyl-2-aryl-3-oxo-2,3-dihydropyrazolo[3,4-d]pyrrolo[3,4-b]pyridine-7(5H)-carboxamide

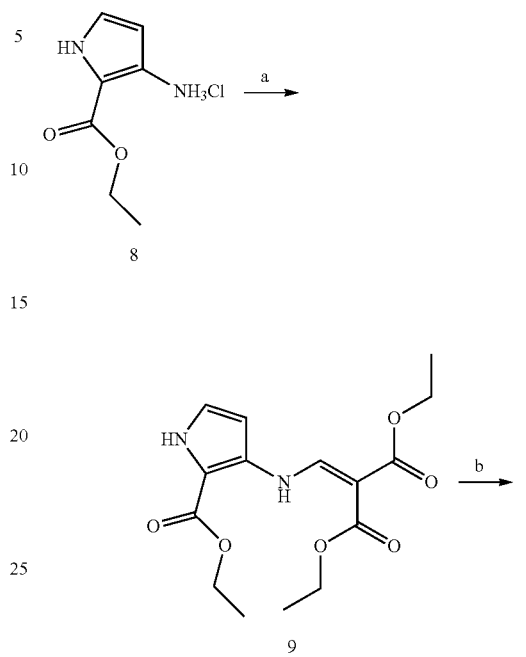

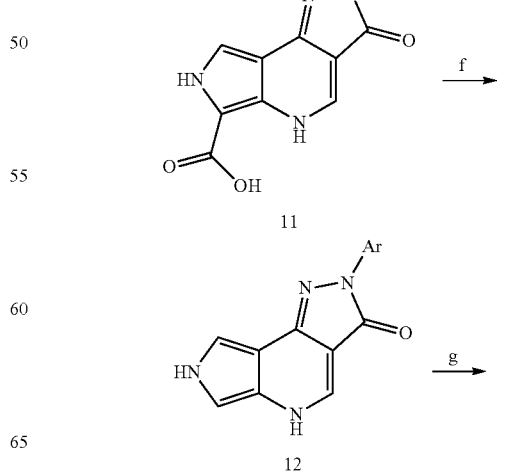

-continued

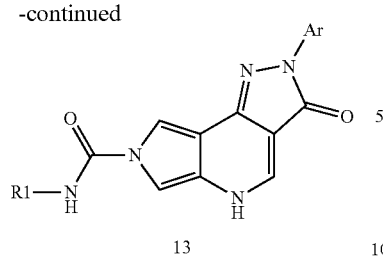

13 a) 1 equivalent diethyl 2-(ethoxymethylene)malonate, triethylamine, 100° C., 1 hrs,
b) POCl₃, 100° C., 30 min-3 hrs,
c) 2 equiv. aryl or heteroaryl hydrazine, ethanol, 75° C.,
d) 1N sodium hydroxide, 37° C.,
e) LiOH, 45° C.
f) dimethylformamide, 150° C.,
g) R₁-isocyanate or R₁-isothiocyanate (for thioureas), dimethylformamide, and triethylamine, Ar and R₁ are defined as shown above with respect to formula I.

The hydrochloride salt of 3-amino-pyrrole of Formula 8 can be reacted with diethyl 2-(ethoxymethylene)malonate under heating to afford an enamine of formula 9, in an addition-elimination type reaction in the presence of a base. Bases that can be used in step (a) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine and the like. The cyclization/chlorination in the presence of a chlorinating agent provides the chloro-pyrrolopyridine of formula 10. Chlorinating agents that can be used in step (c) include but are not limited to oxalyl chloride, P(O)Cl₃, PCl₅, thionyl chloride, phosgene, triphosgene, and similar chlorinating agents. The reaction can be done either neat or in the presence of a solvent. The chloro-pyrrolopyridine of formula 10 can be reacted with aryl or heteroaryl hydrazine followed by cyclization under basic conditions to form the tricyclic dipyrazolopyridine which was then hydrolyzed to yield dihydropyrazolo[3,4-d]pyrrolo[3,4-b]pyridine-carboxylate of formula 11. Bases that can be used in step (c, d and e) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, sodium hydroxide and the like. Solvents that can be used in step (c, d and e) include but are not limited to o-xylene, xylenes, chlorobenzene, toluene, ethanol and the like. Decarboxylation was achieved by refluxing compound of formula 11 in dimethylformamide. Synthesis of final compound of formula 13 was achieved by reacting compound of formula 12 with alkyl isocyanates in the presence of base. Bases that can be used in step (g) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine and the like. Solvents that can be used in step (g) include but are not limited to chlorobenzene, methylene chloride, 1,2-dichloroethane, chloroform, dimethylformaide and similar solvents.

General Reaction Scheme 4 shows a representative synthetic method for the synthesis of N-alkyl-2-aryl-3-oxo-2,3-dihydropyrazolo[3,4-d]pyrrolo[2,3-b]pyridine-7(5H)-carboxamide Scheme 4: General Reaction Scheme to N-alkyl-2-aryl-3-oxo-2,3-dihydropyrazolo[3,4-d]pyrrolo[2,3-b]pyridine-7(5H)-carboxamide

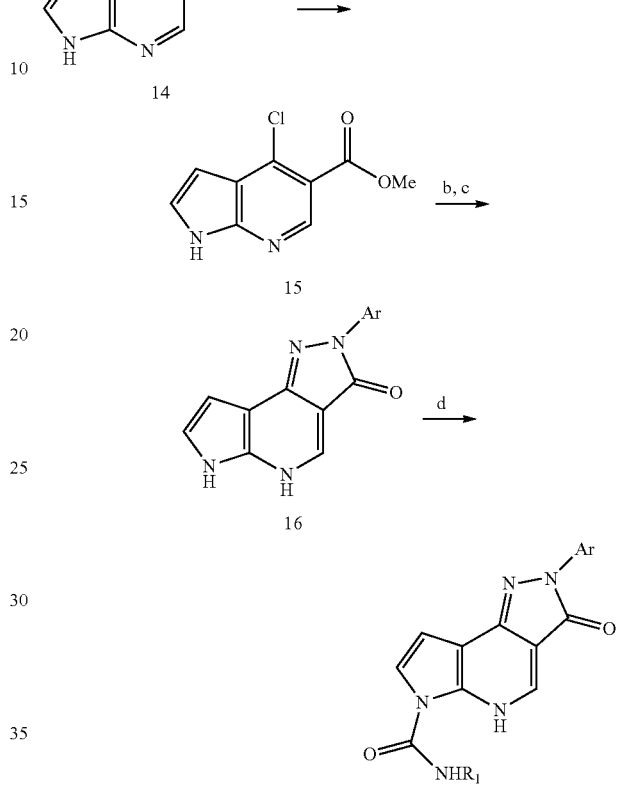

a) Oxalyl chloride, methanol,
b) aryl or heteroaryl hydrazine, ethanol, 75° C,
c) 1N sodium hydroxide, methanol,
d) R₁-isocyanate or R₁-isothiocyanate (for thioureas), dimethylformamide, and triethylamine, Ar and R₁ are defined as shown above with respect to formula I.

Commercially available carboxylic acid was esterified using a one pot two step procedure of in situ generation of acid chloride followed by a methanol quench. Chlorinating agents that can be used in step (a) include but are not limited to oxalyl chloride, P(O)Cl₃, PCl₅, thionyl chloride, phosgene, triphosgene, and similar chlorinating agents. The chloro-pyrrolopyridine of formula 15 can be reacted with aryl or heteroaryl hydrazine followed by cyclization under neutral or basic conditions followed a base catalyzed cyclization to form the tricyclic dipyrrolopyridine of formula 16. Bases that can be used in step (b and c) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, sodium hydroxide and the like. Solvents that can be used in step (b and c) include but are not limited to o-xylene, xylenes, chlorobenzene, toluene, ethanol and the like. Synthesis of final compound of formula 17 was achieved by reacting compound of formula 16 with alkyl isocyanates in the presence of base. Bases that can be used in step (d) include but are not limited to triethyl amine (TEA), diisopropylethyl amine (DIEA), 1,8-Diazabicyclo[5.4.0]undec-7-ene (DBU), 1,5-Diazabicyclo

[4.3.0]non-5-ene (DBN), N-methylpiperidine and the like. Solvents that can be used in step (d) include but are not limited to chlorobenzene, methylene chloride, 1,2-dichloroethane, chloroform, dimethylformaide and similar solvents.

Scheme 5: General Reaction Scheme to N-alkyl-7-aryl-6-oxo-6,7-dihydropyrazolo[4,3-b:3',4'-d]pyridine-2(4H)-carboxamide

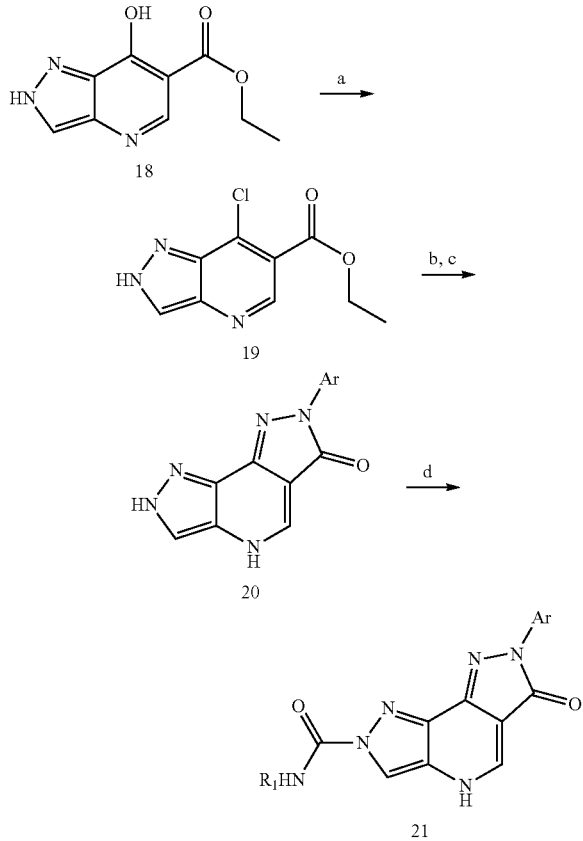

a) Oxalyl chloride, catalytic DMF, chloroform, reflux, 3 h.,
b) aryl or heteroaryl hydrazine, ethanol, 75° C.,
c) 1N sodium hydroxide, methanol,
d) R₁-isocyanate or R₁-isothiocyanate (for thioureas), dimethylformamide, and triethylamine, Ar and R₁ are defined as shown above with respect to formula I.

Conversion of compound 18 to compound 19 can be accomplished using a chlorinating agent in a halogenated solvent and optionally catalytic DMF. Chlorinating agents that can be used in step (a) include but are not limited to oxalyl chloride, P(O)Cl₃, PCl₅, thionyl chloride, phosgene, triphosgene, and similar chlorinating agents. Solvents that can be used in step (a) include but are not limited to chlorobenzene, methylene chloride, 1,2-dichloroethane, chloroform, and similar solvents. For example, compound 18 was reacted with oxalyl chloride in the presence of catalytic DMF in chloroform under reflux for 3 h to afford compound 19.

Compound 19 can be reacted with aryl or heteroaryl hydrazine followed by an alkaline cyclization to form the tricyclic dipyrazolopyridine of formula 20. Bases that can be used in step (b and c) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine, sodium hydroxide and the like. Solvents that can be used in step (b and c) include but are not limited to o-xylene, xylenes, chlorobenzene, toluene, ethanol and the like. Synthesis of final compound of formula 21 is achieved by reacting compound of formula 20 with R₁-isocyanate or R₁-isothiocyanate in the presence of base. Bases that can be used in step (d) include but are not limited to triethyl amine (TEA), diisopropylethyl amine (DIEA), 1,8-Diazabicyclo[5.4.0]undec-7-ene (DBU), 1,5-Diazabicyclo[4.3.0]non-5-ene (DBN), N-methylpiperidine and the like. Solvents that can be used in step (d) include but are not limited to chlorobenzene, methylene chloride, 1,2-dichloroethane, chloroform, dimethylformamide and similar solvents.

General Procedures: Scheme 1 (Compounds 6a-6az)

Step 1:

Ethyl 1-(4-methoxybenzyl)-4-oxo-4,7-dihydro-1H-pyrazolo[3,4-b]pyridine-5-carboxylate (2)

Equimolar amounts of compound 1 and dimethylmethoxy malonate were heated to 100° C. for 16 h. Nitrogen gas was bubbled through the reaction mixture overnight to yield enamine as brown solid which was added to a preheated flask at 245° C. and stirred at that temperature for 45 minutes. The reaction mixture was cooled to room temperature and collected solid was washed repeatedly to yield product 2 as off white solid.

Step 2:

Ethyl 4-chloro-1-(4-methoxybenzyl)-1H-pyrazolo[3,4-b]pyridine-5-carboxylate (3)

Ethyl 1-(4-methoxybenzyl)-4-oxo-4,7-dihydro-1H-pyrazolo[3,4-b]pyridine-5-carboxylate 2 and POCl₃ were heated at 80° C. in a sealed tube for 3 hours. Reaction mixture was concentrated in vacuo, diluted with diethylether, washed with water, dried over sodium sulfate and concentrated in vacuo to afford product 3 as off white solid.

Step 3:

6-(4-methoxybenzyl)-2-phenyl-5,6-dihydrodipyrazolo[3,4-b:3',4'-d]pyridin-3(2H)-one (4)

A suspension of compound 3 and 10 equivalents of phenyl hydrazine was stirred at 90° C. for 16 hours. Reaction was quenched with iced water. The aqueous layer was removed, residue was suspended in ethanol and stirred with 1N NaOH solution at room temperature for 1 hour. pH was adjusted to 5 using acetic acid and solvent was removed in vacuo. Compound 4 was collected by filtration.

Step 4:

2-phenyl-5,6-dihydrodipyrazolo[3,4-b:3',4'-d]pyridin-3(2H)-one.TFA (5a)

Compound 4 was suspended in trifluoroacetic acid and stirred at 100° C. for 40 minutes in a microwave. Excess acid was removed in vacuo. Yellow precipitates were collected, washed with methanol and dried to afford product 5a.

Step 5:

Example 1

N-isopropyl-3-oxo-2-phenyl-2,3-dihydrodipyrazolo[3,4-b:3',4'-d]pyridine-6(5H)-carboxamide (6a)

One equivalent of compound 5a, 1.5 equivalents of triethylamine and 1.2 equivalents of iso-propylisocyanate were suspended in DMF and stirred at room temperature for 15 hours. Solvent was removed in vacuo and the compound was purified using column chromatography to yield product 6a as yellow solid. $^1$H NMR (400 MHz, DMSO-d$_6$) δ ppm 1.26 (d, J=6.60 Hz, 7H), 4.04 (dq, J=14.12, 6.79 Hz, 1H), 7.17 (t, J=7.34 Hz, 1H), 7.44 (t, J=7.89 Hz, 2H), 8.11 (d, J=8.07 Hz, 2H), 8.41 (d, J=8.44 Hz, 1H), 8.56 (s, 1H), 8.97 (s, 1H).

Example 2

N-ethyl-3-oxo-2-phenyl-2,3-dihydrodipyrazolo[3,4-b:3',4'-d]pyridine-6(5H)-carboxamide (6b)

Compound 6b was synthesized following step 5 using compound 5a and ethylisocyanate instead of iso-propylisocyanate. $^1$H NMR (400 MHz, DMSO-d6) δ ppm 1.16 (t, J=7.15 Hz, 3H), 3.32-3.38 (m, 2H), 7.10-7.18 (m, 1H), 7.41 (t, J=7.89 Hz, 2H), 8.09 (d, J=8.07 Hz, 2H), 8.53 (s, 1H), 8.65 (t, J=5.69 Hz, 1H), 8.93 (s, 1H).

Example 3

N-butyl-3-oxo-2-phenyl-2,3-dihydrodipyrazolo[3,4-b:3',4'-d]pyridine-6(5H)-carboxamide.TFA (6f)

Compound 6f was synthesized following step 5 using compound 5a and butylisocyanate instead of iso-propylisocyanate. $^1$H NMR (400 MHz, DMSO-d6) δppm 0.89 (t, J=7.24 Hz, 3H), 1.32 (sxt, J=7.28 Hz, 2H), 1.55 (quin, J=7.24 Hz, 2H), 3.23-3.33 (m, 3H), 7.14 (t, J=7.24 Hz, 1H), 7.41 (t, J=7.63 Hz, 2H), 8.09 (d, J=8.22 Hz, 2H), 8.48-8.56 (m, 1H), 8.58-8.67 (m, 1H), 8.94 (s, 1H), 13.01 (d, J=5.87 Hz, 1H).

Example 4

3-oxo-N,2-diphenyl-2,3-dihydrodipyrazolo[3,4-b:3',4'-d]pyridine-6(5H)-carboxamide (6h)

Compound 6h was synthesized following step 5 using compound 5a and phenylisocyanate instead of iso-propylisocyanate. $^1$H NMR (400 MHz, DMSO-d6) δ ppm 7.17 (d, J=12.47 Hz, 2H), 7.41 (q, J=7.58 Hz, 5H), 7.74 (d, J=8.07 Hz, 2H), 8.09 (d, J=8.44 Hz, 2H), 8.54 (s, 1H), 9.10 (s, 1H), 10.55 (s, 1H).

Example 5

N-ethyl-3-oxo-2-(pyridin-2-yl)-2,3-dihydrodipyrazolo[3,4-b:3',4'-d]pyridine-6(5H)-carboxamide (6m)

Compound 6m was synthesized following step 4 and 5a using compound 4a and pyridylhydrazine and ethylisocyanate instead of phenylhydrazine and iso-propylisocyanante respectively. $^1$H NMR (400 MHz, DMSO-d6) δppm 1.13-1.19 (m, 3H), 3.31-3.39 (m, 3H), 7.17-7.24 (m, 1H), 7.83-7.91 (m, 1H), 8.14 (d, J=8.44 Hz, 1H), 8.46 (d, J=4.40 Hz, 1H), 8.55 (s, 1H), 8.61-8.70 (m, 1H), 8.93 (s, 1H).

Example 6

2-(4-chlorophenyl)-5,6-dihydrodipyrazolo[3,4-b:3',4'-d]pyridin-3(2H)-one.TFA (6o)

Compound 6o was synthesized following step 4 and 5a using compound 4a and 4-chloro-phenylhydrazine and ethylisocyanate instead of phenylhydrazine and iso-propylisocyanante respectively. $^1$H NMR (400 MHz, DMSO-d6) δppm 1.15 (t, J=7.04 Hz, 3H), 7.47 (d, J=9.00 Hz, 2H), 8.13 (d, J=9.00 Hz, 2H) 8.56 (s, 1H), 8.66 (t, J=5.87 Hz, 1H), 8.90-8.98 (m, 1H), 13.03-13.14 (m, 1H).

Example 7

2-(5-chloropyridin-2-yl)-N-ethyl-3-oxo-2,3-dihydrodipyrazolo[3,4-b:3',4'-d]pyridine-6(5H)-carboxamide (6ay)

Compound 6ay was synthesized following step 4 and 5a using compound 4a and 4-chloro-2-pyridylhydrazine and ethylisocyanate instead of phenylhydrazine and iso-propylisocyanante respectively. 1H NMR (400 MHz, DMSO-d6) δppm 1.15 (t, J=7.24 Hz, 3H), 3.08 (q, J=7.04 Hz, 2H), 7.99 (dd, J=8.80, 2.54 Hz, 1H), 8.24 (d, J=9.00 Hz, 1H), 8.49 (d, J=2.35 Hz, 1H), 8.58 (s, 1H), 8.67 (br. s., 1H), 8.95 (s, 1H), 13.11 (br. s., 1H).

Example 8

2-(4-bromophenyl)-N-ethyl-3-oxo-2,3-dihydrodipyrazolo[3,4-b:3',4'-d]pyridine-6(5H)-carboxamide.TFA (6w)

Compound 6w was synthesized following step 4 and 5a using compound 4a and 4-bromophenylhydrazine and ethylisocyanate instead of phenylhydrazine and iso-propylisocyanante respectively. 1H NMR (400 MHz, DMSO-d6) δppm 1.16 (t, J=7.24 Hz, 3H), 3.27-3.37 (m, 2H), 7.60 (d, J=9.00 Hz, 2H), 8.08 (d, J=9.00 Hz, 2H), 8.57 (d, J=5.87 Hz, 1H), 8.66 (t, J=5.87 Hz, 1H), 8.95 (s, 1H), 13.10 (d, J=5.09 Hz, 1H).

Example 9

N-ethyl-2-(4-isopropylphenyl)-3-oxo-2,3-dihydrodipyrazolo[3,4-b:3',4'-d]pyridine-6(5H)-carboxamide. TFA (6z)

Compound 6z was synthesized following step 4 and 5a using compound 4a and 4-bromophenylhydrazine and ethylisocyanate instead of phenylhydrazine and iso-propylisocyanante respectively. $^1$H NMR (400 MHz, DMSO-d6) δppm 1.09-1.26 (m, 10H), 2.82-2.94 (m, 1H), 3.32 (d, J=7.04 Hz, 3H), 7.28 (d, J=8.61 Hz, 2H), 7.97 (d, J=8.22 Hz, 2H), 8.51 (d, J=5.87 Hz, 1H), 8.65 (t, J=5.67 Hz, 1H), 8.93 (s, 1H), 12.98 (d, J=5.48 Hz, 1H).

General Procedure: Scheme 2 (7a-7c)

Example 10

N,N-dimethyl-3-oxo-2-phenyl-2,3-dihydrodipyrazolo[3,4-b:3',4'-d]pyridine-6(5H)-carboxamide. TFA (7c)

A suspension of 5a and 1.2 equivalents of isopropenyl chloroformate in dichloroethane was treated with 1.2 equivalents of diisopropyl ethylamine (0.177 mL, 1.07 mmol). After 15 h stirring at room temperature, 2M dimethylamine in THF (0.196 mL, 0.392 mmol) was added and allowed to stir at room temperature for 18 h. Solvents were removed in vacuo and residue was purified on HPLC. The product was obtained as yellow solids. $^1$H NMR (400 MHz, DMSO-d6) δppm 3.12 (br. s., 6H), 7.14 (t, J=7.24 Hz, 1H), 7.41 (t, J=8.61 Hz, 3H), 8.09 (d, J=7.83 Hz, 2H), 8.54 (d, J=5.87 Hz, 1H), 8.90 (s, 1H), 13.17 (d, J=5.48 Hz, 1H).

General Procedures: Scheme 3 (Compounds 13a-13k)

Step 1:

Diethyl 2-((2-(ethoxycarbonyl)-1H-pyrrol-3-ylamino)methylene)malonate (9a)

Equimolar ratios of ethyl 3-methyl-1H-pyrrole-2-carboxylate hydrochloride, diisopropylethylamine and diethyl ethoxymethylenemalonate were mixed in a sealed tube and heated at 100° C. for 15 hours. After cooling to room temperature, column chromatography afforded the title compound as a white solid.

Step 2:

Diethyl 4-chloro-6H-pyrrolo[3,4-b]pyridine-3,7-dicarboxylate (10a)

Diethyl 2-((2-(ethoxycarbonyl)-1H-pyrrol-3-ylamino)methylene)malonate was dissolved in phosphoryl chloride (0.2 M) and heated at 75° C. for 18 hours. Reaction mixture was concentrated to dryness and water and ethyl acetate were added. The aqueous layer was extracted with ethylacetate, the combined organic fractions were washed with brine and dried over magnesium sulfate before concentrating in vacuo to afford the crude compound 10a as an orange solid.

Step 3:

Ethyl 3-oxo-2-phenyl-2,3,5,7-tetrahydropyrazolo[3,4-d]pyrrolo[3,4-b]pyridine-6-carboxylate One equivalent of crude diethyl 4-chloro-6H-pyrrolo[3,4-b]pyridine-3,7-dicarboxylate was dissolved in ethanol (0.2 M) under an atmosphere of nitrogen. Following the addition of 2 equivalents of triethylamine and 1.2 equivalents of phenyl hydrazine, the reaction was heated at 75° C. for 21 hours. After cooling to room temperature a large excess of 1 N NaOH was added and after 5 hours the reaction was concentrated to dryness. 10% HCl (aq.) was added and the brown precipitate was collected by filtration and washed with methylene chloride to afford the product as a yellow solid. $^1$H NMR (400 MHz, DMSO-d6) δ ppm 1.35 (br. s., 3H) 4.23-4.52 (m, 2H) 6.96-7.22 (m, 1H) 7.26-7.54 (m, 2H) 7.64-7.89 (m, 1H) 7.99-8.27 (m, 3H) 11.60-11.89 (m, 1H) 13.04-13.29 (m, 1H).

3-Oxo-2-phenyl-2,3,5,7-tetrahydropyrazolo[3,4-d]pyrrolo[3,4-b]pyridine-6-carboxylic acid (11a)

Ethyl 3-oxo-2-phenyl-2,3,5,7-tetrahydropyrazolo[3,4-d]pyrrolo[3,4-b]pyridine-6-carboxylate was dissolved into a mixture of methanol, THF and $H_2O$ (1:1:1, 0.2 M). LiOH (5 eq.) was added and the reaction was heated at 45° C. for 17 hours. After cooling to room temperature the reaction was concentrated to dryness. 10% HCl (aq.) was added and the precipitate was collected, affording the title compound as a brown solid. $^1$H NMR (400 MHz, DMSO-d6) δ ppm 6.87-7.21 (m, 1H) 7.25-7.52 (m, 2H) 7.60-7.85 (m, 1H) 8.13 (br. s., 3H) 11.56-11.92 (m, 1H) 12.90-13.17 (m, 1H)

Step 4:

2-Phenyl-5,7-dihydropyrazolo[3,4-d]pyrrolo[3,4-b]pyridin-3(2H)-one (12a)

3-Oxo-2-phenyl-2,3,5,7-tetrahydropyrazolo[3,4-d]pyrrolo[3,4-b]pyridine-6-carboxylic acid was dissolved in DMF (0.3 M) and heated at 220° C. in a microwave for 20 minutes. The crude reaction mixture was concentrated and column chromatography afforded the title compound as a brown solid. $^1$H NMR (400 MHz, DMSO-d6) δ ppm 7.07 (t, J=4.4 Hz, 1H) 7.14 (s, 1H) 7.36 (t, J=4.4 Hz, 2H) 7.44 (s, 1H) (8.15 (d, J=7.6 Hz, 1H) 8.29 (d, J=6.4 Hz 1H) 12.06 (s, 1H) 12.34 (s, 1H).

Step 5:

Example 11

N-Methyl-3-oxo-2-phenyl-2,3-dihydropyrazolo[3,4-d]pyrrolo[3,4-b]pyridine-7(5H)-carboxamide (13a)

One equivalent of pyrrolo-pyridine 12a was dissolved in DMF (0.1 M) under an atmosphere of nitrogen. 3 equivalents of di-iso-propylethylamine was added, followed by 1.5 equivalents of methylisocyanate and stirred overnight. The crude reaction mixture was concentrated to dryness and purification by column chromatography afforded the compound 13a. $^1$H NMR (400 MHz, DMSO-d6) δ ppm 2.84 (d, J=3.52 Hz, 3H) 7.02-7.18 (m, 1H) 7.30-7.47 (m, 2H) 7.57-7.78 (m, 1H) 7.90-8.04 (m, 1H) 8.05-8.20 (m, 2H) 8.32-8.50 (m, 1H) 8.52-8.68 (m, 1H) 12.28-12.49 (m, 1H)

Example 12

N-Ethyl-3-oxo-2-phenyl-2,3-dihydropyrazolo[3,4-d]pyrrolo[3,4-b]pyridine-7(5H)-carboxamide (13b)

The title compound 13b was obtained following procedure described above in step 5 by using ethylisocyanate instead of methylisocyanate. $^1$H NMR (400 MHz, DMSO-d6) δ ppm 1.00-1.35 (m, 3H) 7.02-7.19 (m, 1H) 7.33-7.46 (m, 2H) 7.60-7.71 (m, 1H) 7.99-8.07 (m, 1H) 8.07-8.18 (m, 2H) 8.36-8.48 (m, 1H) 8.59-8.72 (m, 1H) 12.33-12.47 (m, 1H)

Example 13

3-Oxo-2-phenyl-N-propyl-2,3-dihydropyrazolo[3,4-d]pyrrolo[3,4-b]pyridine-7(5H)-carboxamide (13c)

Following procedure described in step 5 and using n-propyl isocyanate afforded the title compound 13c as a yellow solid. $^1$H NMR (400 MHz, DMSO-d6) δ ppm 0.81-1.00 (m, 3H) 1.42-1.76 (m, 2H) 3.15-3.26 (m, 2H) 7.00-7.24 (m, 1H) 7.26-7.49 (m, 2H) 7.51-7.73 (m, 1H) 7.97-8.20 (m, 3H) 8.33-8.52 (m, 1H) 8.54-8.71 (m, 1H) 12.27-12.50 (m, 1H).

Example 14

N-Butyl-3-oxo-2-phenyl-2,3-dihydropyrazolo[3,4-d]pyrrolo[3,4-b]pyridine-7(5H)-carboxamide (13i)

Following procedure described in step 5 and using n-butyl isocyanate afforded the title compound 13i as a yellow solid. $^1$H NMR (400 MHz, DMSO-d6) δ ppm 0.78-0.99 (m, 3H) 1.22-1.42 (m, 2H) 1.46-1.66 (m, 2H) 6.98-7.17 (m, 1H) 7.25-7.45 (m, 2H) 7.54-7.73 (m, 1H) 7.97-8.21 (m, 3H) 8.30-8.49 (m, 1H) 8.52-8.70 (m, 1H) 12.30-12.49 (m, 1H)

Example 15

N-Isopropyl-3-oxo-2-phenyl-2,3-dihydropyrazolo[3,4-d]pyrrolo[3,4-b]pyridine-7(5H)-carboxamide (13j)

Following procedure described in step 5 and using isopropyl isocyanate afforded the title compound 13j as a yellow solid. $^1$H NMR (400 MHz, DMSO-d6) δ ppm 1.21 (d, J=6.65

Hz, 8H) 3.86-4.07 (m, 1H) 7.00-7.16 (m, 1H) 7.29-7.47 (m, 2H) 7.58-7.70 (m, 1H) 7.99-8.22 (m, 3H) 8.30-8.49 (m, 2H) 12.27-12.47 (m, 1H).

Example 16

3-Oxo-N,2-diphenyl-2,3-dihydropyrazolo[3,4-d]pyrrolo[3,4-b]pyridine-7(5H)-carboxamide (13k)

Following procedure described in step 5 and using phenyl isocyanate afforded the title compound 13k as a yellow solid. $^1$H NMR (400 MHz, DMSO-d6) δ ppm 7.01-7.24 (m, 2H) 7.31-7.49 (m, 4H) 7.62-7.75 (m, 2H) 7.73-7.88 (m, 1H) 8.05-8.19 (m, 2H) 8.19-8.33 (m, 1H) 8.37-8.52 (m, 1H) 10.27-10.48 (m, 1H) 12.34-12.53 (m, 1H).

Example 17

N-Ethyl-2-(2-fluorophenyl)-3-oxo-2,3-dihydropyrazolo[3,4-d]pyrrolo[3,4-b]pyridine-7(5H)-carboxamide (13d)

Compound 13d was obtained following procedures described in steps 3, 4 and 5 and using 2-fluorophenyl hydrazine and ethylisocyanate instead of phenyl hydrazine and methylisocyanate respectively. $^1$H NMR (400 MHz, DMSO-d6) δ ppm 1.15 (d, J=2.35 Hz, 3H) 7.12-7.43 (m, 3H) 7.43-7.59 (m, 1H) 7.60-7.72 (m, 1H) 7.83-8.01 (m, 1H) 8.27-8.51 (m, 1H) 8.54-8.73 (m, 1H) 12.17-12.48 (m, 1H)

Example 18

N-Ethyl-2-(4-fluorophenyl)-3-oxo-2,3-dihydropyrazolo[3,4-d]pyrrolo[3,4-b]pyridine-7(5H)-carboxamide (13f)

Compound 13f was obtained following procedures described in steps 3, 4 and 5 and using 4-fluorophenyl hydrazine and ethylisocyanate instead of phenyl hydrazine and methylisocyanate respectively. $^1$H NMR (400 MHz, DMSO-d6) δ ppm 1.05-1.29 (m, 3H) 7.13-7.32 (m, 2H) 7.55-7.70 (m, 1H) 7.96-8.06 (m, 1H) 8.06-8.18 (m, 2H) 8.34-8.53 (m, 1H) 8.57-8.75 (m, 1H) 12.32-12.53 (m, 1H).

Example 19

2-(2,4-Difluorophenyl)-N-ethyl-3-oxo-2,3-dihydropyrazolo[3,4-d]pyrrolo[3,4-b]pyridine-7(5H)-carboxamide (13g)

Compound 13g was obtained following procedures described in steps 3, 4 and 5 and using 2,4-difluorophenyl hydrazine and ethylisocyanate instead of phenyl hydrazine and methylisocyanate respectively. $^1$H NMR (400 MHz, DMSO-d6) δ ppm 0.97-1.24 (m, 3H) 7.05-7.25 (m, 1H) 7.33-7.48 (m, 1H) 7.48-7.61 (m, 1H) 7.61-7.73 (m, 1H) 7.80-8.02 (m, 1H) 8.29-8.55 (m, 1H) 8.51-8.76 (m, 1H) 12.27-12.54 (m, 1H).

General Procedures: Scheme 4 (Compounds 17a-17f)
Step 1:

Methyl 4-chloro-1H-pyrrolo[2,3-b]pyridine-5-carboxylate (15)

To a solution of carboxylic acid 14 in methylene chloride under an atmosphere of nitrogen was added 1.5 equivalents of oxalyl chloride followed by catalytic amount of dimethylformamide. The reaction was stirred for 18 hours before the addition of an excess of methanol. After 2 hours stirring the reaction was evaporated to dryness to give the title compound 15 as an off-white solid. $^1$H NMR (400 MHz, DMSO-d6) δ ppm 3.87 (s, 3H) 6.62-6.63 (m, 1H) 7.68-7.69 (m, 1H) 8.68-8.70 (m, 1H) 12.37 (s, 1H).

Step 2:

2-Phenyl-5,6-dihydropyrazolo[3,4-d]pyrrolo[2,3-b]pyridin-3(2H)-one (16)

A suspension of 1 equivalent of compound 15 and 10 equivalents of phenyl hydrazine was heated to 90° C. for 16 hours. Water was added to the reaction mixture at room temperature and decanted to remove the excess phenyl hydrazine. The crude reaction mixture was dissolved in MeOH and 0.1 N NaOH (2:1, 0.033 M) and stirred for 3.5 hours before concentrating to dryness. Purification by column chromatography afforded the title compound 16 as a yellow solid. $^1$H NMR (400 MHz, DMSO-d6) δ ppm 6.43-6.72 (m, 1H) 7.04-7.28 (m, 1H) 7.37-7.56 (m, 4H) 7.84-8.13 (m, 2H) 8.33-8.55 (m, 1H) 11.99 (s, 1H).

Step 3:

Example 20

N-Methyl-3-oxo-2-phenyl-2,3-dihydropyrazolo[3,4-d]pyrrolo[2,3-b]pyridine-6(5H)-carboxamide (17a)

A solution of pyrrolo-pyridine 16 in dimethylformamide under an atmosphere of nitrogen and 3 equivalents of di-isopropylethylamine (3 eq.) was added 3 equivalents of methylisocyanate and stirred overnight. The crude reaction mixture was concentrated to dryness and purification by column chromatography afforded the title compound 17a. $^1$H NMR (400 MHz, DMSO-d6) δ ppm 2.83-3.11 (m, 3H) 6.64-6.92 (m, 1H) 7.21-7.43 (m, 1H) 7.44-7.63 (m, 2H) 7.77-8.05 (m, 3H) 8.57-8.81 (m, 1H) 9.48-9.76 (m, 1H).

Example 21

N-Ethyl-3-oxo-2-phenyl-2,3-dihydropyrazolo[3,4-d]pyrrolo[2,3-b]pyridine-6(5H)-carboxamide (17b)

The title compound 17b was obtained following procedure described above in step 3 by using ethylisocyanate instead of methylisocyanate. $^1$H NMR (400 MHz, DMSO-d6) δ ppm 1.22 (br. s., 4H) 3.38-3.51 (m, 3H) 6.63-6.89 (m, 1H) 7.17-7.39 (m, 1H) 7.44-7.67 (m, 2H) 7.78-8.03 (m, 3H) 8.59-8.80 (m, 1H) 9.62-9.88 (m, 1H) 12.23-12.44 (m, 1H).

Example 22

N-Isopropyl-3-oxo-2-phenyl-2,3-dihydropyrazolo[3,4-d]pyrrolo[2,3-b]pyridine-6(5H)-carboxamide (17c)

The title compound 17c was obtained following procedure described above in step 3 by using iso-propylisocyanate instead of methylisocyanate. $^1$H NMR (400 MHz, DMSO-d6) δ ppm 1.22-1.44 (m, 7H) 3.90-4.18 (m, 1H) 6.71-6.87 (m, 1H) 7.18-7.37 (m, 1H) 7.44-7.62 (m, 2H) 7.78-8.03 (m, 3H) 8.58-8.79 (m, 1H) 9.61-9.81 (m, 1H) 12.24-12.43 (m, 1H)

Example 23

3-Oxo-N,2-diphenyl-2,3-dihydropyrazolo[3,4-d]pyrrolo[2,3-b]pyridine-6(5H)-carboxamide (17d)

The title compound 17d was obtained following procedure described above in step 3 by using phenylisocyanate instead of methylisocyanate. $^1$H NMR (400 MHz, DMSO-d6) δ ppm 6.80-6.95 (m, 1H) 7.13-7.25 (m, 1H) 7.25-7.37 (m, 1H) 7.39-7.49 (m, 2H) 7.49-7.64 (m, 2H) 7.66-7.79 (m, 2H) 7.84-7.97 (m, 2H) 7.98-8.11 (m, 1H) 8.72-9.01 (m, 1H) 12.13-12.35 (m, 1H).

Example 24

N-ethyl-3-oxo-2-phenyl-2,3-dihydropyrazolo[3,4-d]pyrrolo[2,3-b]pyridine-6(5H)-carbothioamide (17e)

To a solution of pyrrolo-pyridine 16 in dimethylformamide under an atmosphere of nitrogen and 3 equivalents of di-isopropylethylamine (3 eq.) was added 3 equivalents of ethylisothiocyanate. The reaction mixture was stirred in a microwave at 100° C. for 3 hours. The crude reaction mixture was concentrated in vacuo and purified by column chromatography to afford compound 17e. $^1$H NMR (400 MHz, DMSO-d6) δ ppm 1.22-1.42 (m, 3H) 3.68-3.93 (m, 2H) 6.72-6.90 (m, 1H) 7.19-7.38 (m, 1H) 7.42-7.64 (m, 2H) 7.77-7.96 (m, 2H) 8.27-8.59 (m, 1H) 8.61-8.81 (m, 1H) 12.10-12.38 (m, 1H) 12.37-12.57 (m, 1H).

Example 25

2-(5-Chloropyridin-2-yl)-N-ethyl-3-oxo-2,3-dihydropyrazolo[3,4-d]pyrrolo[2,3-b]pyridine-6(5H)-carboxamide (17f)

Compound 17f was obtained following procedures described in steps (2 and 3) and using 4-chloro-2-pyridylhydrazine and ethylisocyanate instead of phenyl hydrazine and methylisocyanate respectively. $^1$H NMR (400 MHz, DMSO-d6) δ ppm 1.09-1.30 (m, 3H) 3.38-3.54 (m, 2H) 6.83-7.00 (m, 1H) 7.73-7.96 (m, 1H) 8.04-8.20 (m, 1H) 8.48-8.66 (m, 2H) 8.65-8.78 (m, 1H) 9.66-9.86 (m, 1H) 13.14-13.35 (m, 1H).

Example 26

N-methyl-3-oxo-2-phenyl-2,3-dihydrodipyrazolo[3,4-b:3',4'-d]pyridine-6(5H)-carboxamide (6c)

Compound 6c can be obtained following procedures described herein. $^1$H NMR (400 MHz, DMSO-$d_6$) δ ppm 2.86-2.91 (m, 3H) 7.16 (d, J=6.65 Hz, 1H) 7.39-7.47 (m, 2H) 8.07-8.13 (m, 2H) 8.52-8.57 (m, 2H) 8.95 (d, J=4.70 Hz, 1H) 13.06 (br. s., 1H).

Example 27

3-oxo-2-phenyl-N-propyl-2,3-dihydrodipyrazolo[3,4-b:3',4'-d]pyridine-6(5H)-carboxamide (6d)

Compound 6d can be obtained following procedures described herein. $^1$H NMR (400 MHz, DMSO-$d_6$) δ ppm 0.88 (t, J=7.24 Hz, 3H) 1.48-1.64 (m, 2H) 3.26 (q, J=6.52 Hz, 2H) 7.14 (t, J=7.43 Hz, 1H) 7.41 (t, J=7.83 Hz, 2H) 8.08 (d, J=8.22 Hz, 1H) 8.53 (d, J=5.09 Hz, 1H) 8.63 (t, J=5.87 Hz, 1H) 8.94 (s, 1H) 13.02 (d, J=5.09 Hz, 1H).

Example 28

N-isobutyl-3-oxo-2-phenyl-2,3-dihydrodipyrazolo[3,4-b:3',4'-d]pyridine-6(5H)-carboxamide (6e)

Compound 6e can be obtained following procedures described herein. $^1$H NMR (400 MHz, DMSO-$d_6$) δ=13.01 (br. s., 1H), 8.93 (s, 1H), 8.75-8.43 (m, 2H), 8.08 (d, J=7.8 Hz, 2H), 7.41 (t, J=8.0 Hz, 2H), 7.14 (t, J=7.4 Hz, 1H), 1.73-1.50 (m, 1H), 0.90 (d, J=6.3 Hz, 6H).

Example 29

N-isopentyl-3-oxo-2-phenyl-2,3-dihydrodipyrazolo[3,4-b:3',4'-d]pyridine-6(5H)-carboxamide (6g)

Compound 6g can be obtained following procedures described herein. $^1$H NMR (400 MHz, DMSO-$d_6$) δ=13.01 (br. s., 1H), 8.93 (s, 1H), 8.71-8.43 (m, 2H), 8.08 (d, J=7.8 Hz, 2H), 7.41 (t, J=8.0 Hz, 2H), 7.14 (t, J=7.4 Hz, 1H), 1.75-1.35 (m, 3H), 0.90 (d, J=6.3 Hz, 7H).

Example 30

2-(5-chloropyridin-2-yl)-N-ethyl-3-oxo-2,3-dihydrodipyrazolo[3,4-b:3',4'-d]pyridine-6(5H)-carboxamide (6i)

Compound 6i can be obtained following procedures described herein. $^1$H NMR (400 MHz, DMSO-$d_6$) δ ppm 1.15 (t, J=7.24 Hz, 3H) 3.08 (q, J=7.04 Hz, 2H) 7.99 (dd, J=8.80, 2.54 Hz, 1H) 8.24 (d, J=9.00 Hz, 1H) 8.49 (d, J=2.35 Hz, 1H) 8.58 (s, 1H) 8.67 (br. s., 1H) 8.95 (s, 1H) 13.11 (br. s., 1H).

Example 31

N-(2-(dimethylamino)ethyl)-3-oxo-2-phenyl-2,3-dihydrodipyrazolo[3,4-b:3',4'-d]pyridine-6(5H)-carboxamide (7a)

Compound 7a can be obtained following procedures described herein. $^1$H NMR (400 MHz, DMSO-$d_6$) δ=9.93 (d, J=5.1 Hz, 1H), 8.61-8.44 (m, 1H), 8.33 (s, 1H), 8.30-8.09 (m, 3H), 7.36-7.25 (m, 2H), 7.07-6.94 (m, 1H), 3.53-3.44 (m, 1H), 3.14 (dd, J=6.5, 12.7 Hz, 1H), 2.59-2.48 (m, 2H), 2.31-2.18 (m, 6H).

Example 32

3-oxo-2-phenyl-N-(2,2,2-trifluoroethyl)-2,3-dihydrodipyrazolo[3,4-b:3',4'-d]pyridine-6(5H)-carboxamide (7b)

Compound 7b can be obtained following procedures described herein. $^1$H NMR (400 MHz, DMSO-$d_6$) δ=13.05 (br. s., 1H), 9.34-9.13 (m, 1H), 9.04 (s, 1H), 8.56 (s, 1H), 8.08 (d, J=8.2 Hz, 2H), 7.52-7.00 (m, 3H), 4.25-3.94 (m, 2H).

Example 33

6-(4-isopropylpiperazine-1-carbonyl)-2-phenyl-5,6-dihydrodipyrazolo[3,4-b:3',4'-d]pyridin-3(2H)-one (7d)

Compound 7d can be obtained following procedures described herein. $^1$H NMR (400 MHz, DMSO-$d_6$) δ ppm 1.25

(d, J=6.24 Hz, 6H) 7.11-7.18 (m, 1H) 7.42 (t, J=7.52 Hz, 2H) 8.08 (d, J=8.07 Hz, 2H) 8.56 (s, 1H) 8.95 (s, 1H).

Example 34

N-cyclopropyl-3-oxo-2-phenyl-2,3-dihydrodipyrazolo[3,4-b:3',4'-d]pyridine-6(5H)-carboxamide (6j)

Compound 6j can be obtained following procedures described herein. $^1$H NMR (400 MHz, DMSO-$d_6$) δ ppm 0.72 (d, J=5.48 Hz, 4H) 2.81 (d, J=4.30 Hz, 1H) 7.08-7.16 (m, 1H) 7.40 (t, J=7.83 Hz, 2H) 8.11 (d, J=8.22 Hz, 2H) 8.47 (s, 1H) 8.73 (d, J=3.52 Hz, 1H) 8.86 (s, 1H).

Example 35

2-phenyl-6-(pyrrolidine-1-carbonyl)-5,6-dihydrodipyrazolo[3,4-b:3',4'-d]pyridin-3(2H)-one (6k)

Compound 6k can be obtained following procedures described herein. $^1$H NMR (400 MHz, DMSO-$d_6$) δ ppm 1.86-1.92 (m, 4H) 3.58 (br. S., 4H) 7.13 (t, J=7.43 Hz, 1H) 7.41 (t, J=7.83 Hz, 2H) 8.08 (d, J=8.22 Hz, 2H) 8.54 (d, J=5.09 Hz, 1H) 8.92 (s, 1H).

Example 36

N-ethyl-8-methyl-3-oxo-2-phenyl-2,3-dihydrodipyrazolo[3,4-b:3',4'-d]pyridine-6(5H)-carboxamide (6l)

Compound 6l can be obtained following procedures described herein. $^1$H NMR (400 MHz, DMSO-$d_6$) δ ppm 1.14 (t, J=7.24 Hz, 3H) 2.96 (s, 3H) 3.25-3.31 (m, 2H) 7.13 (t, J=7.24 Hz, 1H) 7.40 (t, J=7.83 Hz, 2H) 8.10 (d, J=7.83 Hz, 2H) 8.46 (s, 1H) 12.80 (br. s., 1H).

Example 37

N-isopropyl-3-oxo-2-(pyridin-2-yl)-2,3-dihydrodipyrazolo[3,4-b:3',4'-d]pyridine-6(5H)-carboxamide (6n)

Compound 6n can be obtained following procedures described herein. $^1$H NMR (400 MHz, DMSO-$d_6$) δ ppm 1.24 (d, J=6.60 Hz, 6H) 4.01 (dt, J=13.66, 6.92 Hz, 1H) 7.21 (dd, J=6.97, 5.14 Hz, 1H) 7.85-7.90 (m, 1H) 8.14 (d, J=8.07 Hz, 1H) 8.46 (d, J=4.77 Hz, 1H) 8.55 (s, 1H) 8.93 (s, 1H).

Example 38

2-(4-chlorophenyl)-N-isopropyl-3-oxo-2,3-dihydrodipyrazolo[3,4-b:3',4'-d]pyridine-6(5H)-carboxamide (6p)

Compound 6p can be obtained following procedures described herein. $^1$H NMR (400 MHz, DMSO-$d_6$) δ ppm 1.22 (d, J=6.60 Hz, 6H) 4.01 (dt, J=13.66, 6.92 Hz, 1H) 7.47 (d, J=9.00 Hz, 2H) 8.13 (d, J=9.00 Hz, 2H) 8.39 (d, J=8.89 Hz, 1H) 8.56 (s, 1H) 8.94 (s, 1H) 13.0 (br.s., 1H).

Example 39

2-(3,5-bis(trifluoromethyl)phenyl)-N-ethyl-3-oxo-2,3-dihydrodipyrazolo[3,4-b:3',4'-d]pyridine-6(5H)-carboxamide (6q)

Compound 6q can be obtained following procedures described herein. $^1$H NMR (400 MHz, DMSO-$d_6$) δ ppm 1.16 (t, J=7.04 Hz, 3H) 7.84 (s, 1H) 8.63-8.71 (m, 2H) 8.79 (s, 2H) 9.08 (s, 1H) 13.31 (br. s., 1H).

Example 40

2-(3,5-bis(trifluoromethyl)phenyl)-N-isopropyl-3-oxo-2,3-dihydrodipyrazolo[3,4-b:3',4'-d]pyridine-6(5H)-carboxamide (6r)

Compound 6r can be obtained following procedures described herein. $^1$H NMR (400 MHz, DMSO-$d_6$) δ ppm 1.24 (d, J=6.65 Hz, 6H) 3.96-4.07 (m, 1H) 7.85 (s, 1H) 8.41 (d, J=8.22 Hz, 1H) 8.66 (s, 1H) 8.79 (s, 2H) 9.08 (s, 1H) 13.25 (br. s., 1H).

Example 41

2-(4-chloro-3-(trifluoromethyl)phenyl)-N-ethyl-3-oxo-2,3-dihydrodipyrazolo[3,4-b:3',4'-d]pyridine-6(5H)-carboxamide (6s)

Compound 6s can be obtained following procedures described herein. $^1$H NMR (400 MHz, DMSO-$d_6$) δ ppm 1.17 (t, J=7.19 Hz, 3H) 3.34 (quin, J=6.67 Hz, 2H) 7.79 (d, J=8.90 Hz, 1H) 8.43 (d, J=8.90 Hz, 1H) 8.64 (br. s., 2H) 8.68 (t, J=5.82 Hz, 1H) 9.02 (s, 1H).

Example 42

2-(4-chloro-3-(trifluoromethyl)phenyl)-N-isopropyl-3-oxo-2,3-dihydrodipyrazolo[3,4-b:3',4'-d]pyridine-6(5H)-carboxamide (6t)

Compound 6t can be obtained following procedures described herein. $^1$H NMR (400 MHz, DMSO-$d_6$) δ ppm 1.24 (d, J=6.65 Hz, 6H) 4.01 (dq, J=13.50, 6.72 Hz, 1H) 7.78 (d, J=8.61 Hz, 1H) 8.36-8.45 (m, 2H) 8.62 (d, J=1.96 Hz, 2H) 9.02 (s, 1H) 13.16 (br. s., 1H).

Example 43

N-ethyl-3-oxo-2-(thiophen-3-yl)-2,3-dihydrodipyrazolo[3,4-b:3',4'-d]pyridine-6(5H)-carboxamide (6u)

Compound 6u can be obtained following procedures described herein. $^1$H NMR (400 MHz, DMSO-$d_6$) δ=9.00-8.78 (m, 1H), 8.74-8.38 (m, 1H), 7.78-7.47 (m, 1H), 7.35 (d, J=4.7 Hz, 1H), 7.19-6.66 (m, 1H), 5.70 (br. s., 1H), 3.17-3.04 (m, 2H), 1.32-1.01 (m, 3H).

Example 44

N-isopropyl-3-oxo-2-(thiophen-3-yl)-2,3-dihydrodipyrazolo[3,4-b:3',4'-d]pyridine-6(5H)-carboxamide (6v)

Compound 6v can be obtained following procedures described herein. $^1$H NMR (400 MHz, DMSO-$d_6$) δ=8.92 (s, 1H), 8.54 (s, 1H), 8.39 (d, J=8.2 Hz, 1H), 7.80-7.62 (m, 1H), 7.57 (dd, J=3.3, 5.3 Hz, 1H), 7.40-7.29 (m, 1H), 7.11 (s, 1H), 6.79 (d, J=8.6 Hz, 1H), 4.00-3.99 (m, 1H), 1.23 (d, J=6.7 Hz, 6H).

Example 45

2-(4-bromophenyl)-N-isopropyl-3-oxo-2,3-dihydrodipyrazolo[3,4-b:3',4'-d]pyridine-6(5H)-carboxamide (6x)

Compound 6x can be obtained following procedures described herein. $^1$H NMR (400 MHz, DMSO-$d_6$) δ ppm 1.23 (d, J=6.65 Hz, 6H) 3.96-4.06 (m, 1H) 7.60 (d, J=9.00 Hz, 2H) 8.08 (d, J=9.00 Hz, 2H) 8.39 (d, J=8.22 Hz, 1H) 8.57 (d, J=5.87 Hz, 1H) 8.95 (s, 1H) 13.03 (d, J=5.48 Hz, 1H).

Example 46

2-(4-bromophenyl)-N-methyl-3-oxo-2,3-dihydrodipyrazolo[3,4-b:3',4'-d]pyridine-6(5H)-carboxamide (6y)

Compound 6y can be obtained following procedures described herein. $^1$H NMR (400 MHz, DMSO-$d_6$) δ ppm 2.87 (d, J=4.30 Hz, 3H) 7.60 (d, J=8.61 Hz, 2H) 8.08 (d, J=8.61 Hz, 2H) 8.56 (br. s., 2H) 8.94 (s, 1H) 13.13 (br. s., 1H).

Example 47

N-isopropyl-2-(4-isopropylphenyl)-3-oxo-2,3-dihydrodipyrazolo[3,4-b:3',4'-d]pyridine-6(5H)-carboxamide (6aa)

Compound 6aa can be obtained following procedures described herein. $^1$H NMR (400 MHz, DMSO-$d_6$) δ ppm 1.22 (dd, J=13.30, 6.65 Hz, 12H) 2.83-2.92 (m, 1H) 3.96-4.06 (m, 1H) 7.28 (d, J=8.61 Hz, 2H) 7.97 (d, J=8.61 Hz, 2H) 8.37 (d, J=8.22 Hz, 1H) 8.51 (d, J=5.87 Hz, 1H) 8.94 (s, 1H) 12.92 (d, J=5.48 Hz, 1H).

Example 48

2-(3-chlorophenyl)-N-methyl-3-oxo-2,3-dihydrodipyrazolo[3,4-b:3',4'-d]pyridine-6(5H)-carboxamide (6ab)

Compound 6ab can be obtained following procedures described herein. $^1$H NMR (400 MHz, DMSO-$d_6$) δ ppm 2.87 (d, J=4.70 Hz, 3H) 7.19 (dd, J=7.83, 1.17 Hz, 1H) 7.45 (t, J=8.22 Hz, 1H) 8.07-8.12 (m, 1H) 8.21 (t, J=1.96 Hz, 1H) 8.54-8.58 (m, 2H) 8.96 (s, 1H) 13.17 (br. s., 1H).

Example 49

N-butyl-2-(3-chlorophenyl)-3-oxo-2,3-dihydrodipyrazolo[3,4-b:3',4'-d]pyridine-6(5H)-carboxamide (6ac)

Compound 6ac can be obtained following procedures described herein. $^1$H NMR (400 MHz, DMSO-$d_6$) δ ppm 0.89 (t, J=7.43 Hz, 3H) 1.32 (sxt, J=7.36 Hz, 2H) 1.55 (quin, J=7.24 Hz, 2H) 3.25-3.29 (m, 2H) 7.19 (dd, J=7.83, 1.57 Hz, 1H) 7.45 (t, J=8.22 Hz, 1H) 8.10 (d, J=8.22 Hz, 1H) 8.20 (t, J=1.96 Hz, 1H) 8.58 (s, 1H) 8.63 (t, J=6.06 Hz, 1H) 8.97 (s, 1H) 13.12 (br. s., 1H).

Example 50

2-(3-chlorophenyl)-N-ethyl-3-oxo-2,3-dihydrodipyrazolo[3,4-b:3',4'-d]pyridine-6(5H)-carboxamide (6ad)

Compound 6ad can be obtained following procedures described herein. $^1$H NMR (400 MHz, DMSO-$d_6$) δ ppm 1.16 (t, J=7.04 Hz, 3H) 3.34-3.40 (m, 2H) 7.19 (dd, J=7.83, 1.17 Hz, 1H) 7.45 (t, J=8.22 Hz, 1H) 8.07-8.12 (m, 1H) 8.21 (t, J=1.96 Hz, 1H) 8.58 (s, 1H) 8.67 (t, J=5.87 Hz, 1H) 8.97 (s, 1H) 13.13 (br. s., 1H).

Example 51

N-ethyl-3-oxo-2-(4-(trifluoromethyl)phenyl)-2,3-dihydrodipyrazolo[3,4-b:3',4'-d]pyridine-6(5H)-carboxamide (6ae)

Compound 6ae can be obtained following procedures described herein. $^1$H NMR (400 MHz, Methanol-$d_4$) δ=8.86 (s, 1H), 8.45 (s, 1H), 8.24 (d, J=8.2 Hz, 2H), 7.67 (d, J=8.6 Hz, 2H), 4.57 (br. s., 2H), 1.23 (t, J=7.0 Hz, 3H).

Example 52

N-isopropyl-3-oxo-2-(4-(trifluoromethyl)phenyl)-2,3-dihydrodipyrazolo[3,4-b:3',4'-d]pyridine-6(5H)-carboxamide (6af)

Compound 6af can be obtained following procedures described herein. $^1$H NMR (400 MHz, DMSO-$d_6$) δ=9.93 (d, J=5.1 Hz, 1H), 8.61-8.44 (m, 1H), 8.33 (s, 1H), 8.30-8.09 (m, 3H), 7.36-7.25 (m, 2H), 7.07-6.94 (m, 1H), 3.53-3.44 (m, 1H), 3.14 (dd, J=6.5, 12.7 Hz, 1H), 2.59-2.48 (m, 2H), 2.31-2.18 (m, 6H).

Example 53

N-methyl-3-oxo-2-(4-(trifluoromethyl)phenyl)-2,3-dihydrodipyrazolo[3,4-b:3',4'-d]pyridine-6(5H)-carboxamide (6ag)

Compound 6ag can be obtained following procedures described herein. $^1$H NMR (400 MHz, DMSO-$d_6$) δ=9.10 (s, 1H), 8.42 (s, 1H), 7.88 (d, J=8.6 Hz, 1H), 7.50 (d, J=8.6 Hz, 1H), 7.22 (d, J=8.6 Hz, 1H), 6.85 (d, J=8.6 Hz, 1H), 5.66 (s, 1H), 3.68 (s, 3H).

Example 54

N-butyl-3-oxo-2-(4-(trifluoromethyl)phenyl)-2,3-dihydrodipyrazolo[3,4-b:3',4'-d]pyridine-6(5H)-carboxamide (6ah)

Compound 6ah can be obtained following procedures described herein. $^1$H NMR (400 MHz, DMSO-$d_6$) δ=13.17 (br. s., 1H), 8.99 (s, 1H), 8.74-8.53 (m, 2H), 8.37 (d, J=8.6 Hz, 2H), 7.81 (d, J=9.0 Hz, 2H), 1.69-1.15 (m, 4H), 1.09-0.73 (m, 3H).

Example 55

N-ethyl-3-oxo-2-(3-(trifluoromethyl)phenyl)-2,3-dihydrodipyrazolo[3,4-b:3',4'-d]pyridine-6(5H)-carboxamide (6ai)

Compound 6ai can be obtained following procedures described herein. $^1$H NMR (400 MHz, DMSO-$d_6$) δ ppm 1.16 (t, J=7.04 Hz, 3H) 3.35-3.38 (m, 2H) 7.49 (d, J=7.43 Hz, 1H) 7.67 (t, J=8.02 Hz, 1H) 8.44 (d, J=8.61 Hz, 1H) 8.48 (s, 1H) 8.59 (s, 1H) 8.67 (t, J=5.87 Hz, 1H) 9.01 (s, 1H) 13.16 (br. s., 1H).

Example 56

N-butyl-3-oxo-2-(3-(trifluoromethyl)phenyl)-2,3-dihydrodipyrazolo[3,4-b:3',4'-d]pyridine-6(5H)-carboxamide (6aj)

Compound 6aj can be obtained following procedures described herein. $^1$H NMR (400 MHz, DMSO-$d_6$) δ ppm 0.89 (t, J=7.24 Hz, 3H) 1.32 (sxt, J=7.36 Hz, 2H) 1.55 (quin, J=7.24 Hz, 2H) 3.25-3.29 (m, 2H) 7.49 (d, J=7.83 Hz, 1H) 7.67 (t, J=8.02 Hz, 1H) 8.44 (d, J=8.22 Hz, 1H) 8.47 (s, 1H) 8.59 (s, 1H) 8.64 (t, J=5.87 Hz, 1H) 9.01 (s, 1H) 13.16 (br. s., 1H).

Example 57

N-butyl-2-(4-chloro-2-fluorophenyl)-3-oxo-2,3-dihydrodipyrazolo[3,4-b:3',4'-d]pyridine-6(5H)-carboxamide (6ak)

Compound 6ak can be obtained following procedures described herein. $^1$H NMR (400 MHz, DMSO-$d_6$) δ=13.04 (br. s., 1H), 8.90 (s, 1H), 8.69-8.49 (m, 2H), 7.65-7.52 (m, 2H), 7.38 (d, J=8.6 Hz, 1H), 1.54 (quin, J=7.2 Hz, 2H), 1.39-1.24 (m, 2H), 0.89 (t, J=7.4 Hz, 3H).

Example 58

N-butyl-2-(2-fluorophenyl)-3-oxo-2,3-dihydrodipyrazolo[3,4-b:3',4'-d]pyridine-6(5H)-carboxamide (6al)

Compound 6al can be obtained following procedures described herein. $^1$H NMR (400 MHz, DMSO-$d_6$) δ=8.85 (s, 1H), 8.66 (t, J=5.9 Hz, 1H), 8.50 (s, 1H), 7.60-7.21 (m, 4H), 3.06 (q, J=7.0 Hz, 2H), 1.54 (quin, J=7.2 Hz, 2H), 1.39-1.24 (m, 2H), 0.89 (t, J=7.4 Hz, 3H)

Example 59

N-butyl-2-(2-fluorophenyl)-3-oxo-2,3-dihydrodipyrazolo[3,4-b:3',4'-d]pyridine-6(5H)-carboxamide (6am)

Compound 6am can be obtained following procedures described herein. $^1$H NMR (400 MHz, DMSO-$d_6$) δ=8.88 (s, 1H), 8.66 (t, J=5.9 Hz, 1H), 8.52 (s, 1H), 7.60-7.21 (m, 4H), 3.06 (q, J=7.0 Hz, 2H), 1.15 (d, J=1.6 Hz, 3H).

Example 60

N-butyl-2-(2,4-difluorophenyl)-3-oxo-2,3-dihydrodipyrazolo[3,4-b:3',4'-d]pyridine-6(5H)-carboxamide (6an)

Compound 6an can be obtained following procedures described herein. $^1$H NMR (400 MHz, DMSO-$d_6$) δ=9.14-8.96 (m, 1H), 8.91-8.78 (m, 1H), 8.60 (d, J=14.1 Hz, 1H), 7.20 (dd, J=8.0, 11.5 Hz, 1H), 7.08-6.94 (m, 1H), 6.90-6.72 (m, 1H), 1.65-1.31 (m, 3H), 0.98-0.79 (m, 6H).

Example 61

2-(2,4-difluorophenyl)-N-ethyl-3-oxo-2,3-dihydrodipyrazolo[3,4-b:3',4'-d]pyridine-6(5H)-carboxamide (6ao)

Compound 6ao can be obtained following procedures described herein. $^1$H NMR (400 MHz, DMSO-$d_6$) δ=12.99 (br. s., 1H), 8.88 (s, 1H), 8.73-8.45 (m, 2H), 7.66-7.08 (m, 4H), 1.15 (t, J=7.0 Hz, 3H).

Example 62

2-(2,4-difluorophenyl)-N-isopentyl-3-oxo-2,3-dihydrodipyrazolo[3,4-b:3',4'-d]pyridine-6(5H)-carboxamide (6ap)

Compound 6ap can be obtained following procedures described herein. $^1$H NMR (400 MHz, DMSO-$d_6$) δ=12.98 (br. s., 1H), 8.88 (s, 1H), 8.67-8.47 (m, 2H), 7.58-7.48 (m, 1H), 7.44-7.23 (m, 3H), 1.65-1.52 (m, 1H), 1.46 (q, J=7.0 Hz, 2H), 0.90 (d, J=6.7 Hz, 6H).

Example 63

2-(2,4-difluorophenyl)-N-isobutyl-3-oxo-2,3-dihydrodipyrazolo[3,4-b:3',4'-d]pyridine-6(5H)-carboxamide (6aq)

Compound 6aq can be obtained following procedures described herein. $^1$H NMR (400 MHz, DMSO-$d_6$) δ=12.97 (br. s., 1H), 8.89 (s, 1H), 8.62 (t, J=5.9 Hz, 1H), 8.52 (s, 1H), 7.55-7.49 (m, 1H), 7.40-7.35 (m, 1H), 7.31-7.26 (m, 1H), 3.12 (t, J=6.5 Hz, 2H), 1.91 (td, J=6.7, 13.6 Hz, 1H), 0.88 (d, J=6.7 Hz, 6H).

Example 64

N-ethyl-3-oxo-2-phenyl-2,3-dihydrodipyrazolo[3,4-b:3',4'-d]pyridine-6(5H)-carbothioamide (6ar)

Compound 6ar can be obtained following procedures described herein. $^1$H NMR (400 MHz, DMSO-$d_6$) δ=10.43 (br. s., 1H), 9.21 (br. s., 1H), 8.53 (br. s., 1H), 8.08 (d, J=6.7 Hz, 2H), 7.41 (br. s., 2H), 7.14 (br. s., 1H), 3.72 (br. s., 2H), 1.22 (br. s., 3H).

Example 65

2-(4-chlorophenyl)-N-ethyl-3-oxo-2,3-dihydrodipyrazolo[3,4-b:3',4'-d]pyridine-6(5H)-carbothioamide (6as)

Compound 6as can be obtained following procedures described herein. $^1$H NMR (400 MHz, DMSO-$d_6$) δ=13.25-12.90 (m, 1H), 10.60-10.29 (m, 1H), 9.35-9.05 (m, 1H), 8.69-8.43 (m, 1H), 8.26-7.97 (m, 2H), 7.64-7.27 (m, 2H), 3.85-3.62 (m, 2H), 1.39-1.06 (m, 3H).

Example 66

2-(4-bromophenyl)-N-ethyl-3-oxo-2,3-dihydrodipyrazolo[3,4-b:3',4'-d]pyridine-6(5H)-carbothioamide (6at)

Compound 6at can be obtained following procedures described herein. $^1$H NMR (400 MHz, DMSO-$d_6$) δ=10.60-10.25 (m, 1H), 9.37-9.09 (m, 1H), 8.68-8.42 (m, 1H), 8.23-7.92 (m, 2H), 7.75-7.45 (m, 2H), 3.83-3.59 (m, 2H), 1.45-1.00 (m, 3H).

Example 67

N-ethyl-2-(4-isopropylphenyl)-3-oxo-2,3-dihydrodipyrazolo[3,4-b:3',4'-d]pyridine-6(5H)-carbothioamide (6au)

Compound 6au can be obtained following procedures described herein. $^1$H NMR (400 MHz, DMSO-$d_6$) δ=13.12-

12.85 (m, 1H), 10.57-10.32 (m, 1H), 9.31-9.08 (m, 1H), 8.64-8.31 (m, 1H), 8.13-7.78 (m, 2H), 7.46-6.99 (m, 2H), 3.88-3.58 (m, 2H), 3.01-2.74 (m, 1H), 1.20 (d, J=6.3 Hz, 9H).

Example 68

N-ethyl-8-methyl-3-oxo-2-phenyl-2,3-dihydrodipyrazolo[3,4-b:3',4'-d]pyridine-7(5H)-carboxamide (6av)

Compound 6av can be obtained following procedures described herein. $^1$H NMR (400 MHz, DMSO-$d_6$) δ ppm 1.15 (t, J=7.04 Hz, 3H) 2.62 (s, 3H) 3.27 (d, J=3.91 Hz, 2H) 7.15 (t, J=7.43 Hz, 1H) 7.42 (t, J=7.83 Hz, 2H) 8.10-8.17 (m, 2H) 8.76 (br. s., 1H) 12.63 (br. s., 1H).

Example 69

2-(5-chloropyridin-2-yl)-N-isopropyl-3-oxo-2,3-dihydrodipyrazolo[3,4-b:3',4'-d]pyridine-6(5H)-carboxamide (6aw)

Compound 6aw can be obtained following procedures described herein. $^1$H NMR (400 MHz, DMSO-$d_6$) δ ppm 1.24 (d, J=6.65 Hz, 6H) 3.96-4.07 (m, 1H) 7.99 (d, J=8.61 Hz, 1H) 8.23 (d, J=8.61 Hz, 1H) 8.38 (d, J=7.04 Hz, 1H) 8.49 (br. s., 1H) 8.59 (br. s., 1H) 8.96 (s, 1H) 13.02 (br. s., 1H).

Example 70

2-(5-chloropyridin-2-yl)-N-methyl-3-oxo-2,3-dihydrodipyrazolo[3,4-b:3',4'-d]pyridine-6(5H)-carboxamide (6ax)

Compound 6ax can be obtained following procedures described herein. $^1$H NMR (400 MHz, DMSO-$d_6$) δ ppm 2.87 (d, J=4.70 Hz, 3H) 7.99 (d, J=8.61 Hz, 1H) 8.23 (d, J=8.61 Hz, 1H) 8.38 (d, J=7.04 Hz, 1H) 8.49 (br. s., 1H) 8.59 (br. s., 1H) 8.96 (s, 1H) 13.1 (br. s., 1H).

Example 71

2-(4-bromophenyl)-N-methyl-3-oxo-2,3-dihydrodipyrazolo[3,4-b:3',4'-d]pyridine-6(5H)-carboxamide (6az)

Compound 6az can be obtained following procedures described herein. $^1$H NMR (400 MHz, DMSO-$d_6$) δ ppm 2.87 (d, J=4.30 Hz, 3H) 7.60 (d, J=8.61 Hz, 2H) 8.08 (d, J=8.61 Hz, 2H) 8.56 (br. s., 2H) 8.94 (s, 1H) 13.13 (br. s., 1H).

Example 72

N-butyl-2-(2-fluorophenyl)-3-oxo-2,3-dihydropyrazolo[3,4-d]pyrrolo[3,4-b]pyridine-7(5H)-carboxamide (13e)

Compound 13e can be obtained following procedures described herein. $^1$H NMR (400 MHz, DMSO-$d_6$) δ=8.71-8.49 (m, 1H), 8.49-8.27 (m, 1H), 8.06-7.79 (m, 1H), 7.73-7.58 (m, 1H), 7.58-7.47 (m, 1H), 7.44-6.99 (m, 3H), 3.28-3.19 (m, J=5.9 Hz, 2H), 1.61-1.43 (m, 2H), 1.43-1.17 (m, 2H), 1.01-0.55 (m, 3H).

Example 73

2-(5-chloropyridin-2-yl)-N-ethyl-3-oxo-2,3-dihydropyrazolo[3,4-d]pyrrolo[3,4-b]pyridine-7(5H)-carboxamide (13h)

Compound 13h can be obtained following procedures described herein. $^1$H NMR (400 MHz, DMSO-$d_6$) δ=12.53-12.43 (m, 1H), 8.70-8.60 (m, 1H), 8.50-8.41 (m, 1H), 8.20-8.11 (m, 2H), 8.08-7.97 (m, 1H), 7.72-7.63 (m, 1H), 7.51-7.37 (m, 1H), 3.31 (s, 2H), 1.24-1.09 (m, 3H).

Biological Examples

The ability of a compound disclosed herein to act as ligand to the benzodiazepine site of $GABA_A$ can be determined using pharmacological models which are well known in the art using the following assay. The $IC_{50}$ values for the exemplified compounds range from sub nM to 10 μM in a 3-concentration dose response curve.

Binding assay 1: Whole brain (except cerebellum) of male Wistar derived rats weighing 175±25 g were used to prepare $GABA_A$ central benzodiazepine receptor in Na—K phosphate buffer pH 7.4. A 5 mg aliquot was incubated with 1 nM ($^3$H)-flunitrazepam for 60 minutes at 25° C. Experiments were performed in the presence or absence of 30 μM of GABA. Non-specific binding was estimated in the presence of 10 μM of diazepam. Membranes were filtered and washed, the filters were then counted to determine ($^3$H)-flunitrazepam specifically bound. Test compounds were tested in duplicate according to the required concentrations (Damm, H. W., et al. (1978) *Res. Comm. Chem. Pathol. Pharmacol.* 22: 597-560 incorporated herein in its entirety; Speth, R. C., et al. (1979) *Life Sci.* 24: 351-357 incorporated herein in its entirety).

Binding Assay 2:
Materials and Methods:
  Receptor Source: Bovine hippocampal membranes
  Radioligand: [3H]-RY80 (40-80 Ci/mmol)
  Final ligand concentration—[0.8 nM]
  Non-specific Determinant: L-655,708—[0.5 μM]
  Reference Compound: L-655,708
  Positive Control: L-655,708

Binding assay 2 followed procedures based on Li and Szabo (Li M., Szabo A., Rosenberg H. Evaluation of native GABAA receptors containing an α5 subunit. *Eur. J. Pharmacol.* 413: 63-72 (2001)). Incubation Conditions: Reactions are carried out in 50 mM Tris-Citrate (pH 7.8) containing 200 mM NaCl at 0-4° C. for 60 minutes. The reaction is terminated by rapid vacuum filtration onto glass fiber filters. Radioactivity trapped onto the filters is determined and compared to control values in order to ascertain any interactions of test compound with the benzodiazepine (central) binding site.

Electrophysiology Assay
Preparation of RNA
  mRNA was prepared from lyophilized plasmid pellets containing cDNA inserts encoding the specific $GABA_A$ receptor subunit. cDNAs encoding the α2, α3, and γ3 subunits were subcloned into pBluescript, SK$^-$. cDNAs encoding the α1 and α5 subunits were subcloned into prC while cDNA encoding the β2 subunit was subcloned into pcDNA1. The cDNA construct encoding the γ2s subunit is in the pGH19 expression construct. Overnight cultures of transformed DH5a bacterial cells were performed to grow sufficient quantities for maxiprep isolation of the plasmid cDNA. The resulting plasmid cDNA was linearized by digestion with an appropriate restriction enzyme that cleaves distal to the cDNA insert (XbaI for α1,2, β2, and γ3 or NotI for α3,5 and γ2, respectively). Following digestion, plasmid cDNA was treated with proteinase K and extracted with phenol/chloroform/isoamyl alcohol, followed by ethanol precipitation. cDNA quality was assessed by agarose-gel electrophoresis (1.5% agarose gel). Samples were stored at −20° C. until use. In vitro transcription was performed with T7 RNA polymerase. mRNA was then stored at −80° C. until use. Plasmids were linearized with appropriate restriction enzymes before in vitro transcription using the Message Machine kit (Ambion, Austin, Tex.).

$GABA_A$ Receptor Expression in *Xenopus* oocytes.

GABA$_A$ receptor expression in *Xenopus oocytes:* Following 45 min of 0.15% Tricaine anesthesia, an ovarian section containing the follicular oocytes was removed from the frog through a lateral abdominal incision. *Oocytes* were immediately placed in a calcium-free solution (NaCl 96 mM, MgCl$_2$ 1 mM, KCl 2 mM, Hepes 50 mM, pyruvate 2.5 mM, gentamycin 100 μg/mL, penicillin-streptomycin 50 U/mL, pH 7.4). Following 1.5-2 hour incubation in 0.2% collagenase (type II, Sigma Chemical Co., St. Louis, Mo.) at room temperature, individual Dumont stage V and VI oocytes were transferred to an incubator and maintained overnight in Barth's solution (NaCl 84 mM, NaHCO$_3$ 2.4 mM, MgSO$_4$ 0.82 mM, KCl 1 mM, Ca(NO$_3$)$_2$ 0.33 mM, CaCl$_2$ 0.41 mM, Tris/HCl 7.5 mM, pyruvate 2.5 mM, gentamycin 50 μg/mL, penicillin-streptomycin, 100 units/mL, pH 7.4) at 18-20° C. and used for experiments 1-5 days post-injection. Oocytes were injected solution using an electronic microinjector (Drummond, Broomall, Pa.) with 50 nL of RNA containing 0.3-0.5 ng of each subunit RNA in a 1:1:1 ratio. The injected oocytes were used for experiments after 1-5 days of incubation in Barth's solution at 18-20° C.

Electrophysiology:

Measurements of ion currents from oocytes expressing GABA$_A$ receptors were performed using a Warner two-electrode voltage-clamp amplifier (Warner Instruments, Inc., Foster City, Calif.) (Park-Chung, M., et al. (1999) *Brain Res.* 830: 72-87 incorporated herein in its entirety). Microelectrodes were fabricated from borosilicate glass capillaries with a programmed pipette puller (Sutter Instrument Co., Calif.). Microelectrode resistance was 1-3 MΩ when filled with 3 M KCl. The oocyte recording chamber was continuously perfused with Ringer solution. Oocytes were clamped at a holding potential of -70 mV during data acquisition. The membrane current was filtered at 10 Hz and sampled at 100 Hz. Compounds were applied by a gravity-driven external perfusion system. The working volume of the recording chamber was 30 μL and the rate of the perfusion was approximately 50 μL/sec. Compound application was 10-20 sec followed by a 90 sec wash. Data acquisition and external perfusion was computer controlled by custom-developed software. All experiments were performed at room temperature (22-24° C.). Dose-response data from each oocyte were fitted to the Hill equation by non-linear regression using the equation:

$$I_{GABA} = Emax/(1+(EC_{50}/c)^{nH})$$

Emax is the maximum response, EC$_{50}$ is the concentration producing 50% of the maximal response, n$_H$ is the Hill coefficient and c is the concentration of agonist. Based on the GABA concentration-response curve fit, an EC$_{10}$ for GABA was determined for each subunit combination, and this concentration was used for subsequent modulator concentration-response studies. Peak current measurements were normalized and expressed as a fraction of the peak control current measurements. Control current responses to an EC$_{10}$ concentration of GABA were re-determined after every 2-4 modulator applications. Percent modulation was determined by the equation:

$$\% \text{ change} = (I'/I-1) \times 100$$

where I is the control response at the GABA EC$_{10}$ and I' the response in the presence of modulator (Lippa A, et al. (2005) *Proc. Natl. Acad. Sci. USA* 102(20): 7380-7385 incorporated herein in its entirety).

Some compounds showed positive modulation and some showed negative modulation at a screening concentration of 10 μM.

wherein:
A indicates % inhibition >80%
B indicates % inhibition <80% and >20%
C indicates % inhibition <20%
EP indicates electrophysiology
D indicates negative modulation >20%
E indicates negative modulation <20%
ND indicates not determined All compounds disclosed in Table 1 are assumed to be drawn as neutral. If not indicated, a hydrogen atom is assumed to be present on nitrogen atoms to provide a neutral compound. The compounds of Table 1 can exist in additional isomeric forms, for example, the compounds can exist as tautomers of the drawn structures. The compounds disclosed in Table 1 encompass all possible tautomers of the drawn structures. One of skill in the art will understand that a compound can exist in different tautomeric forms or mixtures there of depending on the environment encompassing the compound, that is an equilibrium can exist between the different tautomerics forms of the compounds and the equilibrium between said forms can be influenced by outside factors.

TABLE 1

| | | % Inhibition at 10 μM | % Inhibition at 0.1 μM | EP Modulation |
|---|---|---|---|---|
| 6a | 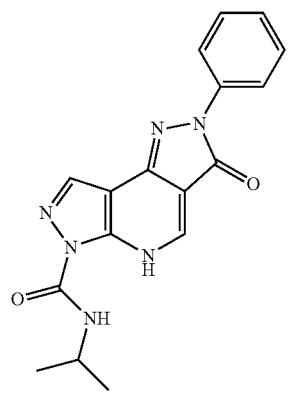 | B | C | ND |

TABLE 1-continued

| | | % Inhibition at 10 μM | % Inhibition at 0.1 μM | EP Modulation |
|---|---|---|---|---|
| 6b | | A | A | D |
| 6c | | A | B | D |
| 6d | | A | ND | E |

TABLE 1-continued

| | | % Inhibition at 10 μM | % Inhibition at 0.1 μM | EP Modulation |
|---|---|---|---|---|
| 6e | | A | C | ND |
| 6f | | A | ND | D |
| 6g | | A | B | ND |

TABLE 1-continued
| | | % Inhibition at 10 μM | % Inhibition at 0.1 μM | EP Modulation |
|---|---|---|---|---|
| 7a | 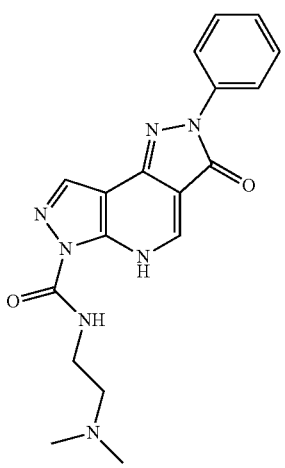 [SMILES: CN(C)CCNC(=O)n1ncc2c3nn(-c4ccccc4)c(=O)c-3c[nH]c21] | B | C | E |
| 6h | 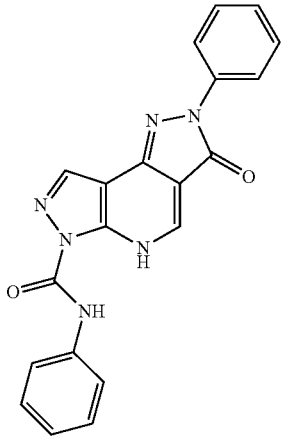 [SMILES: O=C(Nc1ccccc1)n1ncc2c3nn(-c4ccccc4)c(=O)c-3c[nH]c21] | B | C | D |
| 7b | 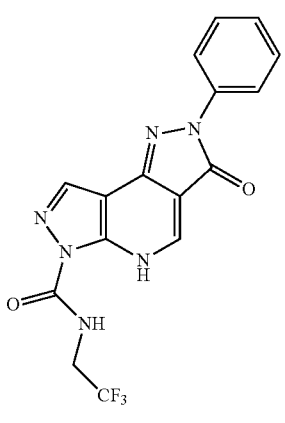 [SMILES: O=C(NCC(F)(F)F)n1ncc2c3nn(-c4ccccc4)c(=O)c-3c[nH]c21] | A | B | D |

TABLE 1-continued
| | | % Inhibition at 10 μM | % Inhibition at 0.1 μM | EP Modulation |
|---|---|---|---|---|
| 6i | 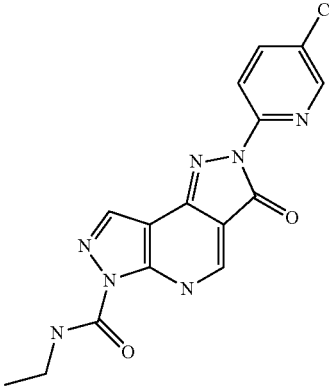 | A | ND | D |
| 7d | 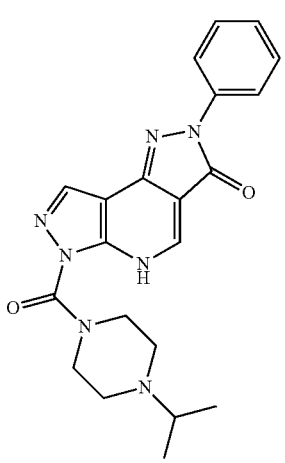 [SMILES: CC(C)N1CCN(C(=O)n2ncc3c4nn(-c5ccccc5)c(=O)c-4c[nH]c32)CC1] | C | C | Positive |
| 6j | 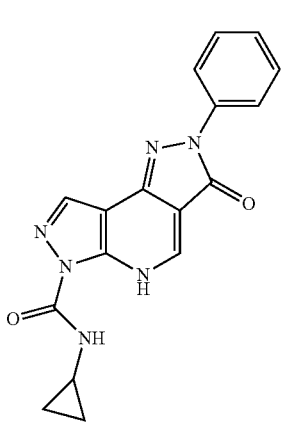 [SMILES: O=C(NC1CC1)n1ncc2c3nn(-c4ccccc4)c(=O)c-3c[nH]c21] | A | C | E |

TABLE 1-continued
| | | % Inhibition at 10 μM | % Inhibition at 0.1 μM | EP Modulation |
|---|---|---|---|---|
| 6k | 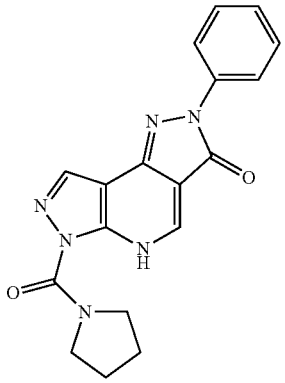 [SMILES: O=C(N1CCCC1)n1ncc2c3nn(-c4ccccc4)c(=O)c-3c[nH]c21] | C | C | ND |
| 7c | 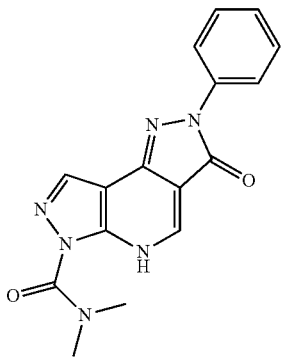 [SMILES: CN(C)C(=O)n1ncc2c3nn(-c4ccccc4)c(=O)c-3c[nH]c21] | B | ND | ND |
| 6l | 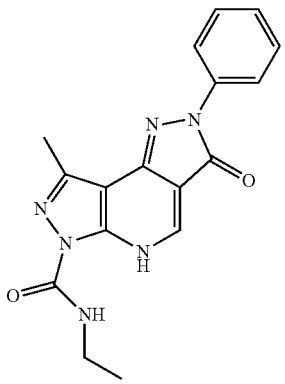 [SMILES: CCNC(=O)n1nc(C)c2c3nn(-c4ccccc4)c(=O)c-3c[nH]c21] | A | A | D |
| 6m | 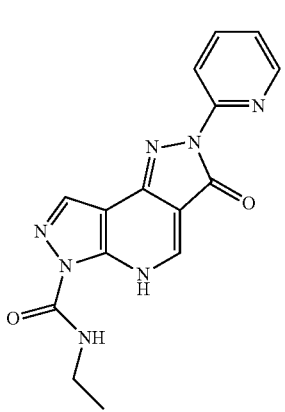 [SMILES: CCNC(=O)n1ncc2c3nn(-c4ccccn4)c(=O)c-3c[nH]c21] | A | C | D |

TABLE 1-continued

| | | % Inhibition at 10 μM | % Inhibition at 0.1 μM | EP Modulation |
|---|---|---|---|---|
| 6n | | C | C | E |
| 6o | | A | B | E |
| 6p | | C | C | ND |

TABLE 1-continued

| | | % Inhibition at 10 μM | % Inhibition at 0.1 μM | EP Modulation |
|---|---|---|---|---|
| 6q | | C | ND | ND |
| 6r | | B | ND | ND |
| 6s | | B | ND | ND |

TABLE 1-continued

| | | % Inhibition at 10 μM | % Inhibition at 0.1 μM | EP Modulation |
|---|---|---|---|---|
| 6t | [structure] | C | ND | ND |
| 6u | [structure] | A | ND | D |
| 6v | [structure] | B | ND | ND |

TABLE 1-continued

| | % Inhibition at 10 μM | % Inhibition at 0.1 μM | EP Modulation |
|---|---|---|---|
| 6w | A | ND | E |
| 6x | A | ND | ND |
| 6y | A | ND | ND |

TABLE 1-continued

| | % Inhibition at 10 μM | % Inhibition at 0.1 μM | EP Modulation |
|---|---|---|---|
| 6z | A | ND | E |
| 6aa | B | ND | ND |
| 6ab | A | ND | ND |

TABLE 1-continued
| | | % Inhibition at 10 μM | % Inhibition at 0.1 μM | EP Modulation |
|---|---|---|---|---|
| 6ac | 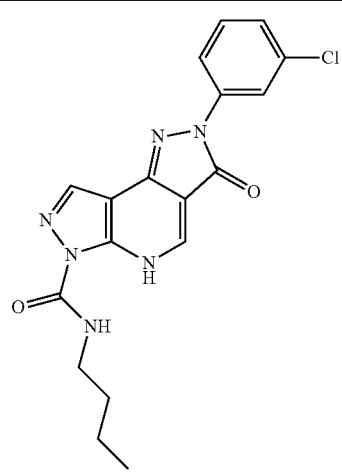 | A | ND | ND |
| 6ad | 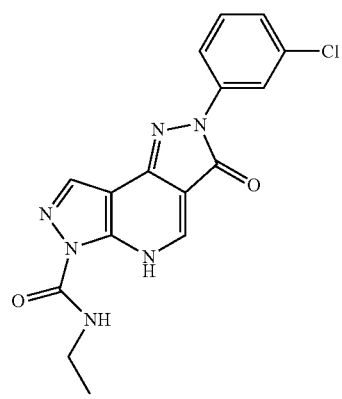 [SMILES: CCNC(=O)n1ncc2c3nn(-c4cccc(Cl)c4)c(=O)c-3c[nH]c21] | A | ND | E |
| 6ae | 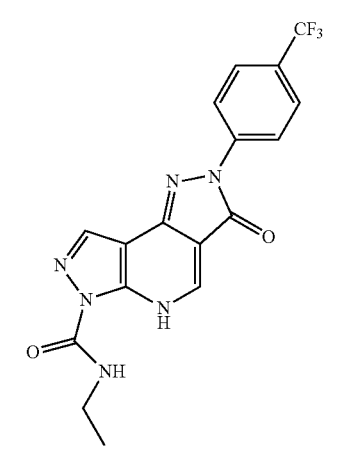 [SMILES: CCNC(=O)n1ncc2c3nn(-c4ccc(C(F)(F)F)cc4)c(=O)c-3c[nH]c21] | A | ND | E |

TABLE 1-continued

| | | % Inhibition at 10 μM | % Inhibition at 0.1 μM | EP Modulation |
|---|---|---|---|---|
| 6af | *(structure)* | B | ND | ND |
| 6ag | *(structure)* | B | ND | ND |
| 6ah | *(structure)* | B | ND | ND |

TABLE 1-continued

| | | % Inhibition at 10 μM | % Inhibition at 0.1 μM | EP Modulation |
|---|---|---|---|---|
| 6ai | | A | C | 0 |
| 6aj | | B | C | ND |
| 6ak | | A | C | ND |

TABLE 1-continued

| | | % Inhibition at 10 μM | % Inhibition at 0.1 μM | EP Modulation |
|---|---|---|---|---|
| 6al | | A | C | ND |
| 6am | | A | B | ND |
| 6an | | A | B | ND |

TABLE 1-continued
| | | % Inhibition at 10 μM | % Inhibition at 0.1 μM | EP Modulation |
|---|---|---|---|---|
| 6ao | 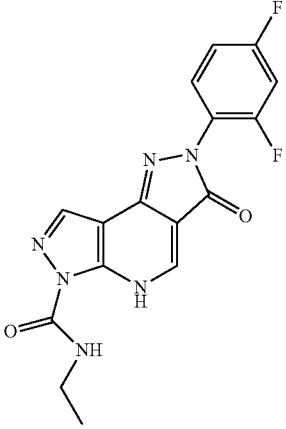 [SMILES: CCNC(=O)n1ncc2c3nn(-c4ccc(F)cc4F)c(=O)c-3c[nH]c21] | A | B | ND |
| 6ap | 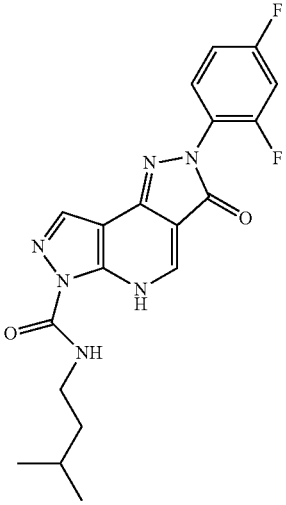 [SMILES: CC(C)CCNC(=O)n1ncc2c3nn(-c4ccc(F)cc4F)c(=O)c-3c[nH]c21] | A | C | ND |
| 6aq | 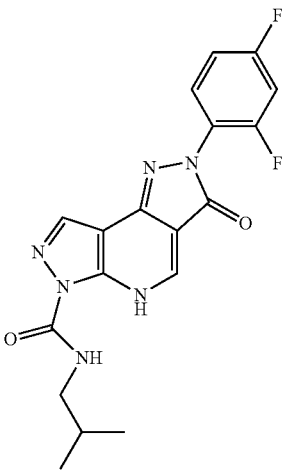 [SMILES: CC(C)CNC(=O)n1ncc2c3nn(-c4ccc(F)cc4F)c(=O)c-3c[nH]c21] | B | C | ND |

TABLE 1-continued

| | % Inhibition at 10 μM | % Inhibition at 0.1 μM | EP Modulation |
|---|---|---|---|
| 6ar | A | ND | E |
| 6as | A | ND | D |
| 6at | A | A | ND |

TABLE 1-continued

| | | % Inhibition at 10 μM | % Inhibition at 0.1 μM | EP Modulation |
|---|---|---|---|---|
| 6au | | A | B | ND |
| 6av | | A | B | E |
| 13a | | A | A | D |
| 13b | | A | A | D |

TABLE 1-continued

| | | % Inhibition at 10 μM | % Inhibition at 0.1 μM | EP Modulation |
|---|---|---|---|---|
| 13c | | A | A | D |
| 13d | | A | B | D |
| 13e | | A | B | E |
| 13f | | A | A | D |

TABLE 1-continued

| | | % Inhibition at 10 μM | % Inhibition at 0.1 μM | EP Modulation |
|---|---|---|---|---|
| 13g | | A | B | D |
| 13h | | A | A | ND |
| 13i | | A | A | E |
| 13j | | A | B | ND |

TABLE 1-continued

| | | % Inhibition at 10 μM | % Inhibition at 0.1 μM | EP Modulation |
|---|---|---|---|---|
| 17a | | C | C | ND |
| 17b | | B | C | ND |
| 17c | | C | C | ND |

TABLE 1-continued

| | % Inhibition at 10 μM | % Inhibition at 0.1 μM | EP Modulation |
|---|---|---|---|
| 17d | C | C | ND |
| 17e | B | ND | ND |
| 6aw | B | ND | ND |

TABLE 1-continued

| | | % Inhibition at 10 μM | % Inhibition at 0.1 μM | EP Modulation |
|---|---|---|---|---|
| 6ax | *structure* | A | ND | ND |
| 6ay | *structure* | A | ND | D |
| 6az | *structure* | A | ND | ND |
| 13k | *structure* | A | B | ND |

TABLE 1-continued

| | | % Inhibition at 10 μM | % Inhibition at 0.1 μM | EP Modulation |
|---|---|---|---|---|
| 17f | 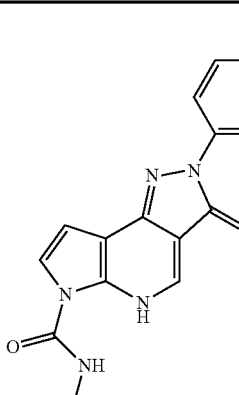 | B | ND | ND |
| 21a | 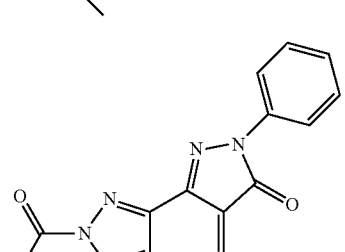 | C | B | D |

What is claimed is:

1. A compound of formula (I):

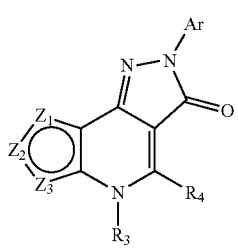

or tautomer thereof, or their pharmaceutically acceptable salts, wherein:

$Z_1$, $Z_2$ and $Z_3$ are each independently N (nitrogen), $NR_7$ or $CR_8$, wherein at least one of $Z_1$, $Z_2$ or $Z_3$ is $NR_7$;

$R_7$ is —C(=Y)$NR_1R_2$;

$R_8$ is hydrogen, halo, ($C_1$-$C_6$)alkyl optionally substituted with up to 5 fluoro, or ($C_1$-$C_6$)alkoxy optionally substituted with up to 5 fluoro;

Y is O (oxygen) or S (sulfur);

$R_1$ and $R_2$ are each independently selected from the group consisting of hydrogen, ($C_1$-$C_6$)alkyl, ($C_2$-$C_6$)alkenyl, ($C_2$-$C_6$)alkynyl, hydroxy($C_1$-$C_6$)alkyl, ($C_1$-$C_6$)alkyl$OR_a$, ($C_1$-$C_6$)alkyl optionally substituted with up to 5 fluoro, ($C_1$-$C_6$)alkyl optionally substituted with up to 5 chloro, ($C_1$-$C_6$)alkoxy optionally substituted with up to 5 fluoro, ($C_1$-$C_6$)alkyl$NR_aR_b$, and aryl, or $R_1$ and $R_2$ are taken together with the nitrogen to which they are attached to form a heterocycle group optionally substituted with one or more $R_c$; wherein the heterocycle group optionally include one or more groups selected from O (oxygen), S(O)$_x$, and $NR_d$;

x is 0, 1 or 2;

Ar is aryl, or heteroaryl, each optionally substituted with one or more M;

$R_3$ is hydrogen or oxide;

$R_4$ is selected from the group consisting of hydrogen, hydroxy, halo, hydroxy($C_1$-$C_6$)alkyl, ($C_1$-$C_6$)alkyl optionally substituted with up to 5 fluoro, and ($C_1$-$C_6$)alkoxy optionally substituted with up to 5 fluoro;

each $R_a$ and $R_b$ is independently hydrogen, ($C_1$-$C_6$)alkyl, aryl, heteroaryl, heterocycle, ($C_1$-$C_6$)alkylaryl, —S(O)$_x$($C_1$-$C_6$)alkyl, —S(O)-aryl, or —C(O)($C_1$-$C_6$)alkyl;

each $R_c$ is independently hydrogen, aryl, heteroaryl, heterocycle or ($C_1$-$C_6$)alkyl optionally substituted with up to 5 fluoro;

each $R_d$ is independently hydrogen, halo, oxo, hydroxy, —C(O)$NR_eR_f$, cyano, nitro, hydroxy($C_1$-$C_6$)alkyl, aryl, aryl($C_1$-$C_6$)alkyl, ($C_1$-$C_6$)alkyl optionally substituted with up to 5 fluoro, ($C_1$-$C_6$)alkoxy optionally substituted with up to 5 fluoro, or ($C_1$-$C_6$)alkyl substituted with one or more $R_{dd}$;

$R_{dd}$ is hydroxyl, alkoxy, alkylamino or halo;

each M is independently hydrogen, halo, $CF_3$, $CF_2H$, hydroxy, methoxy, trifluoromethoxy, cyano, nitro, ($C_1$-$C_6$)alkyl, hydroxy($C_1$-$C_6$)alkyl, ($C_1$-$C_6$)alkoxy, —$NR_aR_b$, aryl, heteroaryl or heterocycle; and each $R_e$ and $R_f$ is independently ($C_1$-$C_6$)alkyl.

2. The compound of claim 1, wherein Ar is:

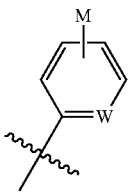

where W is CM or N (nitrogen).

3. The compound of claim 1 having the formula Ia:

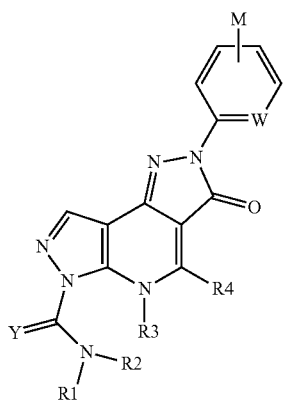

(Ia)

or a tautomer thereof, or their pharmaceutically acceptable salts, wherein W is CM or N (nitrogen); Y is O (oxygen) or S (sulfur); and each M is independently hydrogen, halo, $CF_3$, $CF_2H$, hydroxy, methoxy, $(C_1-C_6)$alkyl, hydroxy $(C_1-C_6)$alkyl, $(C_1-C_6)$alkoxy, aryl, heteroaryl or heterocycle.

4. The compound of claim 1 having the formula Ib:

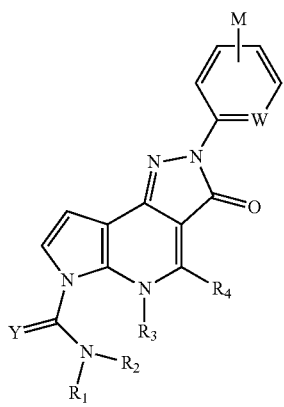

(Ib)

or a tautomer thereof, or their pharmaceutically acceptable salts, wherein W is CM or N (nitrogen); Y is O (oxygen) or S (sulfur); and each M is independently hydrogen, halo, $CF_3$, $CF_2H$, hydroxy, methoxy, $(C_1-C_6)$alkyl, hydroxy $(C_1-C_6)$alkyl, $(C_1-C_6)$alkoxy, aryl, heteroaryl or heterocycle.

5. The compound of claim 1 having the formula Ic:

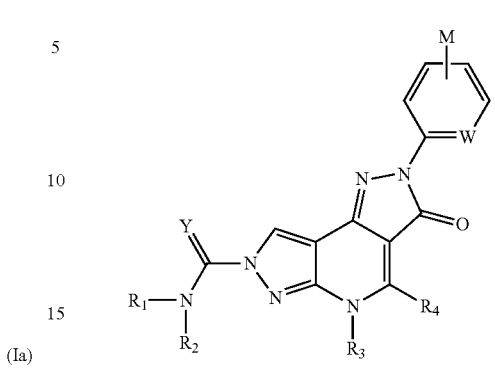

(Ic)

or a tautomer thereof, or their pharmaceutically acceptable salts, wherein W is CM or N (nitrogen); Y is O (oxygen) or S (sulfur); and each M is independently hydrogen, halo, $CF_3$, $CF_2H$, hydroxy, methoxy, $(C_1-C_6)$alkyl, hydroxy $(C_1-C_6)$alkyl, $(C_1-C_6)$alkoxy, aryl, heteroaryl or heterocycle.

6. The compound of claim 1 having the formula Id:

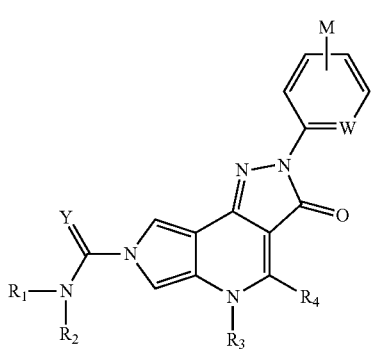

(Id)

or a tautomer thereof, or their pharmaceutically acceptable salts, wherein W is CM or N (nitrogen); Y is O (oxygen) or S (sulfur); and each M is independently hydrogen, halo, $CF_3$, $CF_2H$, hydroxy, methoxy, $(C_1-C_6)$alkyl, hydroxy $(C_1-C_6)$alkyl, $(C_1-C_6)$alkoxy, aryl, heteroaryl or heterocycle.

7. The compound of claim 1 having the formula Ie:

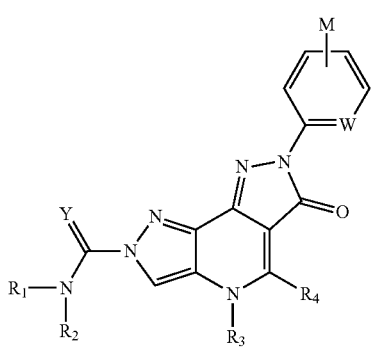

(Ie)

or a tautomer thereof, or their pharmaceutically acceptable salts, wherein W is CM or N (nitrogen); Y is O (oxygen) or S (sulfur); and each M is independently hydrogen, halo, $CF_3$, $CF_2H$, hydroxy, methoxy, ($C_1$-$C_6$)alkyl, hydroxy ($C_1$-$C_6$)alkyl, ($C_1$-$C_6$)alkoxy, aryl, heteroaryl or heterocycle.

8. The compound of claim 1 having the formula Ig:

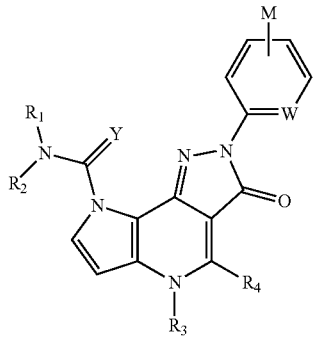

(Ig)

or a tautomer thereof, or their pharmaceutically acceptable salts, wherein W is CM or N (nitrogen); Y is O (oxygen) or S (sulfur); and each M is independently hydrogen, halo, $CF_3$, $CF_2H$, hydroxy, methoxy, ($C_1$-$C_6$)alkyl, hydroxy ($C_1$-$C_6$)alkyl, ($C_1$-$C_6$)alkoxy, aryl, heteroaryl or heterocycle.

9. The compound of claim 1 having the formula IIa:

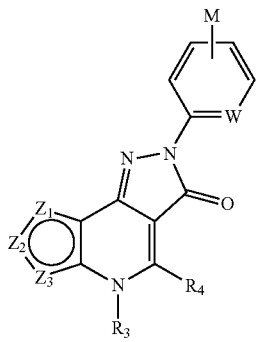

(IIa)

or a tautomer thereof, or their pharmaceutically acceptable salts, wherein $R_7$ is —C(=O)$NR_1R_2$; W is CM or N (nitrogen); and each M is independently hydrogen, halo, $CF_3$, $CF_2H$, hydroxy, methoxy, ($C_1$-$C_6$)alkyl, hydroxy($C_1$-$C_6$)alkyl, ($C_1$-$C_6$)alkoxy, aryl, heteroaryl or heterocycle.

10. The compound of claim 1 having the formula IIb:

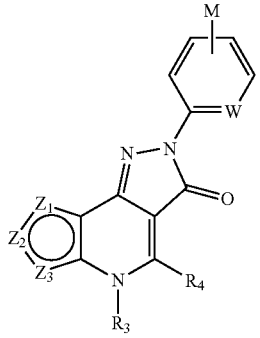

(IIb)

or a tautomer thereof, or their pharmaceutically acceptable salts, wherein $R_7$ is —C(=S)$NR_1R_2$; wherein W is CM or N (nitrogen); and each M is independently hydrogen, halo, $CF_3$, $CF_2H$, hydroxy, methoxy, ($C_1$-$C_6$)alkyl, hydroxy ($C_1$-$C_6$)alkyl, ($C_1$-$C_6$)alkoxy, aryl, heteroaryl or heterocycle.

11. A compound selected from the group consisting of:

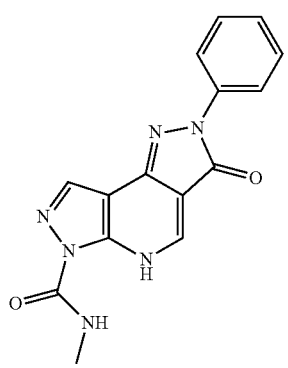

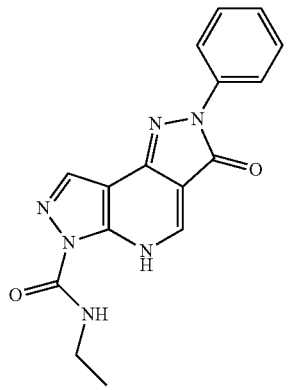

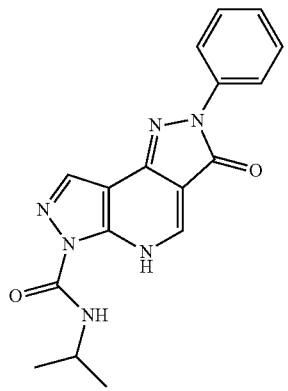

109
-continued
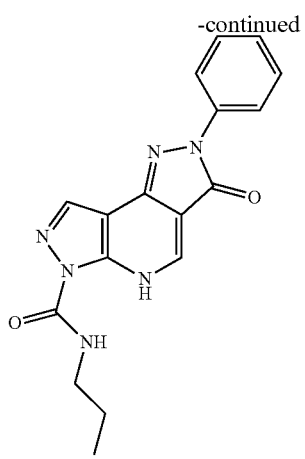
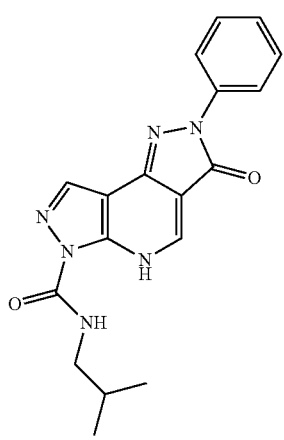
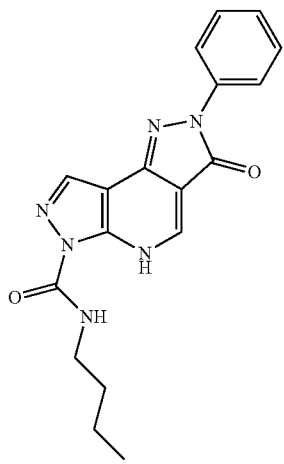
110
-continued
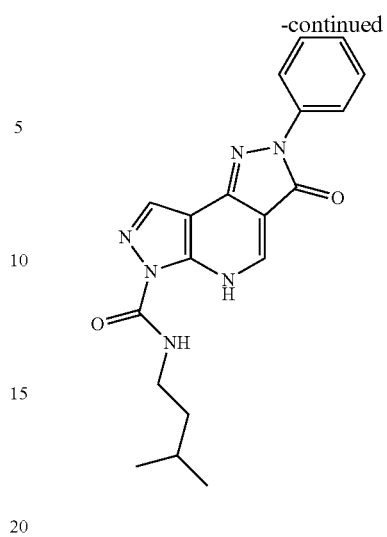
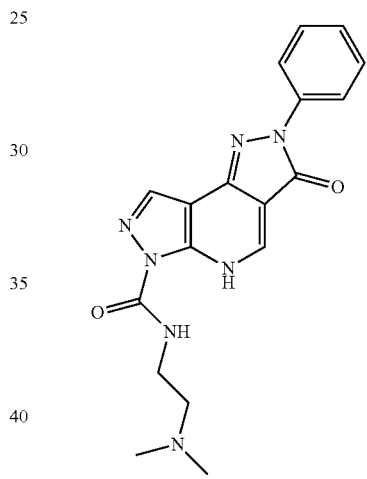
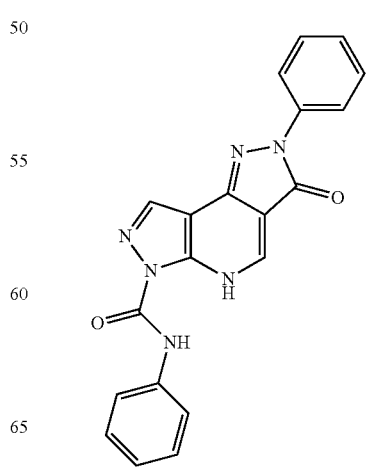

111
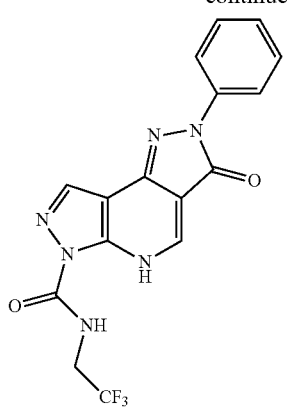
112
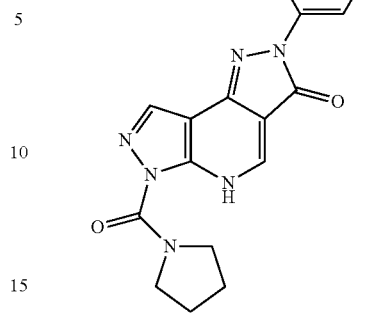
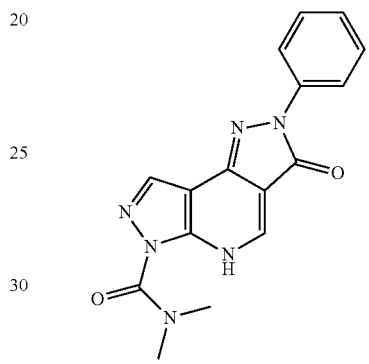
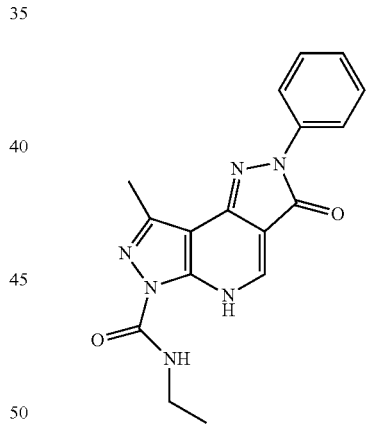
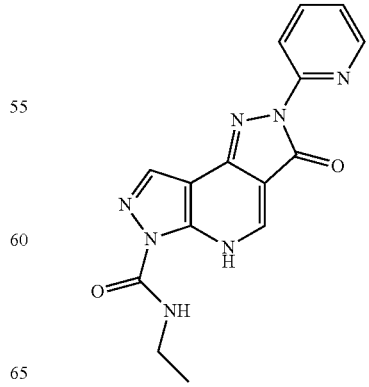

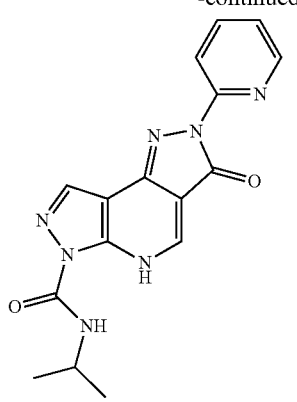
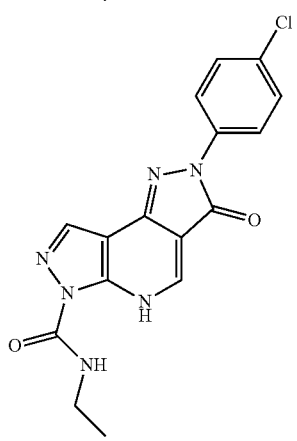
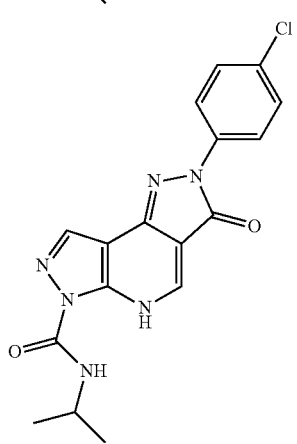
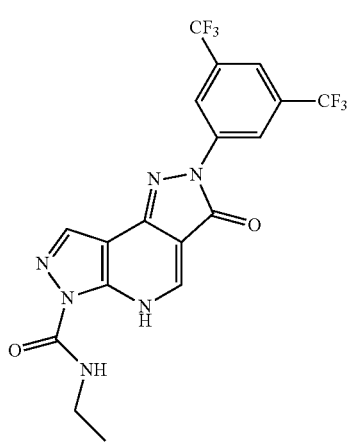
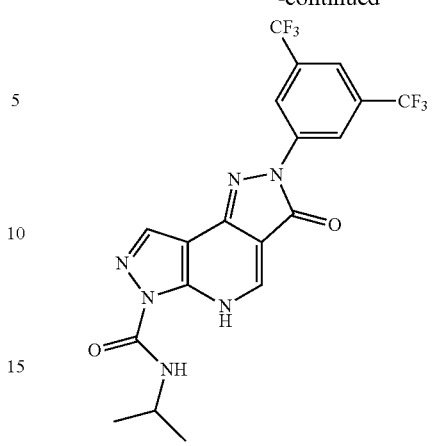
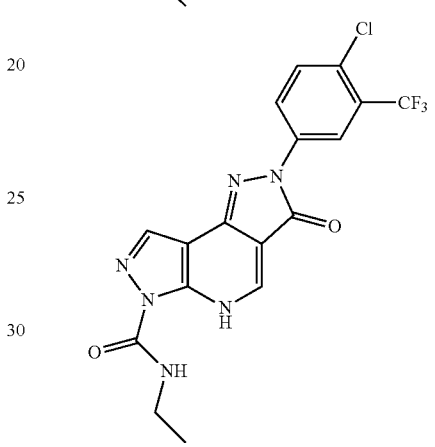
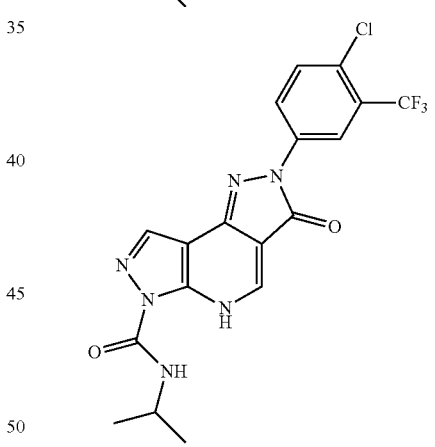
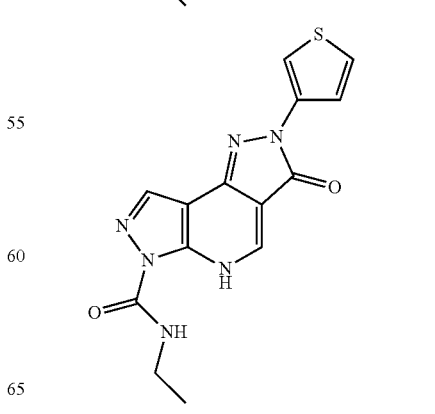

115
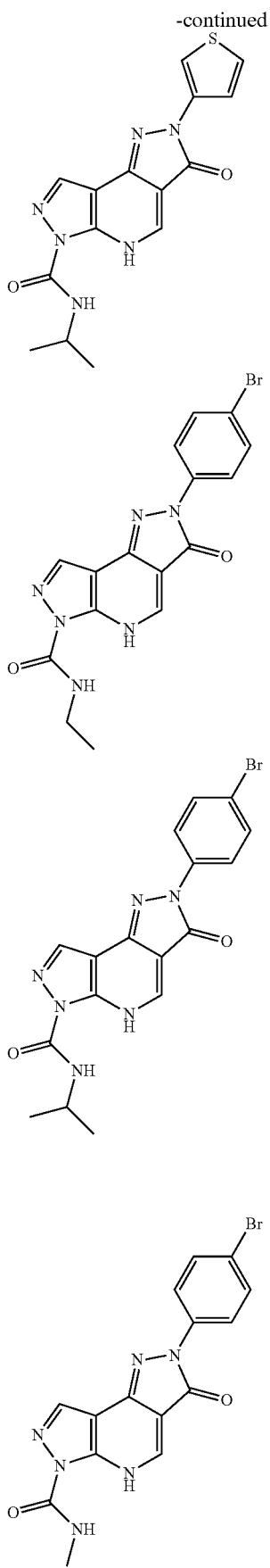
116
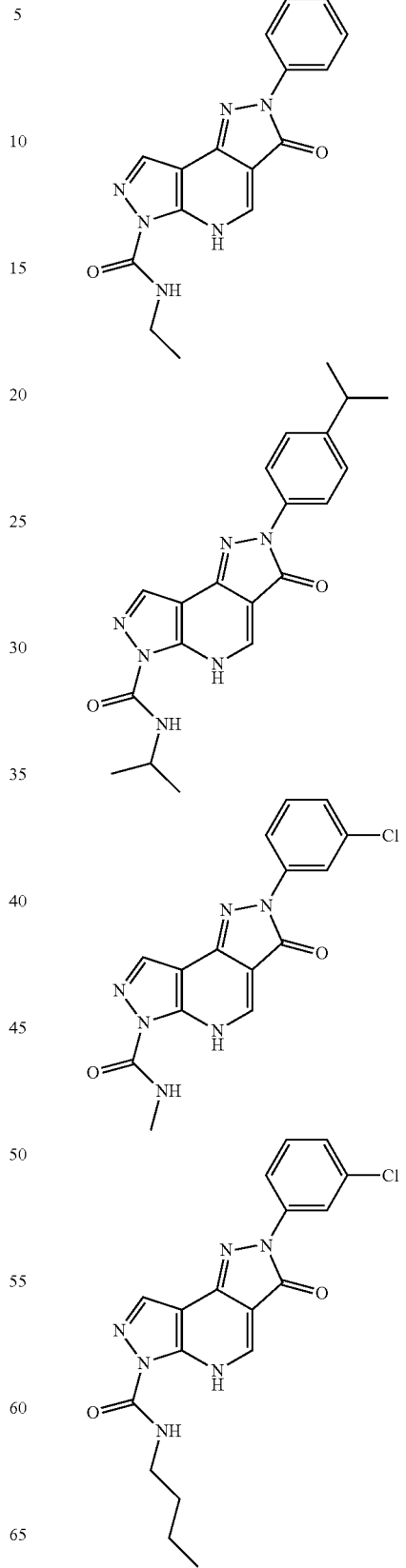

117
-continued
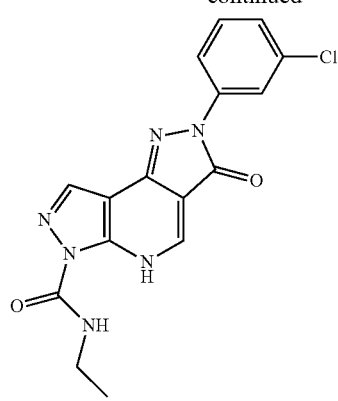
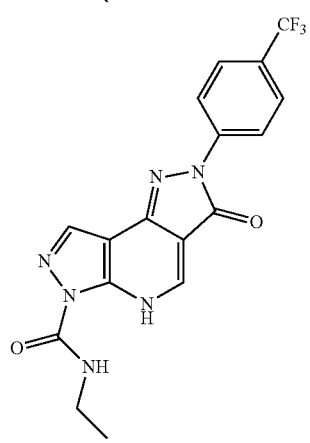
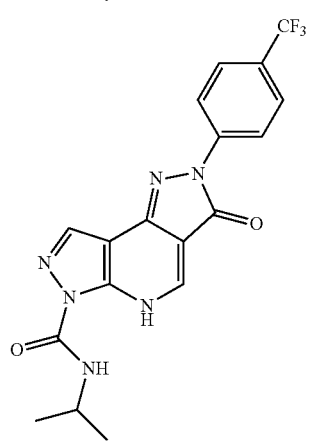
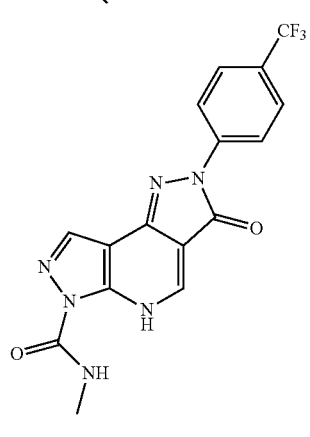
118
-continued
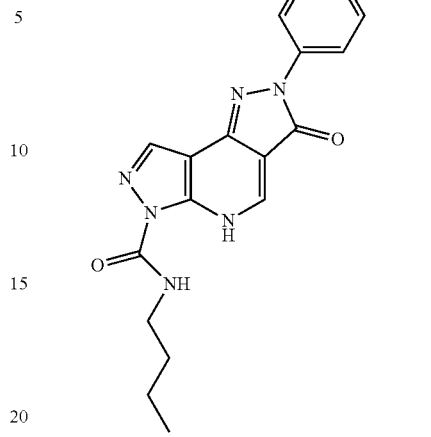
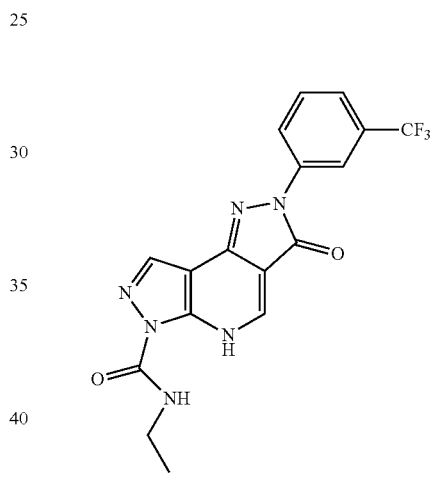
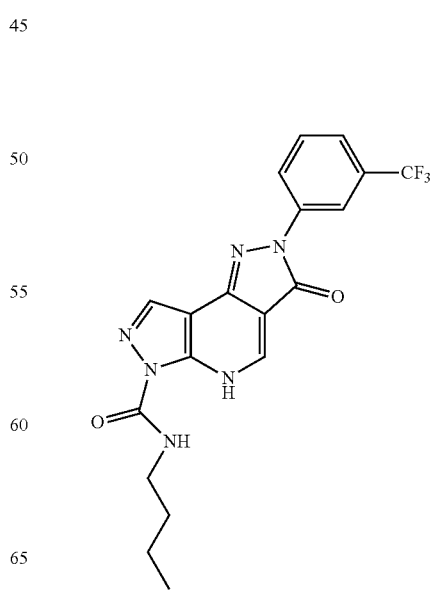

119
-continued
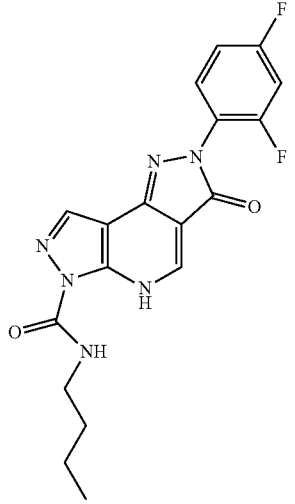
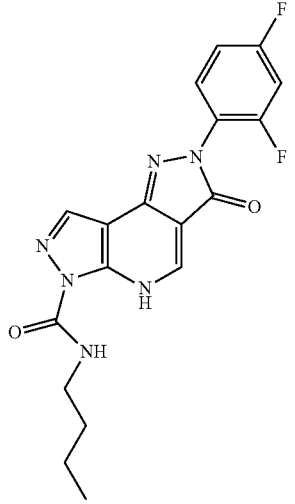
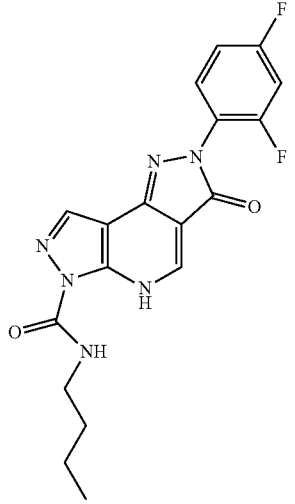
120
-continued
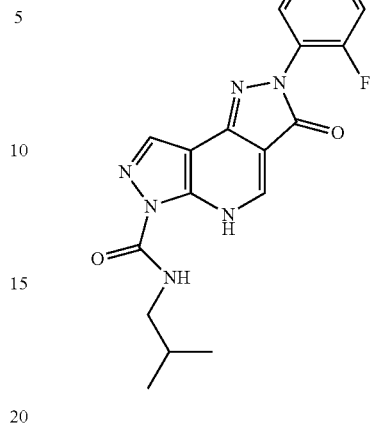
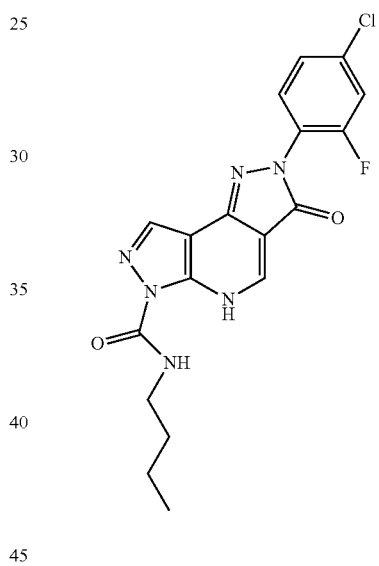
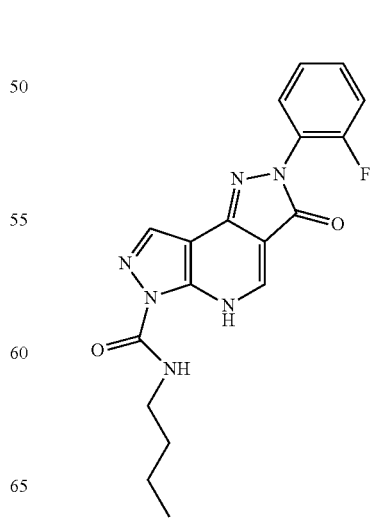

121
-continued
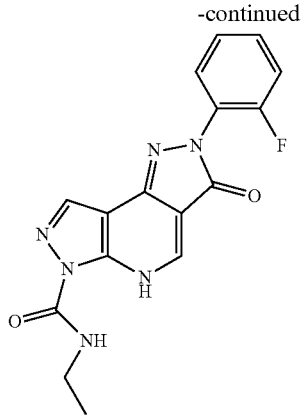
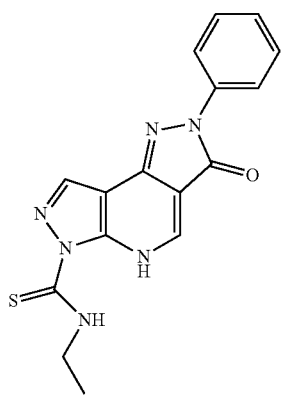 [SMILES: CCNC(=S)n1ncc2c3nn(-c4ccccc4)c(=O)c-3c[nH]c21]
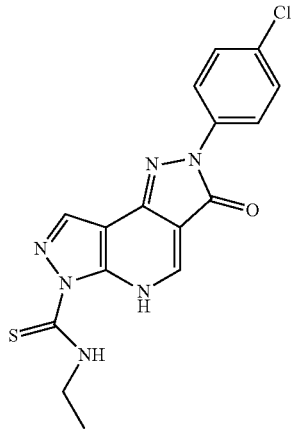 [SMILES: CCNC(=S)n1ncc2c3nn(-c4ccc(Cl)cc4)c(=O)c-3c[nH]c21]
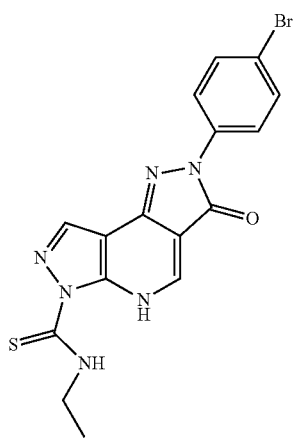
122
-continued
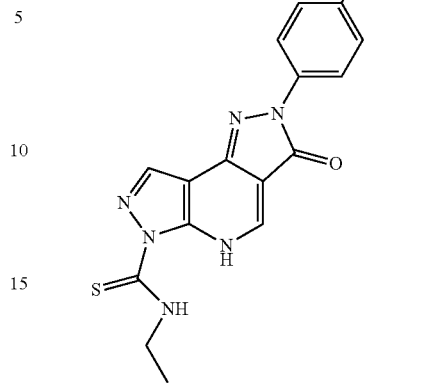
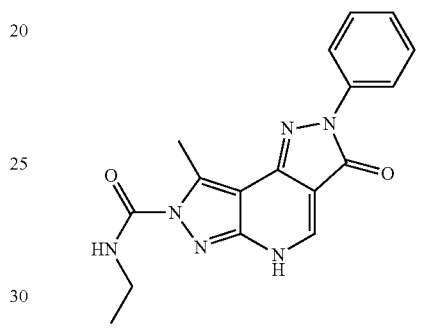
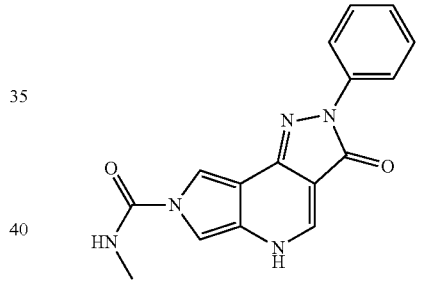
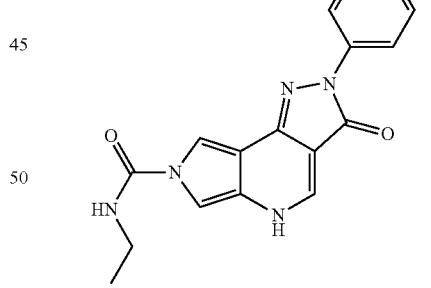
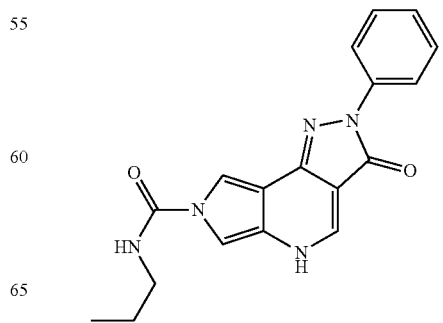

123
-continued
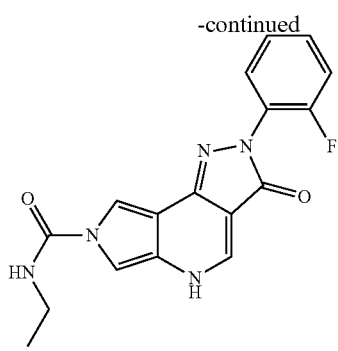
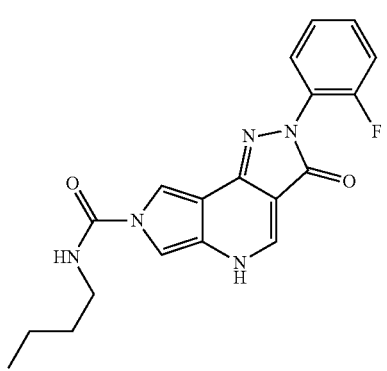 [SMILES: CCCCNC(=O)n1cc2[nH]cc3c(=O)n(-c4ccccc4F)nc-3c2c1]
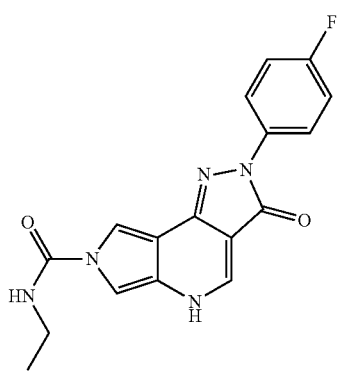 [SMILES: CCNC(=O)n1cc2[nH]cc3c(=O)n(-c4ccc(F)cc4)nc-3c2c1]
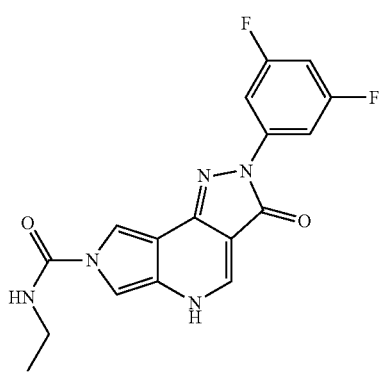
124
-continued
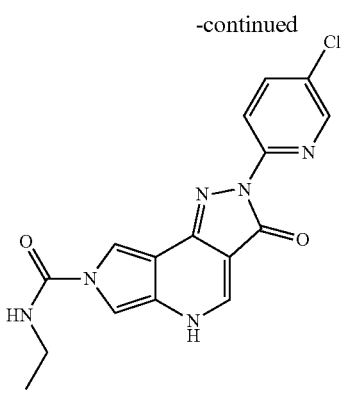
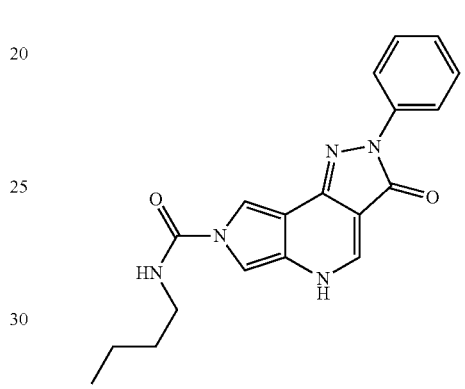
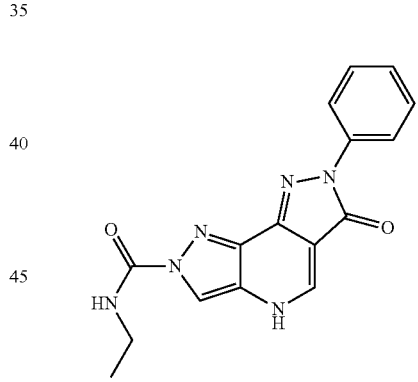
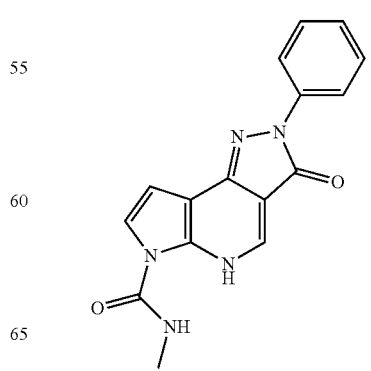

125
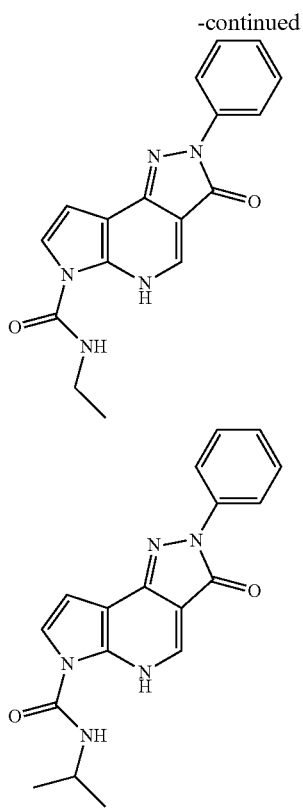
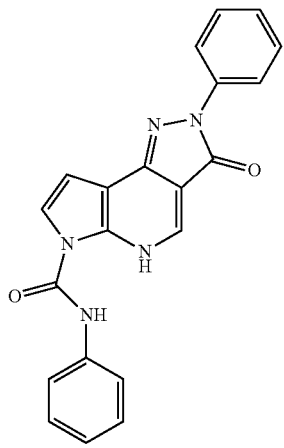
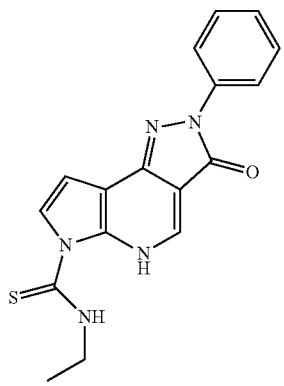
126
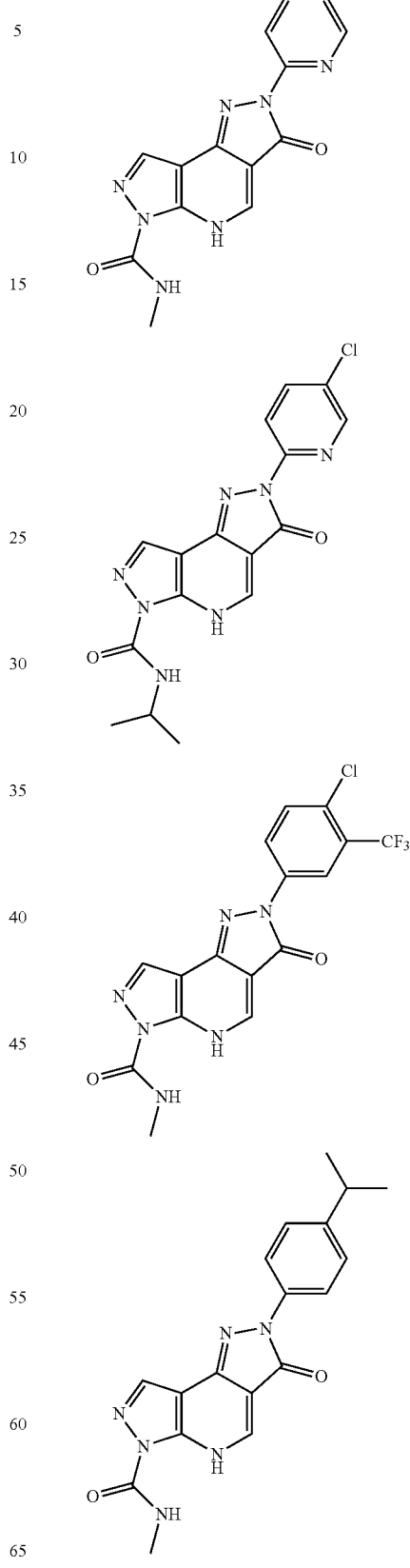

-continued
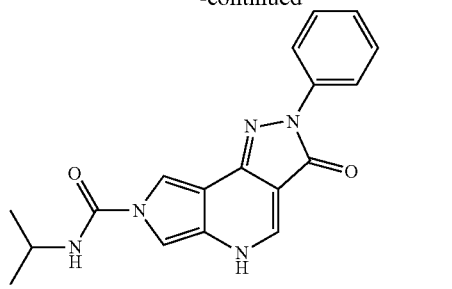
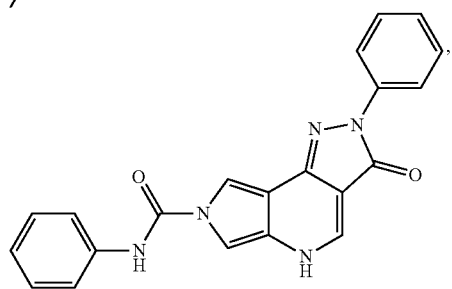
or a tautomer thereof, or their pharmaceutically acceptable salts.
12. A pharmaceutical composition comprising:
a) a compound of claim 1; and
b) a pharmaceutically acceptable carrier.
* * * * *